US012680078B2

(12) United States Patent (10) Patent No.: US 12,680,078 B2
Tryggvason et al. (45) **Date of Patent: \*Jul. 14, 2026**

(54) DIFFERENTIATION OF PLURIPOTENT STEM CELLS AND CARDIAC PROGENITOR CELLS INTO STRIATED CARDIOMYOCYTE FIBERS USING LAMININS LN-511, LN-521 AND LN-221

(71) Applicants:National University of Singapore, Singapore (SG); BioLamina AB, Sundbyberg (SE)

(72) Inventors: Karl Tryggvason, Singapore (SG); Yan Wen Yap, Singapore (SG); Kristian Tryggvason, Sundbyberg (SE); Yi Sun, Sundbyberg (SE)

(73) Assignees: National University of Singapore, Singapore (SG); BioLamina AB, Sundbyberg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,309

(22) Filed: Jun. 22, 2018

(65) Prior Publication Data

US 2018/0362930 A1 Dec. 20, 2018

Related U.S. Application Data

(63) Continuation-in-part of application No. 14/895,669, filed as application No. PCT/IB2014/002289 on Jul. 2, 2014, now Pat. No. 11,001,807.

(60) Provisional application No. 62/523,700, filed on Jun. 22, 2017, provisional application No. 61/842,241, filed on Jul. 2, 2013.

(51) Int. Cl.
| | |
|---|---|
| *C12N 5/077* | (2010.01) |
| *A61K 35/34* | (2015.01) |
| *C12Q 1/6876* | (2018.01) |
| *C12Q 1/6881* | (2018.01) |
| *A61K 9/00* | (2006.01) |

(52) U.S. Cl.
CPC ............ *C12N 5/0657* (2013.01); *A61K 35/34* (2013.01); *C12Q 1/6876* (2013.01); *C12Q 1/6881* (2013.01); *A61K 9/0019* (2013.01); *C12N 2500/98* (2013.01); *C12N 2501/415* (2013.01); *C12N 2501/998* (2013.01); *C12N 2506/02* (2013.01); *C12N 2533/52* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 5,942,435 | A | 8/1999 | Wheeler | |
| 2011/0123500 | A1* | 5/2011 | Anversa | A61P 9/00 |
| | | | | 424/93.7 |
| 2013/0330825 | A1* | 12/2013 | Couture | C12N 5/0657 |
| | | | | 435/377 |

FOREIGN PATENT DOCUMENTS

| | | | | |
|---|---|---|---|---|
| WO | WO 2012/080844 A1 | 6/2012 | | |
| WO | WO-2014011095 A1 * | 1/2014 | .......... | C12N 5/0657 |
| WO | WO-2015004239 A1 * | 1/2015 | .......... | C12Y 204/99 |
| WO | WO-2015004539 A2 * | 1/2015 | .......... | C12N 5/0657 |

OTHER PUBLICATIONS

Oh et al Proc. National Acad. Science, 100, 21, 12313-12318 (Year: 2003).*
Gonzalez et al Angew. Chem. Int. Ed. Engl. 50, 11181-11185 Dec. 20, 2012 (Year: 2011).*
Lian et al Nature Protocols, 8, 162-175, online published on Dec. 20, 2012 (Year: 2013).*
Beqqali et al Stem Cells 24, 1956-1967 (Year: 2006).*
Christoforou et al PLoS One.;8(6):e65963, pp. 1-17 (Year: 2013).*
Ong et al PLos One , 8(7), e68335, I-58 (Year: 2013).*
Lee et al Genomics Inform 15(4): 156-161 (Year: 2017).*
Gonzalez et al Angew. Chem. Int. Ed. 50, 11181-11185, (Year: 2011).*
Rodin et al Nature Biotechnology, 28, 611-617) (Year: 2010).*
Von der Mark et al Journal of Biological Chem. 277(8), 6012-6016 (Year: 2002).*
Nishiuchi et al(Matrix Biology 25 , 89-197 (Year: 2006).*
Yap et al Eurp. Heart Journal, 37, 7, pp. 705, abstract only (Year: 2016).*
Liu et al PNAS, 3859-3864 (Year: 2007).*
Bouter Cir. Res. 92: 234-242 (Year: 2003).*
Menasche European Heart Journal, 36, 2011-2017 (Year: 2015).*
Masson et al Retrovirolog 12:45, 1-12) (Year: 2015).*
Ng EMBO Journal 31,522-533 (Year: 2012).*
Yang et al Nature 453, 524-528 (Year: 2008).*
Yap et al (Cell Reports, 26, 3261-3245) (Year: 2019).*
Yap et al Cell Reports 26, 3231-3245 (Year: 2019).*
Matsuura et al., "Creation of mouse embryonic stem cell-derived cardiac cell sheets", Biomaterials 32 (2011) 7355-7362.
Zhu et al., "Methods for the Derivation and Use of Cardiomyocytes from Human Pluripotent Stem Cells", Methods Mol. Biol. 2011, 767, 419-431.
Ting et al., "Differentiation of Human Embryonic Stem Cells to Cardiomyocytes on Microcarrier Cultures", Current Protocols in Stem Cell Biology, Supplement 21, May 2012, John Wiley & Sons, Inc.

(Continued)

*Primary Examiner* — Anoop K Singh
(74) *Attorney, Agent, or Firm* — Lippes Mathias LLP

(57) ABSTRACT

The present disclosure describes methods of differentiating cardiomyocyte progenitor cells and mature cardiomyocyte cells from pluripotent stem cells. The methods may include differentiating pluripotent stems cells on a substrate including (i) laminin-511 or 521 and (ii) laminin-221. The cardiomyocyte progenitor cells and mature cardiomyocyte cells produced by the methods may form a human heart muscle cell line for use in regenerative cardiology. Also described are methods of identifying functional cardiomyocyte progenitor cells and their use in therapeutic applications.

6 Claims, 41 Drawing Sheets
(28 of 41 Drawing Sheet(s) Filed in Color)

(56) References Cited

OTHER PUBLICATIONS

Domogatskaya et al., "Laminin-511 but Not -332, -111, or -411 Enables Mouse Embryonic Stem Cell Self-Renewal In Vitro", Stem Cells 2008, 26, 2800-2809, www.stemcells.com.

Shiraki et al., "Efficient Differentiation of Embryonic Stem Cells into Hepatic Cells In Vitro Using a Feeder-Free Basement Membrane Substratum", PLoS ONE, www.plosone.com, Aug. 2011, vol. 6, Issue 8, e24228.

Aumailley et al., "A simplified laminin nomenclature", Matrix Biology, 24, 2005, 326-332.

Brevini et al., Embryonic Stem Cells in Domestic Animals—No shortcuts to pig embryonic stem cells, Theriogenology, Apr. 2010, vol. 74, 544-550.

Paris et al., Embryonic Stem Cells in Domestic Animals—Equine embryos and embryonic stem cells: Defining reliable markers of pluripotency, Theriogenology, 2010, vol. 74, 516-524.

Munoz et al., Constraints to Progress in Embryonic Stem Cells from Domestic Species, Stem Cell Rev and Rep (2009) 5:6-9.

Lian et al., Directed cardiomyocyte differentiation from human pluripotent stem cells by modulating Wnt/B-catenin signaling under fully defined conditions, Nature Protocols, 2013, vol. 8, No. 1, 162-175.

Gonzalez, Rodolfo et al., Stepwise Chemically Induced Cardiomyocyte Specification of Human Embryonic Stem Cells, 2011, Chem. Int. Ed. Engl. 50, 11181-11185.

Rodin et al., Long-term self-renewal of human pluripotent stem cells on human recombinant laminin-511, Nature Biotechnology, Jun. 2010, vol. 28, No. 6, 611-617.

Gawlik et al., Skeletal muscle laminin and MDC1A: pathogenesis and treatment strategies, Skeletal Muscle, 2011, 1:9, 1-13.

Nishiuchi et al., Ligand-binding specificities of laminin-binding integrins: A comprehensive survey of laminin-integrin interactions using recombinant a3B1, a6B1, a7B1 and a6B4 integrins, Matrix Biology 25, 2006, 189-197.

Yuanqing Tan et al; Generation of clinical-grade functional cardiomyocytes from human embryonic stem cells in chemically defined conditions: Clinical grade cardiomyocytes generated from hESC alongside functional characterization Journal of Tissue Engineering and Regenerative Medicine, Jun. 9, 2017, pp. 153-163, vol. 12, np. 1, Wiley Online Library.

James J.H. Chong et al; Cardiac regeneration using pluripotent stem cells—Progression to large animal models, Stem Cell Research, Nov. 1, 2014, pp. 654-665, vol. 13, No. 3, sciencedirect.com.

Alan Tin-Lun Lam et al; Improved Human Pluripotent Stem Cell Attachment and Spreading on Xeno-Free Laminin-521-Coated Microcarriers Results in Efficient Growth in Agitated Cultures, Bioresearch Open Access, Dec. 1, 2015, pp. 242-257, vol. 4, No. 1, ISSN: 2164-7860.

Denning Chris et al; Cardiomyocytes from human pluripotent stem cells: From laboratory curiosity to industrial biomedical platform, Biochimica Et Biophysica Acta. Molecular Cell Research, Oct. 31, 2015, pp. 1728-1748, vol. 1863, No. 7, Elsevier Science Publishers, Amsterdam, NL.

C. W. Van Den Berg et al; Transcriptome of human foetal heart compared with cardiomyoctes from pluripotent stem cells, Development, Jul. 24, 2015, pp. 3231-3238, vol. 142, No. 18, ISSN: 0950-1991.

International Search Report for PCT Application No. PCT/SG2018/050304 dated Sep. 14, 2018.

Li Yunpeng et al: "Original Article Transplantation of multipotent isi1+ cardiac progenitor cells preserves infarcted heart function in mice," Am J Transl Res, Mar. 30, 2017, pp. 1530-1542, XP055865289.

Menasché Philippe et al: "Human embryonic stem cell-derived cardiac progenitors for severe heart failure treatment: first clinical case report: Figure 1", European Heart Journal, vol. 36, No. 30, Aug. 7, 2015 (Aug. 7, 2015), pp. 2011-2017, XP055865292.

Gonzalez, et al., "Retraction of: Activation of Cardiac Progenitor Cells Reverses the Failing Heart Senescent Phenotype and Prolongs Lifespan", 2018 American Heart Association, Inc., Circ Res. 2019;124:e20, p. 20.

Goichberg, et al., "Retraction of: Age-Associated Defects in EphA2 Signaling Impair the Migration of Human Cardiac Progenitor Cells", 2018 American Heart Association, Inc., Circulation 2019;139:e39, Feb. 12, 2019.

The Lancet Editors, "Retraction—Cardiac Stem Cells in Patients with Ischaemic Cardiomyopathy (SCIPIO): Initial Results of a Randomised Phase 1 Trial", vol. 393, Mar. 16, 2019, p. 1084.

Kajstura, et al., "Retraction of: Cardiomyogenesis in the Adult Human Heart", 2018 American Heart Association, Inc., Circ Res. 2019;124:e22.

Kajstura, et al., Notice of Retraction for "Cardiomyogenesis in the Aging and Failing Human Heart", Circ 2012;126:1869-1881, 2014 American Heart Association, Inc., Circ 2014;129:e466.

Ferreira-Martins, et al., "Retraction of: Cardiomyogenesis in the Developing Heart is Regulated by C-Kit-Positive Cardiac Stem Cells", 2018 American Heart Association, Inc., Circ Res. 2019;124:e28.

Kajstura, et al., "Retraction: Evidence for Human Lung Stem Cells", New England Journal of Medicine 2011;364:1795-806.

D'Amario, et al., "Retraction of: Growth Properties of Cardiac Stem Cells Are a Novel Biomarker of Patient's Outcome After Coronary Bypass Surgery", 2018 American Health Association, Circulation 2019;139:e:40.

Hosoda, et al., "Retraction of: Human Cardiac Stem Cell Differentiation is Regulated by a Mircrine Mechanism", 2018 American Heart Association, Circulation 2019:139:e38.

Bearzi, et al., "Retraction for Identification of a Coronary Vascular Progenitor Cell in the Human Heart", Oct. 9, 2019, vol. 116, No. 41.

D'Amario, et al., "Retraction of: Insulin-Like Growth Factor-1 Receptor Identifies a Pool of Human Cardiac Stem Cells with Superior Therapeutic Potential for Myocardial Regeneration", 2018 American Heart Association, Inc., Circ Res. 2019;124:e26.

Kajstura, et al., "Retraction of: Myocyte Turnover in the Aging Human Heart", 2018 American Heart Association, Inc., Circ Res. 2019;124:e23.

Boni, et al., "Retraction for Notch1 Regulates the Fate of Cardiac Progenitor Cells", PNAS, Oct. 9, 2019, vol. 116, No. 41.

D'Alessandro, et al., "Retraction of: Progenitor Cells From the Explanted Heart Generate Immunocompatible Myocardium Within the Transplanted Donor Heart", 2018 American Heart Association, Inc., Circ Res. 2019;124:e21.

Anversa, et al., "Retraction for Regenerating New Heart with Stem Cells", J Clin Invest. 2013;123(1):62-70.

Leri, et al., "Retraction of: Role of Cardiac Stem Cells in Cardiac Pathophysiology: A Paradigm Shift in Human Myocardial Biology", 2018 American Heart Association, Inc., Circ Res. 2019;124:e24.

Goichberg, et al., "Retraction of: The Ephrin A1-EphA2 System Promotes Cardiac Stem Cell Migration After Infarction", 2018 American Heart Association, Inc., Circ Res. 2019;124:e25.

Kajstura, et al., "Retraction of: Tracking Chromatid Segregation to Identify Human Cardiac Stem Cells That Regenerate Extensively the Infarcted Myocardium", 2018 American Heart Association, Inc., Circ Res. 2019;124:e29.

Gonzalez, et al., Retraction of "Activation of Cardiac Progenitor Cells Reverses the Failing Heart Senescent Phenotype and Prolongs Lifespan", Circulation Research Mar. 14, 2008, 2008 American Heart Association, Inc.

Goichberg, et al., Retraction of "Age-Associated Defects in EphA2 Signaling Impair the Migration of Human Cardiac Progenitor Cells", Circulation 2013;128:2211-2223, 2013 American Heart Association, Inc.

Bolli, et al., Retraction for "Cardiac Stem Cells in Patients with Ischaemic Cardiomyopathy (SCIPIO): Initial Results of a Randomised Phase 1 Trial", Nov. 26, 2011, vol. 378.

Kajstura, et al., Retraction of "Cardiomyogenesis in the Adult Human Heart", 2010 American Heart Association, Inc., Circulation Research Jul. 23, 2010.

Kajstura, et al., Retraction of "Cardiomyogenesis in the Aging and Failing Human Heart", 2012 American Heart Association, Inc., Circulation Oct. 9, 2012.

(56) References Cited

OTHER PUBLICATIONS

Ferreira-Martins, et al., Retraction of "Cardiomyogenesis in the Developing Heart is Regulated by C-Kit-Positive Cardiac Stem Cells", 2012 American Heart Association, Inc., Circulation Research Mar. 2, 2012.

Kajstura, et al., Retraction of "Evidence for Human Lung Stem Cells", The New England Journal of Medicine, vol. 364, No. 19, May 12, 2011.

D'Amario, et al., Retraction of "Growth Properties of Cardiac Stem Cells are a Novel Biomarker of Patients' Outcome After Coronary Bypass Surgery", 2013 American Heart Association, Inc., Circulation Jan. 14, 2014.

Kolata, "He Promised to Restore Damaged Hearts. Harvard Says His Lab Fabricated Research", The New York Times, Oct. 29, 2018.

Hosoda, et al., Retraction for "Human Cardiac Stem Cell Differentiation is Regulated by a Mircrine Mechanism", 2015 American Heart Association, Inc., Circulation Mar. 29, 2011.

Bearzi, et al., Retraction for "Identification of a Coronary Vascular Progenitor Cell in the Human Heart", PNAS, vol. 106, No. 37, Sep. 15, 2019.

D'Amario, et al., Retraction for "Insulin-Like Growth Factor-1 Receptor Identifies a Pool of Human Cardiac Stem Cells With Superior Therapeutic Potential for Myocardial Regeneration", 2011 American Heart Association, Inc., Circulation Research Jun. 10, 2011.

Kajstura, et al., Retraction of "Myocyte Turnover in the Aging Human Heart", 2010 American Heart Association, Inc., Circulation Research Nov. 26, 2010.

Boni, et al., Retraction for "Notch1 regulates the Fate of Cardiac Progenitor Cells", PNAS, vol. 116, No. 41, Oct. 8, 2019.

D'Alessandro, et al., "Progenitor Cells From the Explanted Heart Generate Immunocompatible Myocardium Within the Transplanted Donor Heart", 2009 American Heart Association, Inc., Circulation Research Nov. 20, 2009.

Anversa, et al., "Regenerating New Heart with Stem Cells". The Journal of Clinical Investigation 2013;123(1):62-70, vol. 123, No. 1, Jan. 2013.

Leri, et al., Retraction of "Role of Cardiac Stem Cells in Cardiac Pathophysiology: A Paradigm Shift in Human Myocardial Biology", 2011 American Heart Association, Inc., Circulation Research Sep. 30, 2011.

Goichberg, et al., Retraction of "The Ephrin A1-EphA2 System Promotes Cardiac Stem Cell Migration After Infarction", 2011 American Heart Association, Inc., Circulation Research Apr. 29, 2011.

Kajstura, et al., Retraction of "Tracking Chromatid Segregation to Identify Human Cardiac Stem Cells That Regenerate Extensively the Infarcted Myocardium", 2012 American Heart Association, Inc., Circulation Research Sep. 14, 2012.

Hans Reinecke, et al., "Cardiogenic Differentiation and Transdifferentiation of Progenitor Cells" NH Public Access Published Nov. 2008.

P. Van Vilet, et al., "Progenitor Cells isolated from the human heart: a potential cell source for regenerative therapy" Netherlands Heart Journal vol. 16, No. 5, May 2008.

P. Van Vilet, et al., "Human cardiomyocyte progenitor cells: a short history of nearly everything" Cardiomyocyte and Regeneration Review Series J. Cell. Mol. vol. 16, No. 8, 2012.

Shengwen, Calvin Li, et al., "Mechanisms for progenitor Cell-Mediated Repair for Ischemic Heart Injury" HHS Public Access Curr Stem Cell Res. Ther. Jan. 2012.

Simpson, David L., et al., "A Strong Regenerative Ability of Cardiac Stem Cells Derived From Neonatal Hearts" HHS Public Access, Circulation, Sep. 2012.

Donghui Jing, B.S., et al., "Stem Cells for Heart Cell Therapies" Tissue Engineering: Part B, vol. 14, No. 4, 2008.

* cited by examiner

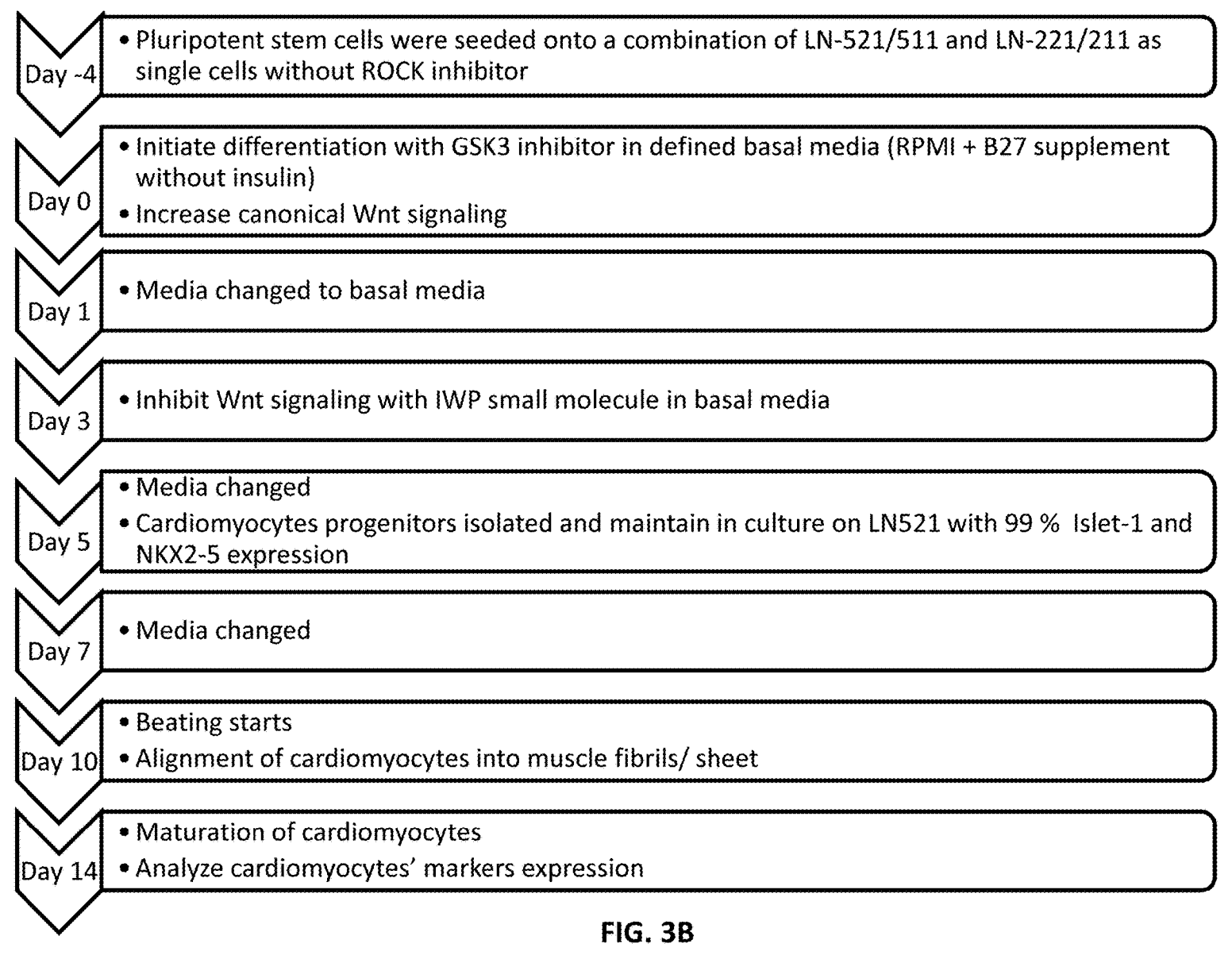

Day ~4
- Pluripotent stem cells were seeded onto a combination of LN-521/511 and LN-221/211 as single cells without ROCK inhibitor

Day 0
- Initiate differentiation with GSK3 inhibitor in defined basal media (RPMI + B27 supplement without insulin)
- Increase canonical Wnt signaling

Day 1
- Media changed to basal media

Day 3
- Inhibit Wnt signaling with IWP small molecule in basal media

Day 5
- Media changed
- Cardiomyocytes progenitors isolated and maintain in culture on LN521 with 99 % Islet-1 and NKX2-5 expression

Day 7
- Media changed

Day 10
- Beating starts
- Alignment of cardiomyocytes into muscle fibrils/ sheet

Day 14
- Maturation of cardiomyocytes
- Analyze cardiomyocytes' markers expression

FIG. 3B

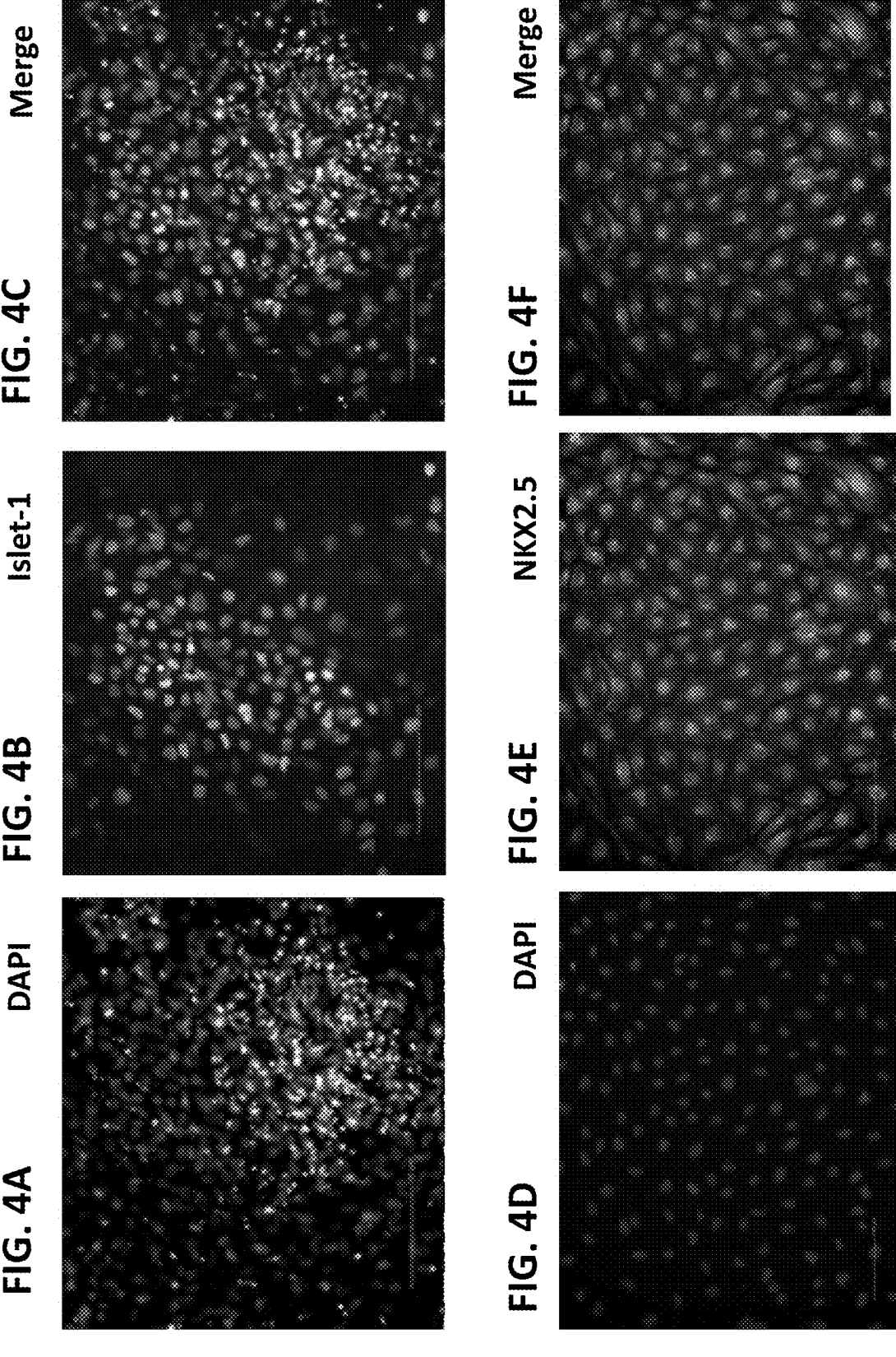

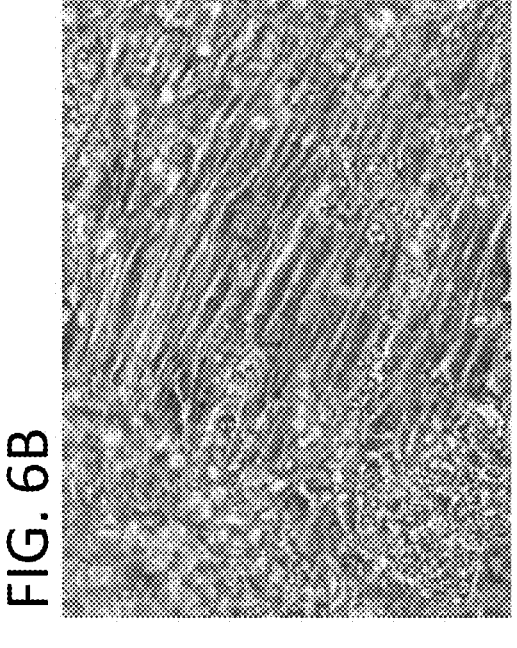
FIG. 6B
FIG. 6A
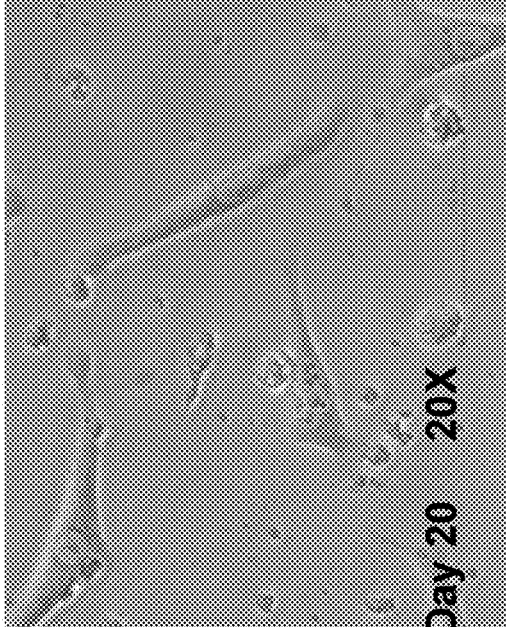
FIG. 6C

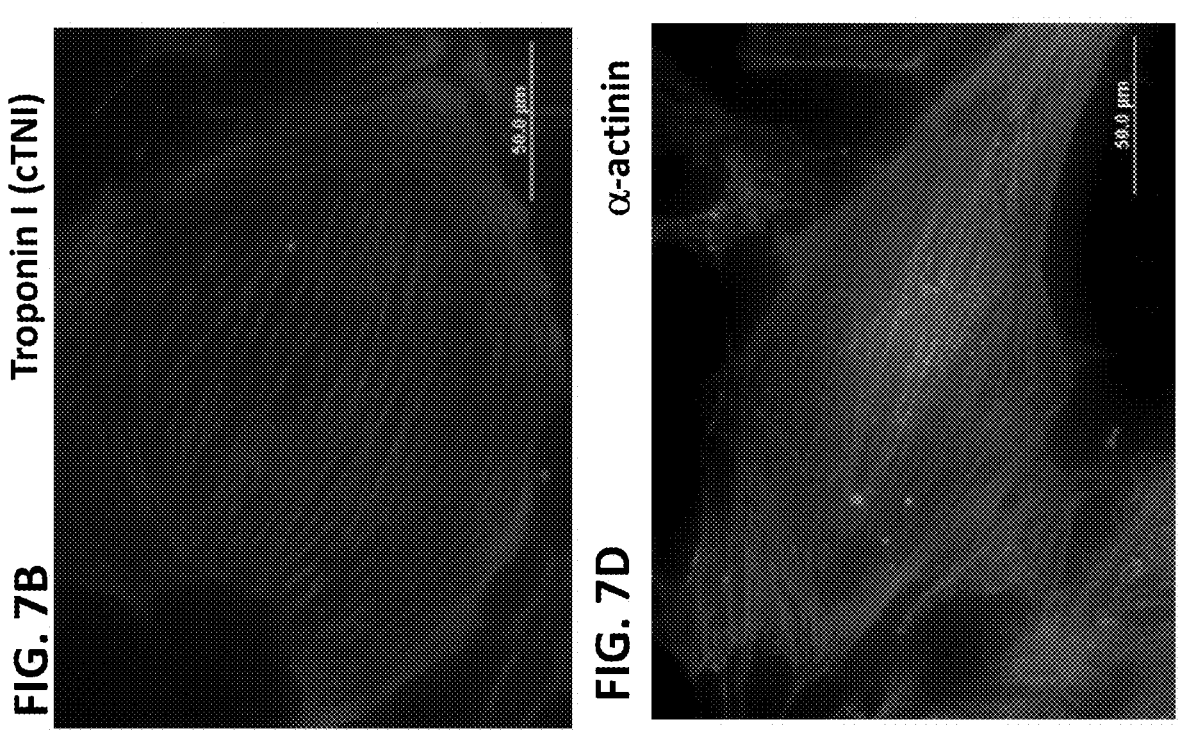
FIG. 7B    Troponin I (cTNI)
FIG. 7D    α-actinin
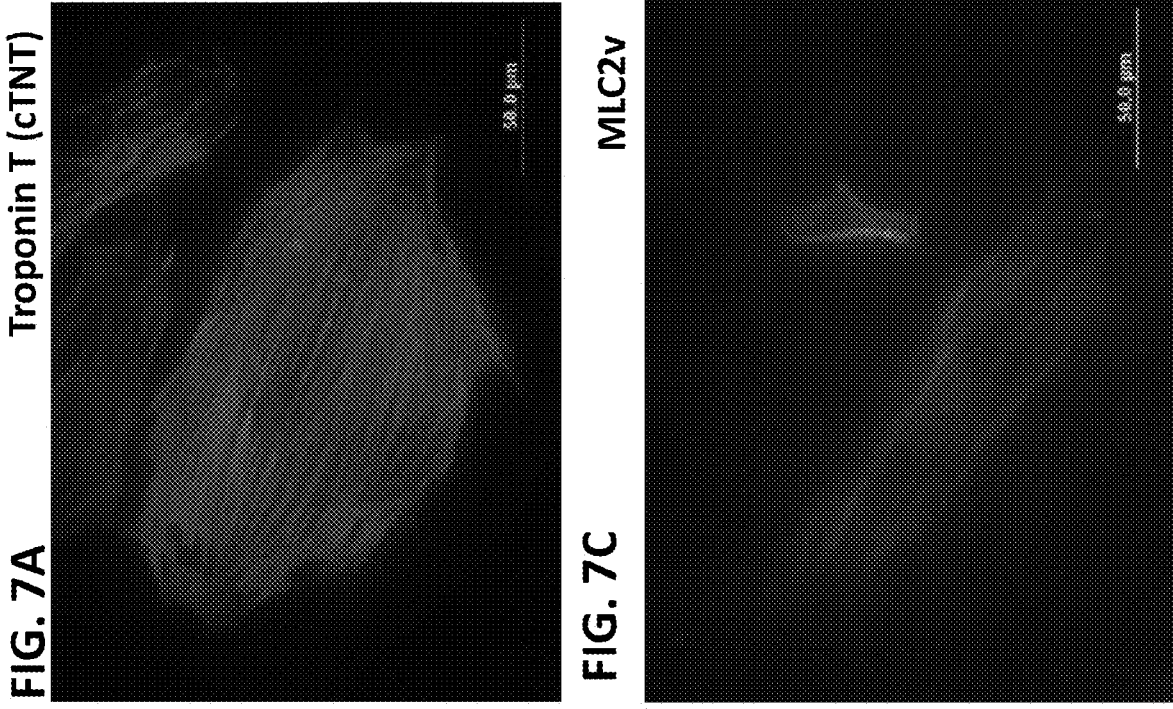
FIG. 7A    Troponin T (cTNT)
FIG. 7C    MLC2v Progenitors
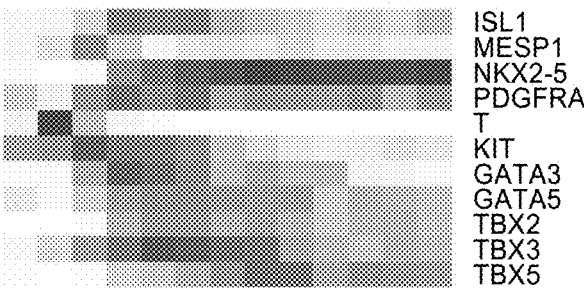
Cardiomyocytes
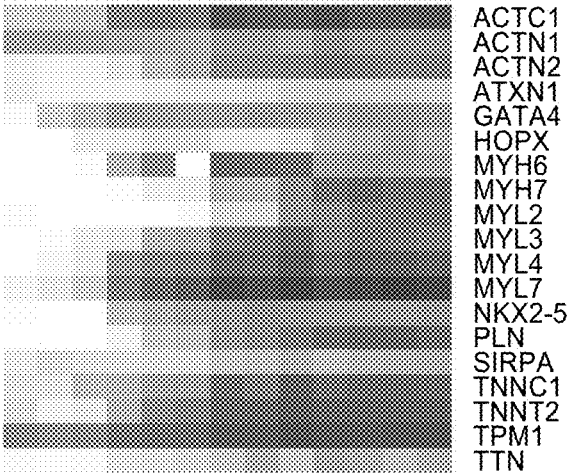
Channels / Ion Transporter
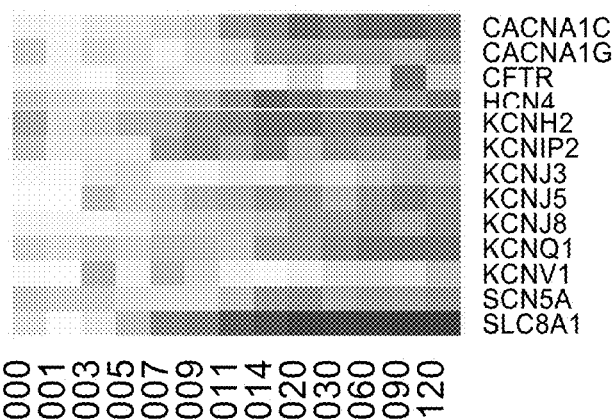
FIG. 11A

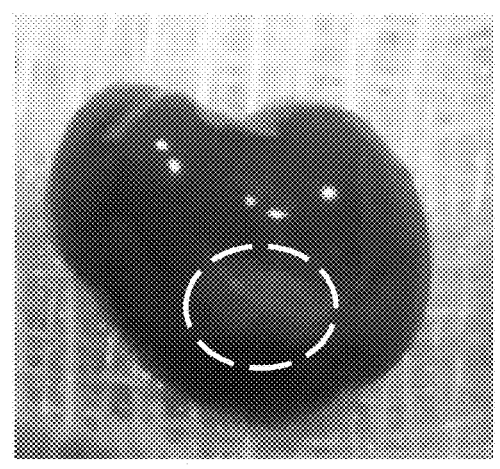 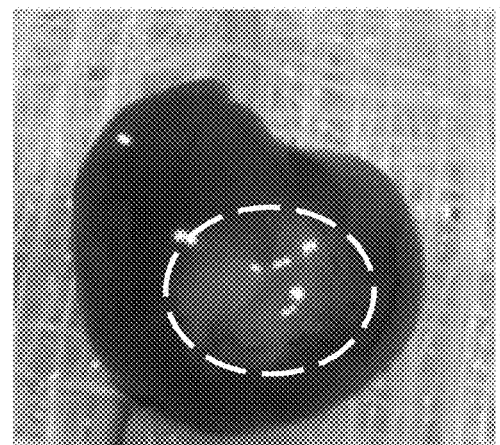
D5 progenitors                    Medium
FIG. 13A
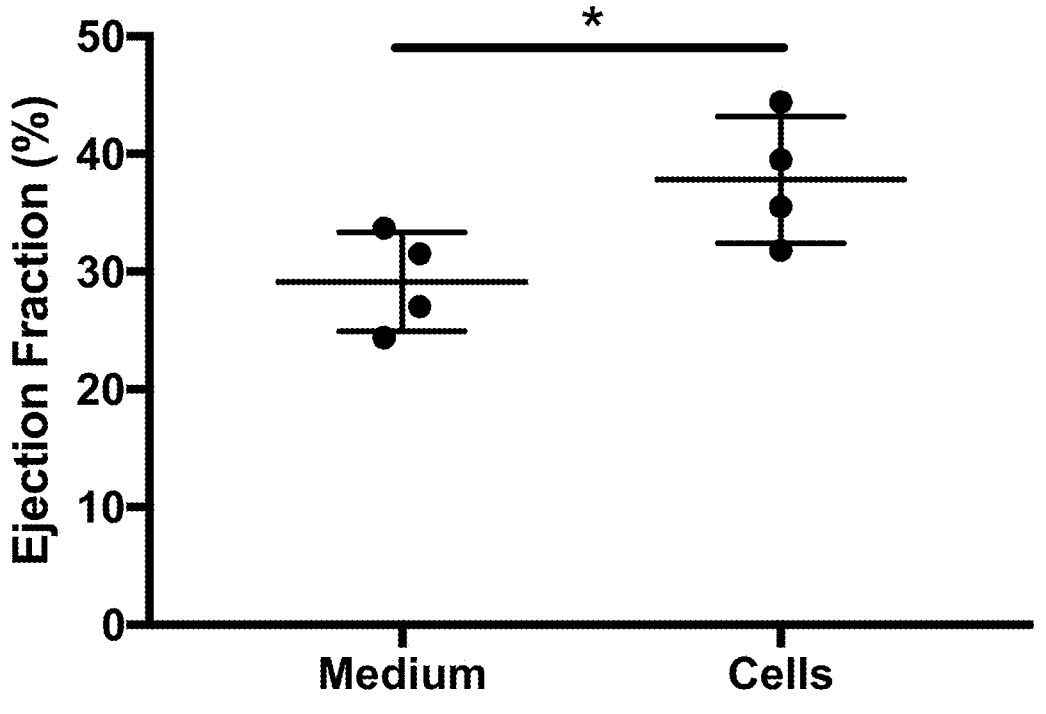
FIG. 13B

1

DIFFERENTIATION OF PLURIPOTENT STEM CELLS AND CARDIAC PROGENITOR CELLS INTO STRIATED CARDIOMYOCYTE FIBERS USING LAMININS LN-511, LN-521 AND LN-221

CROSS-REFERENCE TO RELATED APPLICATIONS

This application claims priority to U.S. Provisional Patent Application Ser. No. 62/523,700, filed Jun. 22, 2017; and is also a continuation-in-part of U.S. patent application Ser. No. 14/895,669, filed Dec. 3, 2015, which is a 371 of PCT Application No. PCT/IB2014/002289, filed Jul. 2, 2014, which claims priority to U.S. Provisional Patent Application Ser. No. 61/842,241, filed Jul. 2, 2013, the entirety of these disclosures being fully incorporated by reference herein.

BACKGROUND

The present disclosure relates to methods for generating cardiomyocyte progenitors and cardiomyocytes from pluripotent stem cells using laminin substrates. It finds particular application in the differentiation of cardiomyocytes from pluripotent stem cells using (1) laminin-521 or laminin-511, and (2) laminin-221 or laminin-211. The method allows for a controllable and highly reproducible generation of cardiomyocyte progenitor cells and differentiated cardiomyocytes for various applications including regenerative cardiology and testing for drug effects and cardiotoxicity.

A stem cell is an undifferentiated cell from which specialized cells are subsequently derived. Examples of stem cells in the human body include pluripotent stem cells, embryonic stem cells, adult stem cells, fetal stem cells, and amniotic stem cells. Embryonic stem cells possess extensive self-renewal capacity and pluripotency with the potential to differentiate into cells of all three germ layers. Also, induced pluripotent stem (iPS) cells generated from differentiated cells with the help of specific transcription factors are also pluripotent.

Totipotency refers to a cell that has the ability to differentiate into any cell in the body, including extraembryonic tissue. Pluripotency refers to a cell that has the potential to differentiate into cells of all three germ layers. Pluripotent cells however cannot form extraembryonic tissue, as a totipotent cell can. Multipotency refers to a cell that can differentiate into cells of limited lineage. For example, a hematopoietic stem cell can differentiate into several types of blood cells, but cannot differentiate into a brain cell.

The process by which a stem cell changes into a more specialized cell is referred to as differentiation. For example, some differentiated cells include heart cardiomyocyte cells, which are derived from pluripotent human embryonic stem cells (hESCs). The process by which a specialized cell reverts back to a higher degree of potency (i.e. to an earlier developmental stage) is referred to as dedifferentiation. In particular, cells in a cell culture can lose properties they originally had, such as protein expression or shape, after undergoing the dedifferentiation process. A differentiated cardiomyocyte cell, for example, may lose its cellular phenotype, specialized characteristics, or ability to be transplanted to the heart region after the dedifferentiation process.

Cell therapy based regenerative medicine using differentiated cells holds promise as a treatment for a variety of tissue injuries. Examples of potential disease targets for cell therapy include cardiac injuries (e.g. myocardial infarction), type I diabetes (destruction of insulin producing beta cells) and Parkinson's disease (lack of dopamine producing neurons). A prerequisite for generating cells for such therapy is a possibility to differentiate the cells to specific cell types with defined reproducible protocols and obtain large quantities of human cells with stable differentiated cellular phenotypes that are suitable for transplantation to the site of injury.

There is also an urgent need for new, innovative and human-predictive cell assays within the global pharmaceutical industry since drug discovery issues, such as toxicity and lack of efficacy, are leading causes for drug failure/attrition during the pre-clinical as well as clinical stage. Currently used cell systems are not sufficient due to a number of limitations. One significant limitation is that differentiated cells often dedifferentiate in in vitro cell cultures. Moreover, many human primary cell types needed for drug discovery, like cardiomyocytes and neuronal cells, are for various reasons almost inaccessible.

BRIEF DESCRIPTION

The present disclosure relates to the development and expansion of heart progenitor cells and mature cardiomyocytes by maintaining pluripotent human embryonic stem cells on a combination of (A) embryonic laminin LN-521 or LN-511, together with (B) either the most abundant and highly heart muscle specific laminin, LN-221, or with LN-211. This new type of differentiation protocol provides completely chemically defined and animal reagent-free conditions that are a prerequisite for use of such cells for pharmaceutical development or as the direct use in human cell therapies. Disclosed herein are methods for generating cardiomyocyte progenitor cells and mature cardiomyocytes through differentiation of pluripotent stem cells on cell culture substrates including particular laminins.

In some embodiments, methods for differentiating cardiomyocyte cells from a pluripotent stem cell comprise maintaining a pluripotent stem cell onto a cell culture substrate including LN-521 or LN-511, seeding the pluripotent stem cell onto a substrate including (i) LN-521 or LN-511 and (ii) LN-221 or LN-211, and culturing the pluripotent stem cells in a basal medium to form cardiomyocyte progenitor cells. The basal medium does not contain any inhibitors of apoptosis.

The methods may include differentiating the cardiomyocyte progenitor cells on the substrate to form mature cardiomyocyte cells.

The methods may also include culturing the pluripotent stem cells in the presence of a GSK-3 inhibitor to stimulate Wnt signaling.

The methods may include culturing the pluripotent stem cells in the basal medium devoid of inhibitors.

The methods may also include transforming the mature cardiomyocyte cells into contracting (beating) aggregated muscle fibers.

The methods may include clustering the pluripotent stem cells in the presence of Wnt inhibitor to suppress Wnt signaling.

The methods may also include a cell culture coating where at least one of LN-521, LN-511, LN-221, and LN-211 is an effective recombinant laminin or a fragment thereof.

The methods may include a cell culture substrate and combination cell culture substrate without any differentiation inhibitors, feeder cells, differentiation inductors, or apoptosis inhibitors.

The methods may further include applying a cell culture medium to the pluripotent stem cells.

The methods may also include cardiomyoctye progenitor cells which express Islet-1, NKX2.5, as well as other transcription factors.

The methods may further include the aggregated muscle fibers and beating cell sheets expressing Troponin T, myosin light chain for ventricular cells (MLC2v), and myosin sarcomere filament (MF-20) biomarkers.

In other embodiments, a progenitor cardiomyocyte cell is formed from the differentiation of pluripotent stem cells on a combination cell culture substrate including at least one of (i) LN-511 and LN-521, and (ii) LN-221 or LN-211.

The progenitor cardiomyocyte cell may express Islet-1 and NKX2.5 transcription factor.

In some embodiments, a mature cardiomyocyte cell is formed from the differentiation of pluripotent stem cells on a combination cell culture substrate including (i) at least one of LN-511 and LN-521, and (ii) LN-221 or LN-211.

The mature cardiomyocyte cell may form a single muscle fiber or multiple fibers, forming a beating cell sheet expressing Troponin T, myosin light chain for ventricular cells (MLC2v), and myosin sarcomere filament (MF-20) biomarkers.

The muscle fiber may have a beating, striated phenotype.

In other embodiments, methods for forming a heart muscle fiber with a beating striated phenotype may include differentiating pluripotent stem cells on a substrate including (i) LN-521 or LN-511 and (ii) LN-221 or LN-211, to form mature cardiomyocyte cells, and transforming the mature cardiomyocyte cells into a cardiomyocyte-like heart muscle fiber having a beating, striated phenotype.

In some methods, the pluripotent stem cell is a human embryonic stem cell (hESC). In other embodiments, a heart muscle fiber having a beating, striated phenotype is generated by the differentiation of pluripotent stem cells on a cell culture combination substrate including (i) LN-521 or LN-511 and (ii) LN-221 or LN-211.

The heart muscle fiber may be generated by the differentiation of a human embryonic stem cell (hHSC) or a human induced pluripotent stem cell (hiPSC).

Also disclosed herein are the cells and muscle fibers created using the methods described herein.

Also disclosed are methods for treating an injured heart, comprising: injecting cardiomyocyte progenitor cells into the injured heart.

Also disclosed are methods for regenerating damaged heart muscle, comprising: injecting cardiomyocyte progenitor cells into the damaged heart muscle.

The cardiomyocyte progenitor cells can be obtained by differentiating embryonic stem cells using a chemically-defined and xeno-free protocol. Alternatively, the cardiomyocyte progenitor cells can be obtained by: seeding pluripotent stem cells onto a substrate including (i) LN-521 or LN-511 and (ii) LN-221 or LN-211; and culturing the pluripotent stem cells to form the cardiomyocyte progenitor cells.

The pluripotent stem cells can be cultured by: culturing the pluripotent stem cells in the presence of a GSK-3 inhibitor to stimulate Wnt signaling for a first time period; culturing the pluripotent stem cells in a cell culture medium devoid of inhibitors for a second time period; and culturing the pluripotent stem cells in the presence of Wnt inhibitor to suppress Wnt signaling for a third time period. The cardiomyocyte progenitor cells can be obtained by the fifth day after the beginning of differentiation.

In particular embodiments, the first time period, second time period, and third time period are each independently from about 12 hours to about 48 hours.

Also disclosed are cardiomyocyte progenitor cell formed from the differentiation of pluripotent stem cells on a combination cell culture substrate including (i) one of LN-511 and LN-521, and (ii) LN-221 or LN-211, and using a chemically-defined and xeno-free cell culture medium. The pluripotent stem cells may be human embryonic stem cells (hESCs).

Also disclosed herein are cardiomyocyte progenitor cells, wherein a Day 5 differential transcriptome of the cardiomyocyte progenitor cell indicates that: (A) at least one of genes TTR, PLAT, TBX5, APOA2, APOA1, AC132217.4, NKX2-5, MYL7, GATA6-AS1, BST2, FLRT3, MYL4, and ENO3 are up-regulated by a log2 fold change value of at least 1; or (B) at least one of genes DCLK1, RP11-6918.2, ZIC3, T, RXRG, and CTD-2311M21.2 are down-regulated by a log2 fold change value of at least −0.5. Other combinations of these genes are disclosed herein.

In still other embodiments, (A) at least one of genes TTR, APOA1, AC132217.4, MYL4, and FLRT3 is up-regulated by a log2 fold change value of at least 2; or (B) at least one of genes RXRG and T are down-regulated by a log2 fold change value of at least −2.

In some specific embodiments, (A) at least one of genes TTR and APOA1 is up-regulated by a log2 fold change value of at least 2; and (B) gene RXRG is down-regulated by a log2 fold change value of at least −2.

Also disclosed are cardiomyocyte progenitor cells, wherein a Day 7 differential transcriptome of the cardiomyocyte progenitor cell indicates that: (A) at least one of genes MYH6, CRHBP, ACTN2, SLC8A1, TNNT2, ACTC1, TNNI1, ANKRD1, MYL7, DLK1, and MYL4 is up-regulated by a log2 fold change value of at least 1; or (B) at least one of genes FGF2, ZIC2, RP11-256I9.2, LGR5, PLP1, and LINC00458 is down-regulated by a log2 fold change value of at least −0.2. Other combinations of these genes are disclosed herein.

In some particular embodiments, (A) at least one of genes MYH6, CRHBP, TNNT2, ACTC1, and ANKRD1 is up-regulated by a log2 fold change value of at least 1; or (B) at least one of genes LGR5 and PLP1 is down-regulated by a log2 fold change value of at least −0.2.

In more particular embodiments, (A) at least one of genes CRHBP and MYH6 is up-regulated by a log2 fold change value of at least 1; and (B) at least one of genes LGR5 and PLP1 is down-regulated by a log2 fold change value of at least −0.2.

Also disclosed are methods for identifying functional cardiomyocyte progenitor cells, comprising: producing a Day 3 transcriptome of the cardiomyocyte progenitor cells after 3 days of differentiation; producing a Day 5 transcriptome of the cardiomyocyte progenitor cells after 5 days of differentiation; preparing a Day 5 differential transcriptome by calculating a log2 fold change value for each gene based on the Day 3 transcriptome and the Day 5 transcriptome; and identifying the cardiomyocyte progenitor cells as functional if: (A) at least one of genes TTR, PLAT, TBX5, APOA2, APOA1, AC132217.4, NKX2-5, MYL7, GATA6-AS1, BST2, FLRT3, MYL4, and ENO3 are up-regulated by a log2 fold change value of at least 1; or (B) at least one of genes DCLK1, RP11-6918.2, ZIC3, T, RXRG, and CTD-2311M21.2 are down-regulated by a log2 fold change value of at least −0.5.

Also disclosed are methods for identifying functional cardiomyocyte progenitor cells, comprising: producing a Day 5 transcriptome of the cardiomyocyte progenitor cells after 5 days of differentiation; producing a Day 7 transcriptome of the cardiomyocyte progenitor cells after 7 days of differentiation; preparing a Day 7 differential transcriptome by calculating a log2 fold change value for each gene based on the Day 5 transcriptome and the Day 7 transcriptome; and identifying the cardiomyocyte progenitor cells as functional if: (A) at least one of genes MYH6, CRHBP, ACTN2, SLC8A1, TNNT2, ACTC1, TNNI1, ANKRD1, MYL7, DLK1, and MYL4 is up-regulated by a log2 fold change value of at least 1; or (B) at least one of genes FGF2, ZIC2, RP11-256I9.2, LGR5, PLP1, and LINC00458 is down-regulated by a log2 fold change value of at least −0.2.

Also disclosed are the cardiomyocyte progenitor cells identified by the methods described above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIGS. 3A-3C include flow diagrams illustrating methods of differentiating cardiomyocytes from pluripotent stem cells. FIG. 3A includes a high level summary of method steps according to one embodiment of differentiating hES cells to beating cardiomyocytes including an indication of which pluripotency markers should be expressed on different days. FIG. 3B includes a day-by-day illustration of steps which correspond with a method of differentiating pluripotent stem cells to beating cardiomyocytes. FIG. 3C includes a detailed illustration of method steps according to another embodiment of differentiating cardiomyocytes.

FIGS. 4A-4F include photomicrographs and flow cytometry analysis of cardiac progenitor cells. FIG. 4A details the expression of DAPI for nuclei. FIG. 4B details Islet-1 transcription factor (red). FIG. 4C details a merger of DAPI and Islet-1 transcription factor expression in cardiomyocyte progenitor cells derived from hESCs. FIG. 4D details the expression of DAPI for nuclei. FIG. 4E details NKX2.5 transcription factor and in FIG. 4F a merger of DAPI and NKX2.5 transcription factor expression in cardiomyocyte progenitor cells derived from hESCs. FIGS. 4A-4F show that Islet-1 and NKX2.5 expression is located in the nucleus of the cells, which strongly suggests the presence of cardiomyocyte progenitors.

FIG. 5A is the analysis by phenotype, where defined colonies were formed when the cells were maintained on LN-521. FIG. 5B is a flow cytometry analysis. The NKX2.5 measurements are labeled with triangles, the Islet-1 measurements are labeled with diamonds, and the isotype control is labeled with circles. In FIG. 5C, progenitors analyzed with Islet-1 and NKX2-5 antibody measured >99% positivity for both markers. The NKX2.5 measurements are labeled with circles, the Islet-1 measurements are labeled with triangles, and the isotype control is labeled with diamonds. In both graphs, the y-axis is the number of cells expressing a certain level of APC-A, which is indicated on the x-axis.

FIG. 6A and FIG. 6B are photomicrographs of cardiomyocyte-like human heart muscle fibers aligned with each other length-wise into muscle fibrils. FIG. 6C is an image of single cardiomyocytes having rectangular morphology.

FIGS. 7A-7D include photomicrographs showing the expression of FIG. 7A cardiac troponin T (cTNT) (green), FIG. 7B cardiac troponin I (cTNI) (green), FIG. 7C myosin light chain for ventricular cells (MLC2v) (green), and FIG. 7D alpha-actinin (α-actinin) (green) biomarkers in the cardiomyocyte of FIG. 6B. Aligned sarcomere organization was observed from these staining. Nuclei were stained with DAPI.

FIG. 8A shows the analysis for cardiac troponin T (cTNT). FIG. 8B shows the analysis for cardiac myosine sacromeric protein (MF20). In these two graphs, the y-axis is the number of cells expressing a certain level of the protein (indicated on the x-axis). The line indicated by circles is for the protein, while the line indicated by diamonds is the isotype control. In FIG. 8A, 82.2% of cells are positive for cTNT, and 17.8% of cells are negative for cTNT. In FIG. 8B, 86.8% of cells are positive for MF20. Both analyses were >80% positive. FIG. 8C shows electrophysiology analysis by patch clamp recording revealed action potential from all 3 subtypes of cardiomyoctes in the heart namely ventricular-like, nodal-like and atrial-like cells.

FIG. 9A shows decreased expression of pluripotent genes to negligible levels after 30 days. FIG. 9B shows temporal expression of progenitor specific genes indicative of mesodermal lineage specification and cardiomyocyte specialization. FIG. 9C shows increased expression of cardiomyocyte specific genes after day 9.

FIG. 11A is a set of genetic expression profiles for progenitors, cardiomyocytes, and channel/ion transporter genes.

Figure 11B:
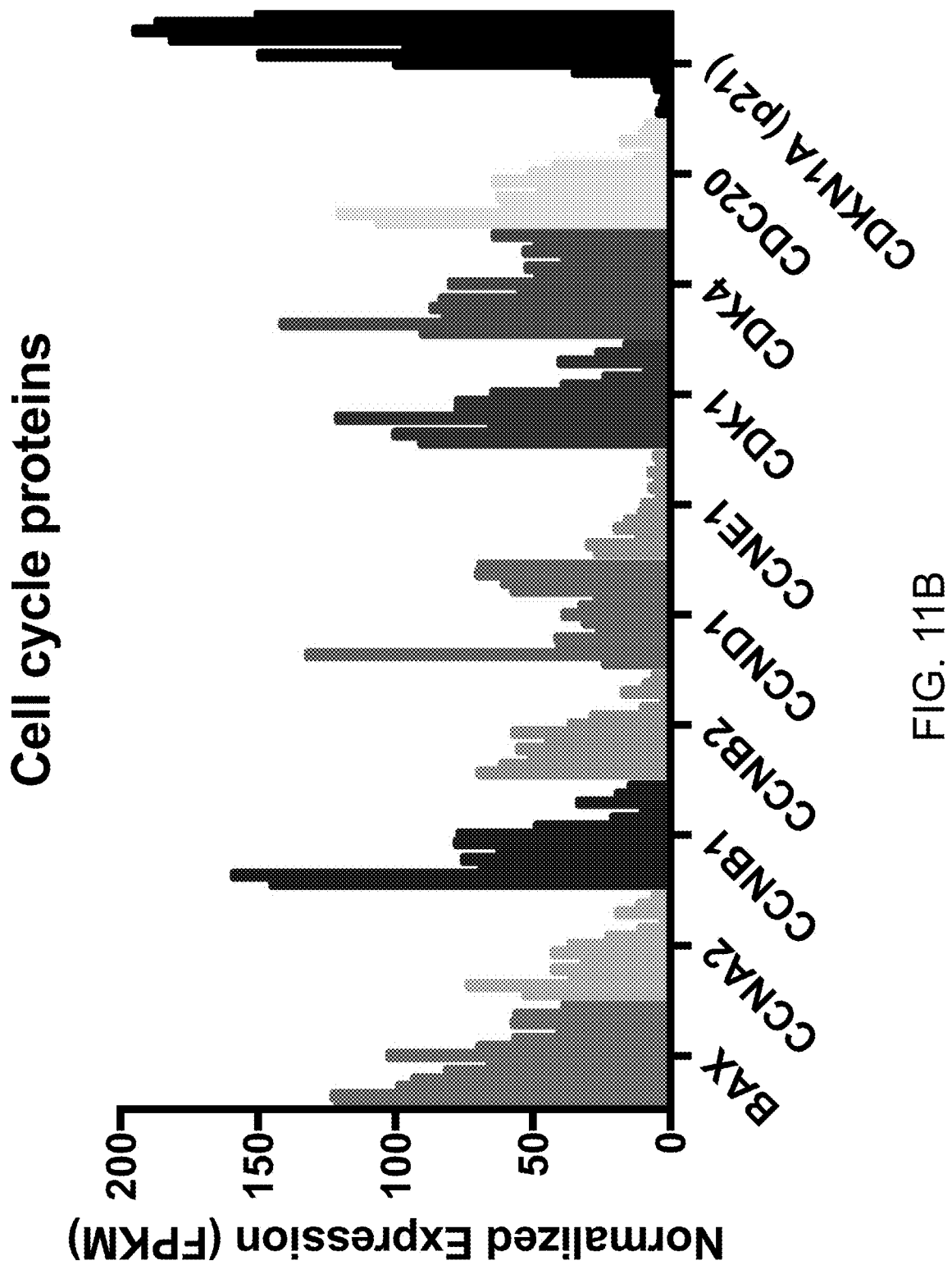

FIG. 11B is a graph showing the expression of certain cell cycle proteins over time. For each protein, time is along the x-axis.

Figure 11C:
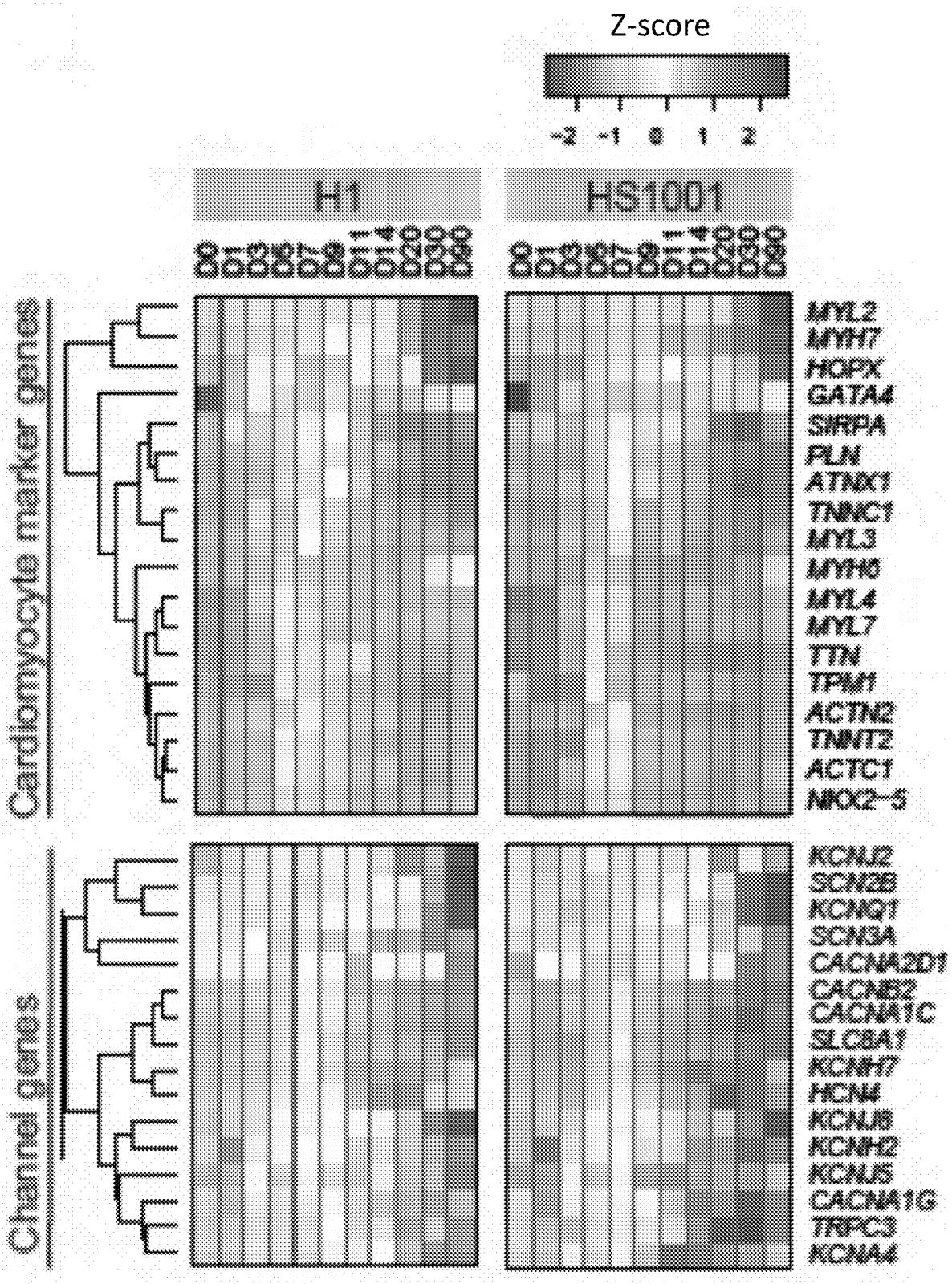

FIG. 11C is another genetic expression profile for progenitors and cardiomyocytes for both H1 and HS1001 lines. The Z-score at the top right runs from −2 to +2 in increments of 1. The x-axis for both lines reads, running from left to right, D0, D1, D3, D5, D7, D9, D11, D14, D20, D30, and D90. The list of genes on the y-axis (right-hand-side) reads, from top to bottom, MYL2, MYH7, HOPX, GATA4, SIRPA, PLN, ATNX1, TNNC1, MYL3, MYH5, MYL4, MYL7, TTN, TPM1, ACTN2, TNNT2, ACTC1, NKX2-5, KCNJ2, SCN2B, KCNQ1, SCN3A, CACNA2D1, CACNB2, CACNA1C, SLC8A1, KCNH7, HCN4, KCNJ8, KCNH2, KCNJ5, CACNA1G, TRPC3, and KCNA4.

Figure 12A:
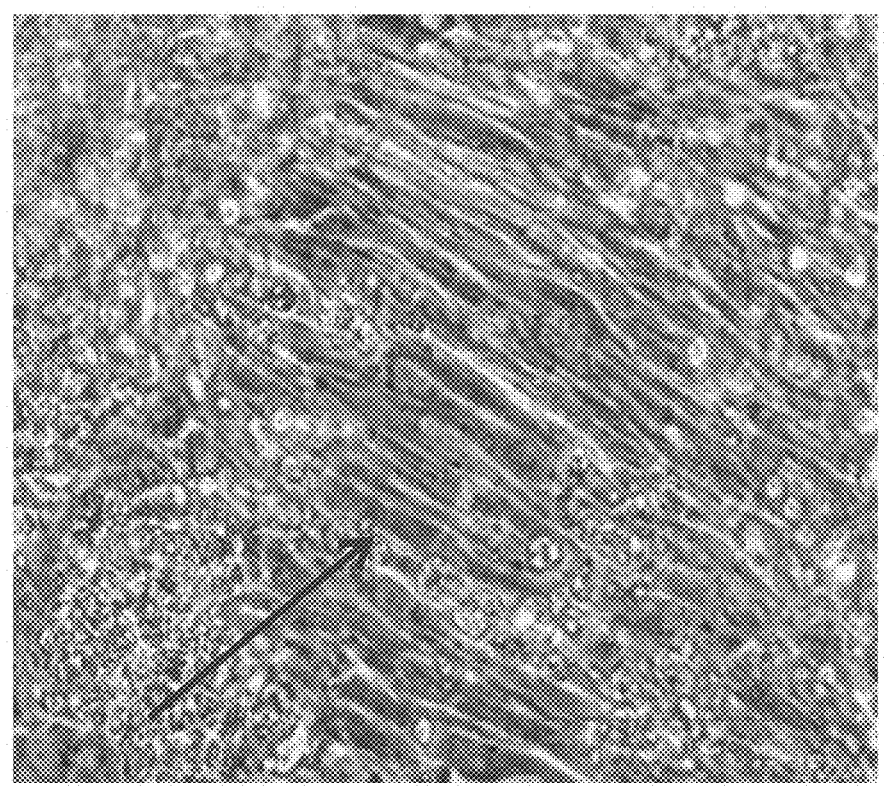

FIG. 12A is a picture showing sheets of aligned beating cardiomyocytes at Day 30.

Figure 12B:
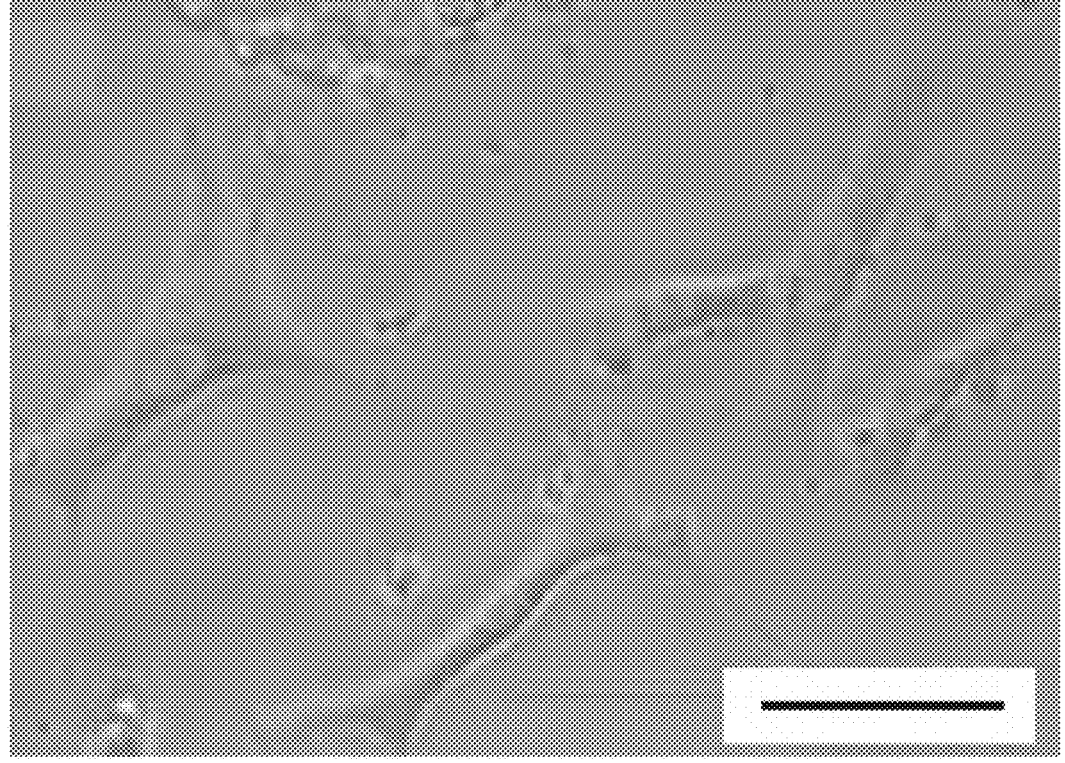

FIG. 12B is a slide showing dissociated single cardiomyocytes at day 30, exhibiting cuboidal morphology. The scale bar is 100 micrometers (μm).

FIGS. 12C-12F are immunofluorescent stains.

Figure 12C:
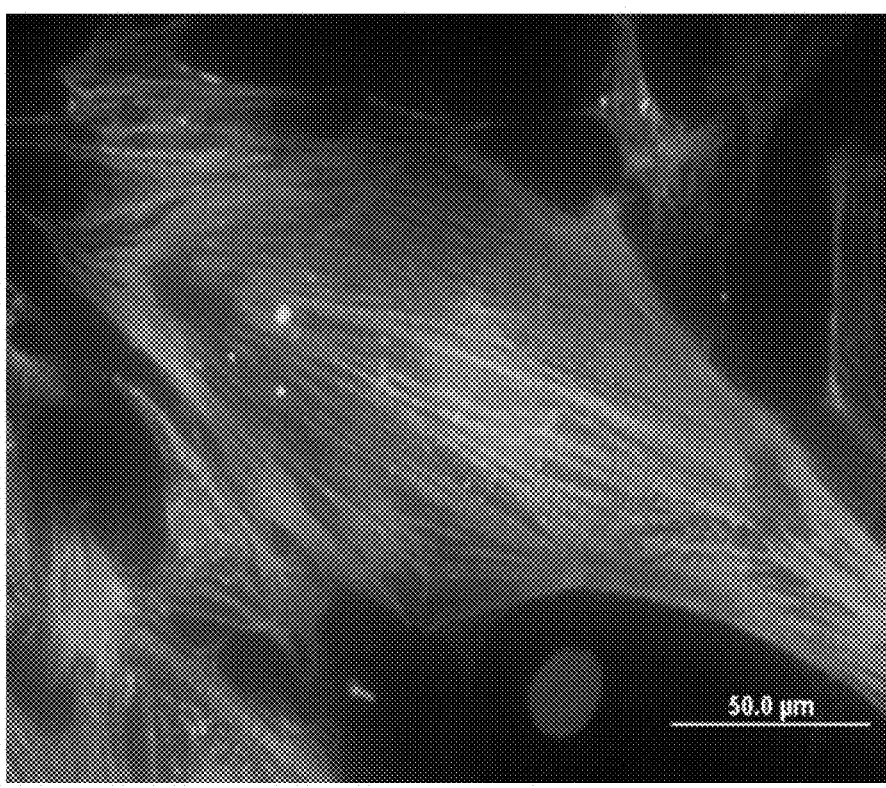

FIG. 12C was stained with α-actinin (green) and TNNI3 (red) antibodies. The scale bar is 50 μm.

Figure 12D:
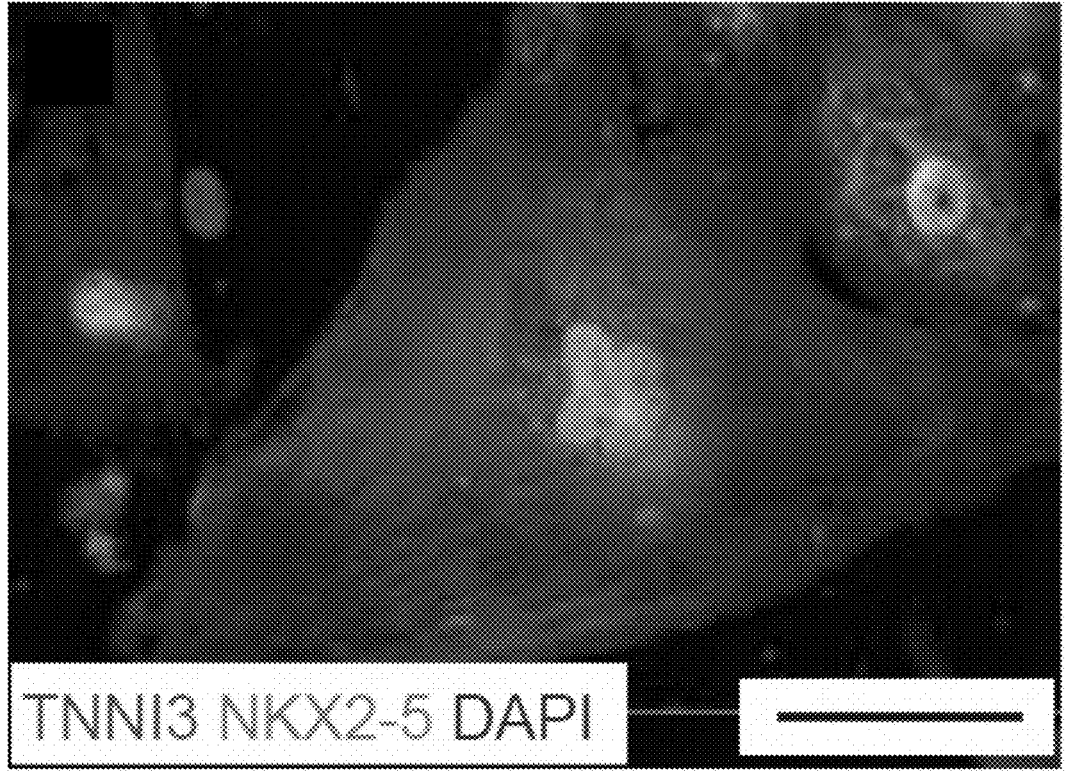

FIG. 12D was stained with NKX2-5 (green) and TNNI3 (red) antibodies, and with DAPI (purple). The scale bar is 100 μm.

Figure 12E:
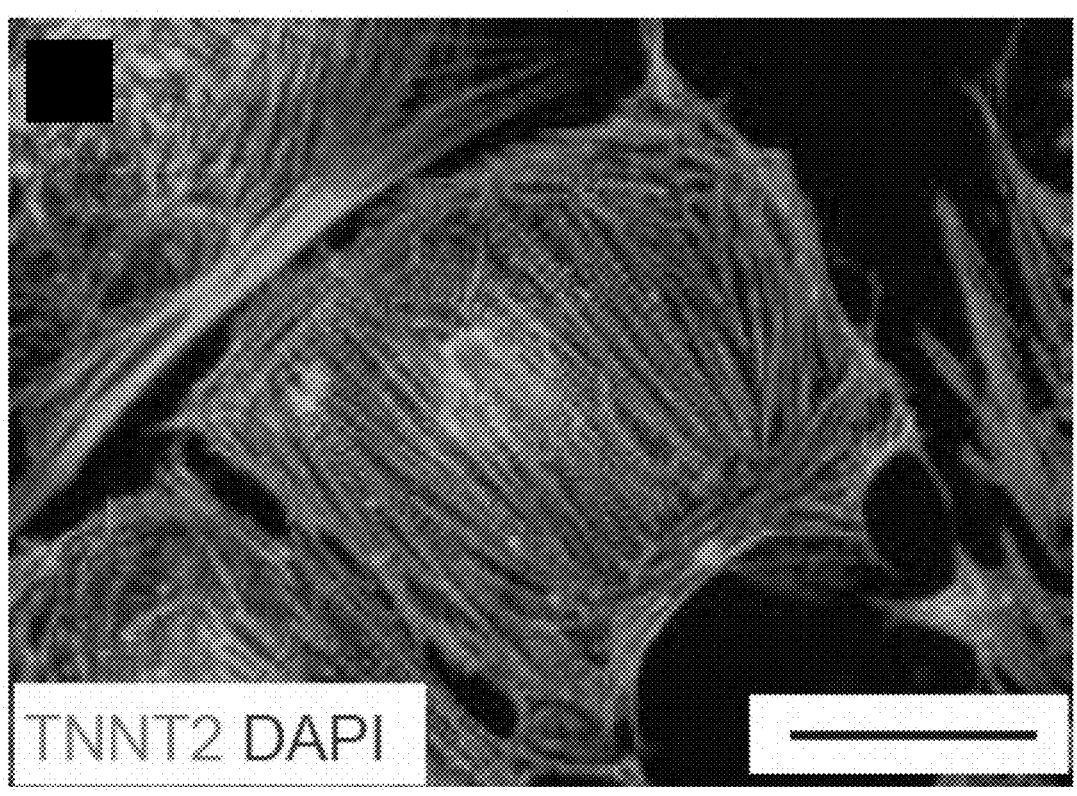

FIG. 12E was stained with TNNT2 antibodies (green) and with DAPI (purple). The scale bar is 100 μm.

Figure 12F:
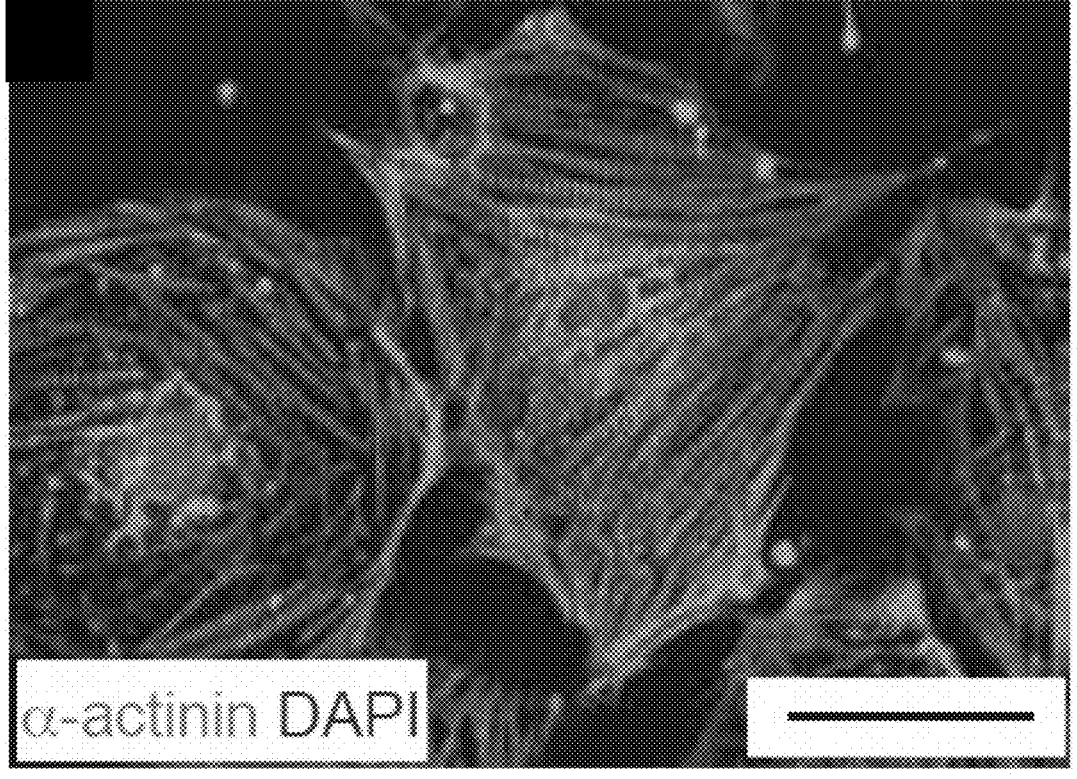

FIG. 12F was stained with α-actinin antibodies and with DAPI. The scale bar is 100 μm.

Figure 12G:
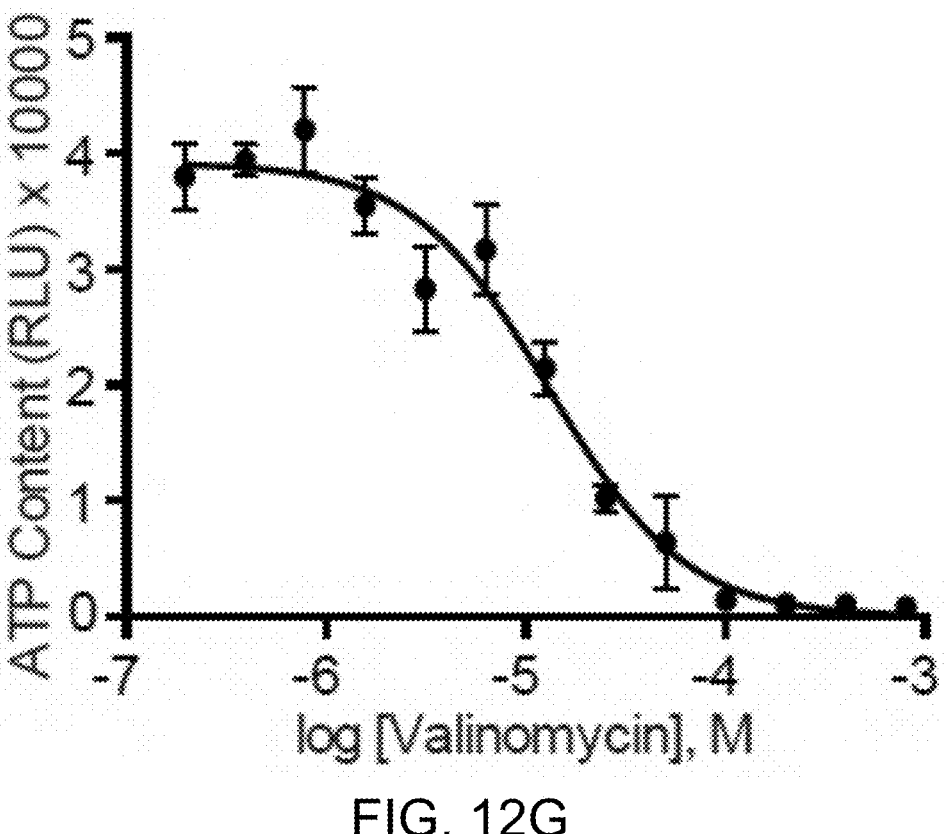

FIG. 12G is a graph showing ATP content (relative light units×1000) versus log concentration of valinomycin. The y-axis runs from 0 to 5 in increments of 1. The x-axis runs from −7 to −3 in increments of 1.

Figure 12H:
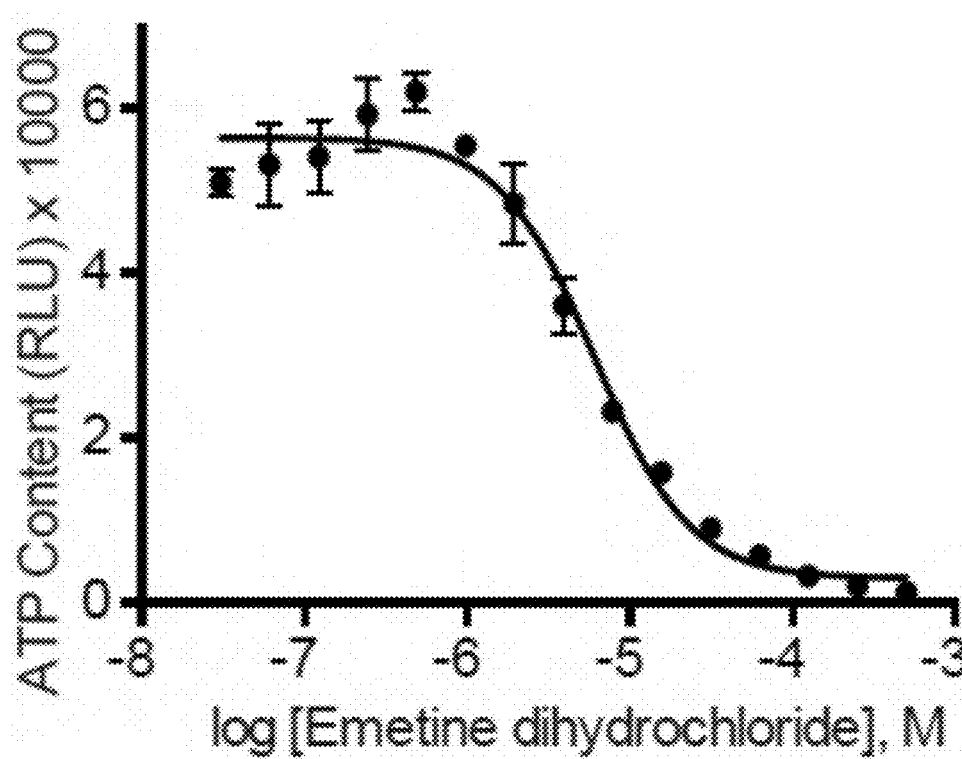

FIG. 12H is a graph showing ATP content (relative light units×1000) versus log concentration of emetine dihydrochloride. The y-axis runs from 0 to 6 in increments of 2. The x-axis runs from −8 to −3 in increments of 1.

FIG. 13A is a picture of two ischemic perfused injured hearts, one which had been injected with day 5 CM progenitor cells (labeled D5 progenitors) and a control mouse injected only with medium (labeled Medium). The picture shows a reduced infarct area in the D5 progenitors heart compared to a heart injected with Medium only.

FIG. 13B is a graph comparing the ejection fraction of the CM progenitor-treated mice (Cells) to the control (Medium) at week 4. The y-axis is ejection fraction and runs from 0% to 50% in increments of 10%.

Figure 13C:
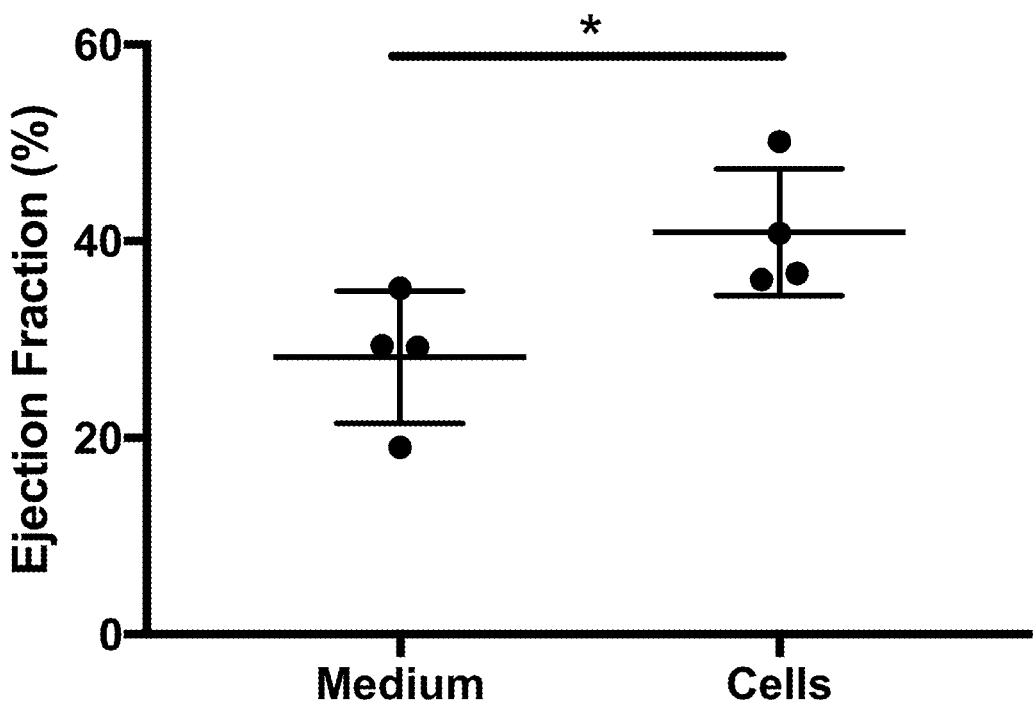

FIG. 13C is a graph comparing the ejection fraction of the CM progenitor-treated mice (Cells) to the control (Medium) at week 8. The y-axis is ejection fraction and runs from 0% to 60% in increments of 20%.

Figure 13D:
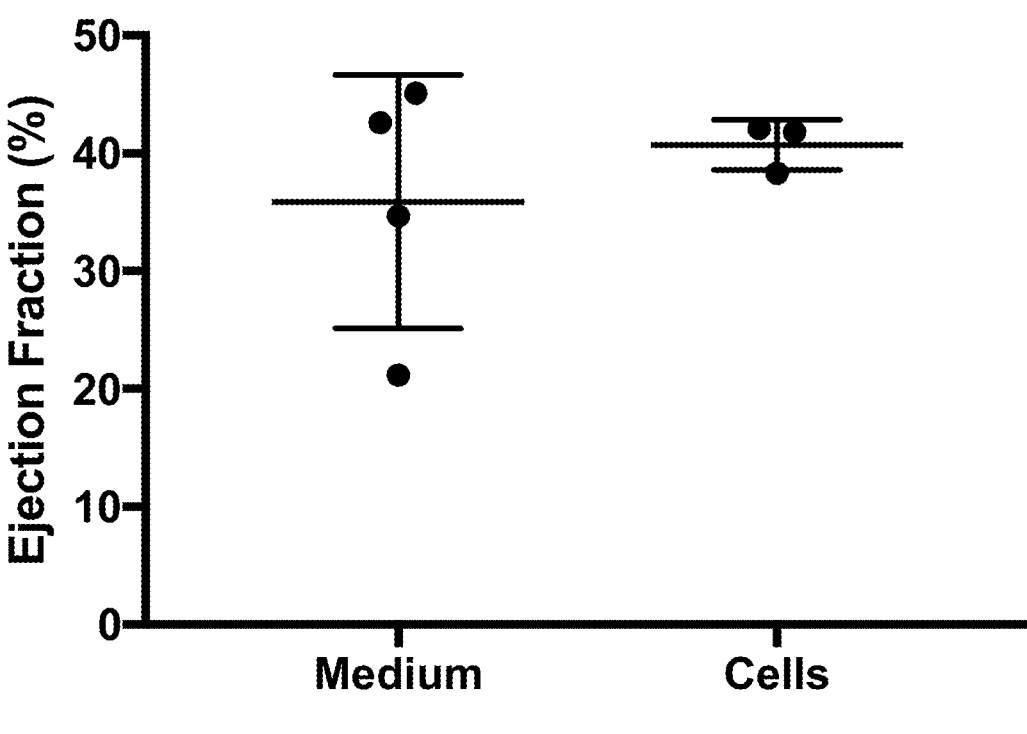

FIG. 13D is a graph comparing the ejection fraction of the CM progenitor-treated mice (Cells) to the control (Medium) at week 12. The y-axis is ejection fraction and runs from 0% to 50% in increments of 10%.

Figure 13E:
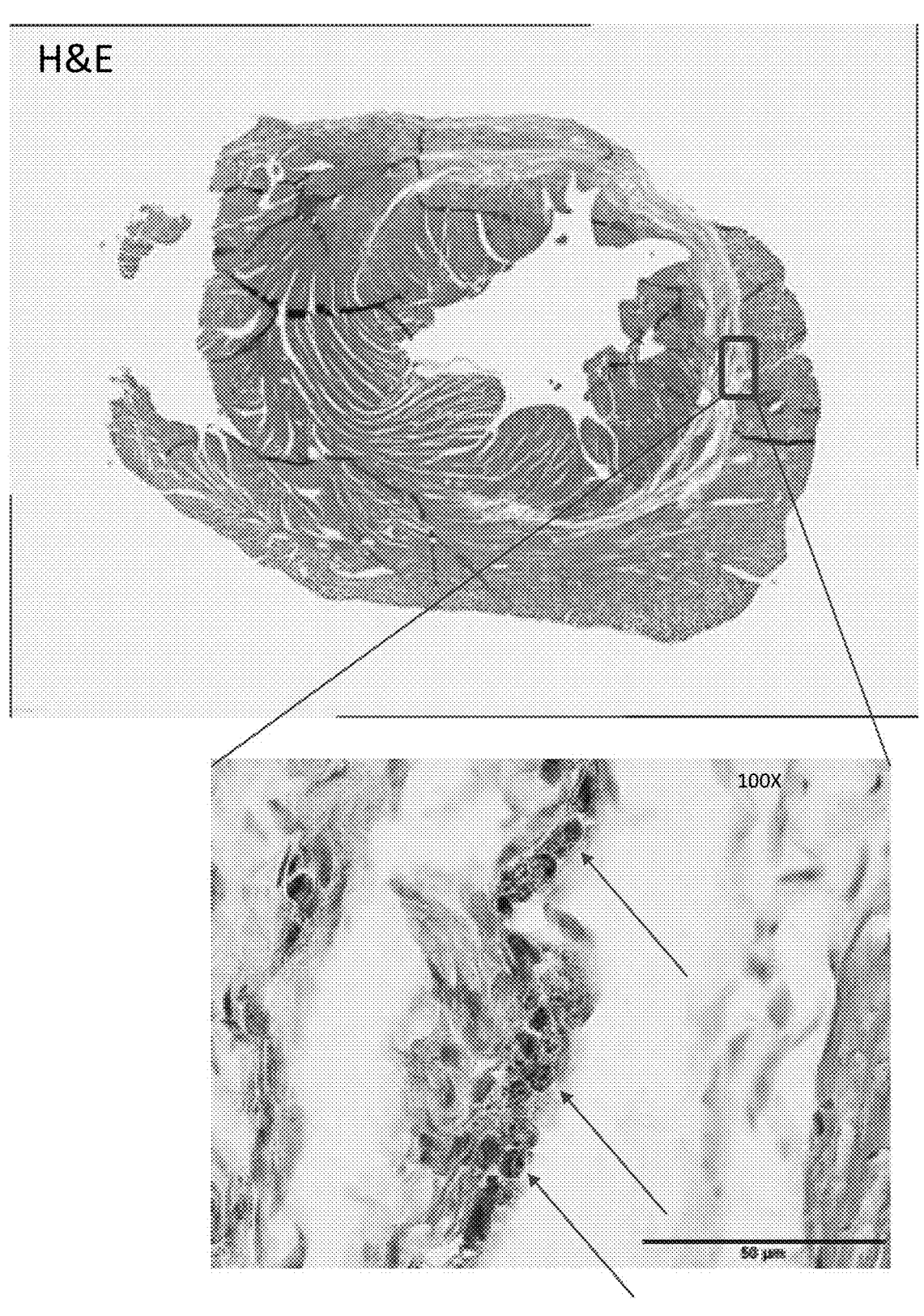

FIG. 13E is an H&E section on the infarcted heart of a progenitor-treated animal at week 12. The inset is 100× magnification, the scale bar is 50 μm.

Figure 13F:
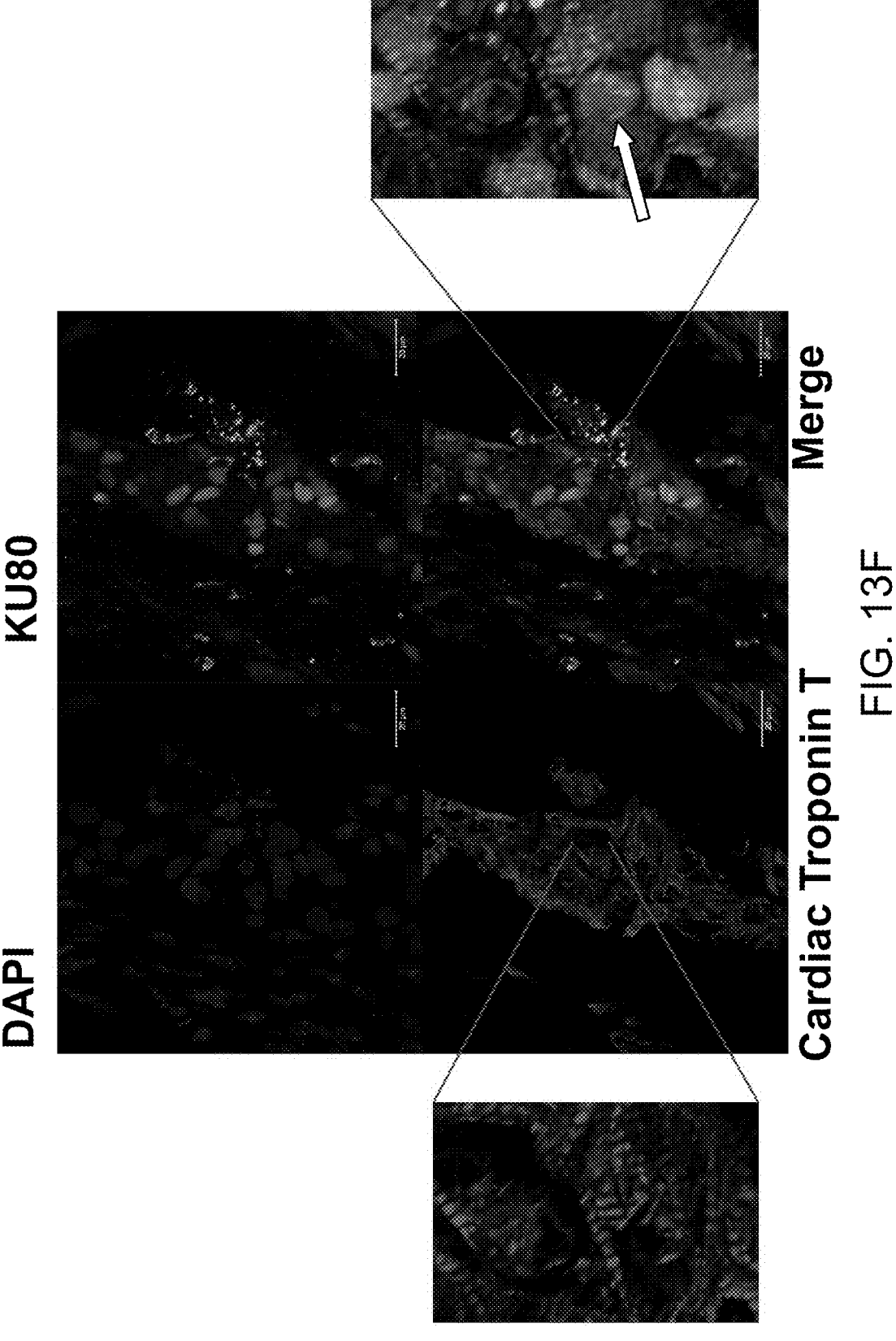

FIG. 13F is a set of four immunofluorescence stains of the heart sections with DAPI (blue), KU80 (green, specific for human nuclei), cardiac troponin T (red, for human and mouse troponin T) and a merge image showing the presence of human cardiomyocytes in the infarcted region.

Figure 14:
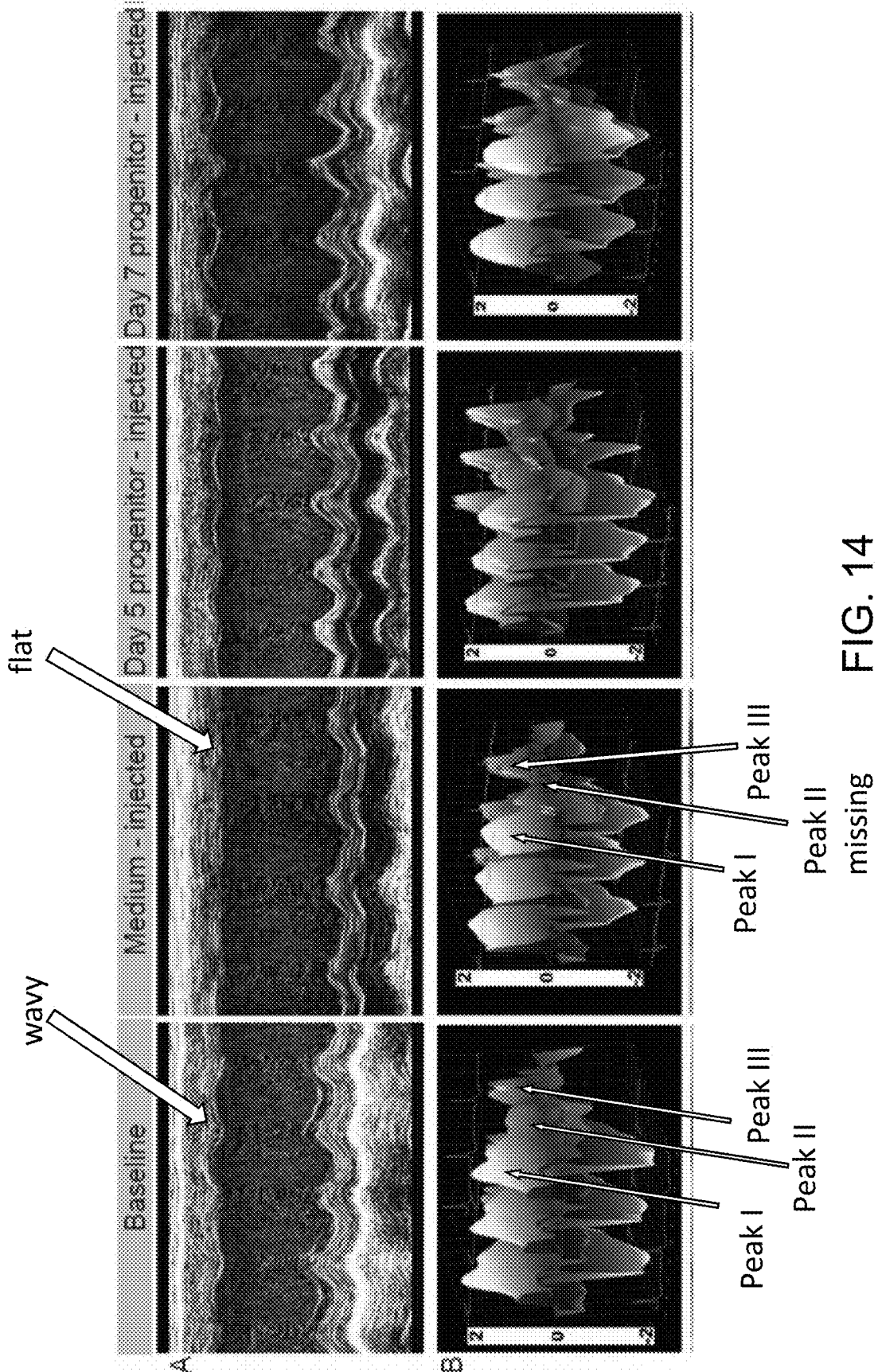

FIG. 14 is a set of 8 images, arranged in two rows and four columns. The leftmost column is baseline, the center left column is the Medium control (n=12), the center right column is Day 5 treatment (n=13), and the rightmost column is Day 7 treatment (n=8). Row A is a 2D echocardiogram (ECG) showing representative M-mode tracing at 8 weeks. Row B is a 3D regional wall velocity diagram of left ventricle endomyocardial strain over three consecutive cardiac cycles.

Figures 15A, 15B:
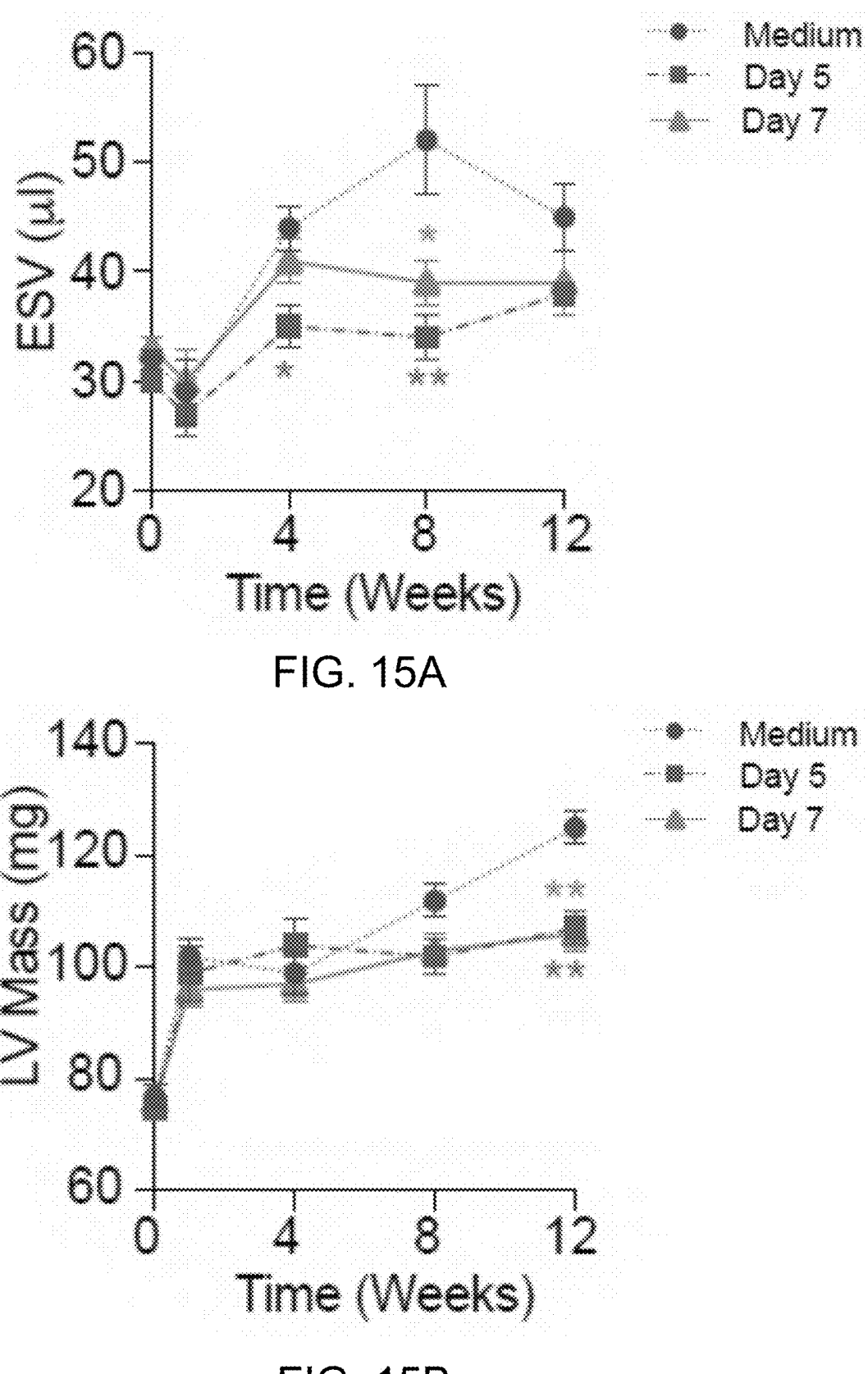
Figure 15C:
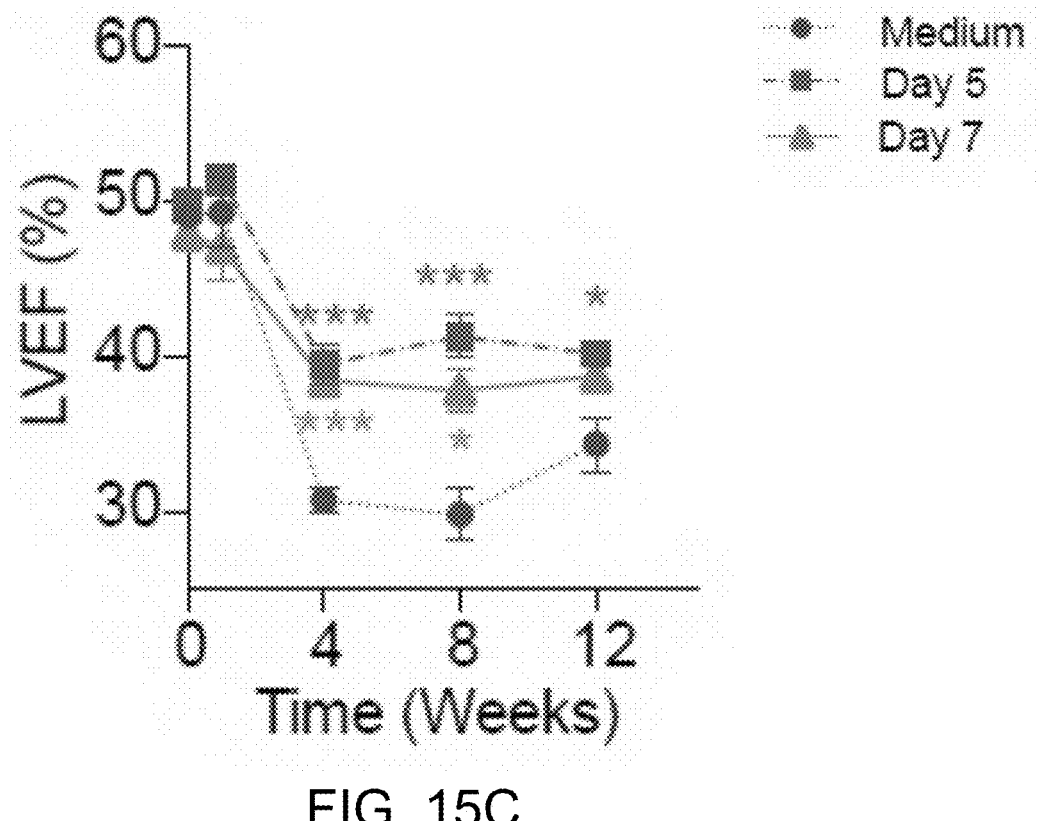

FIGS. 15A-15C are graphs comparing Medium treatment to Day 5 treatment and Day 7 treatment. Medium is circles on dotted line, Day 5 is squares on dot-dash line, and Day 7 is triangles on solid line.

FIG. 15A measures the End-Systolic Volume (ESV) in microliters (μL). The y-axis runs from 20 to 60 in increments of 10. The x-axis runs from 0 weeks to 12 weeks in increments of 4.

FIG. 15B measures the left ventricle mass (LV) in milligrams (mg). The y-axis runs from 60 to 140 in increments of 20. The x-axis runs from 0 weeks to 12 weeks in increments of 4.

FIG. 15C measures the left ventricle ejection fraction (LVEF) in %. The y-axis runs from 30 to 60 in increments of 10. The x-axis runs from 0 weeks to 12 weeks in increments of 4.

Figure 16A:
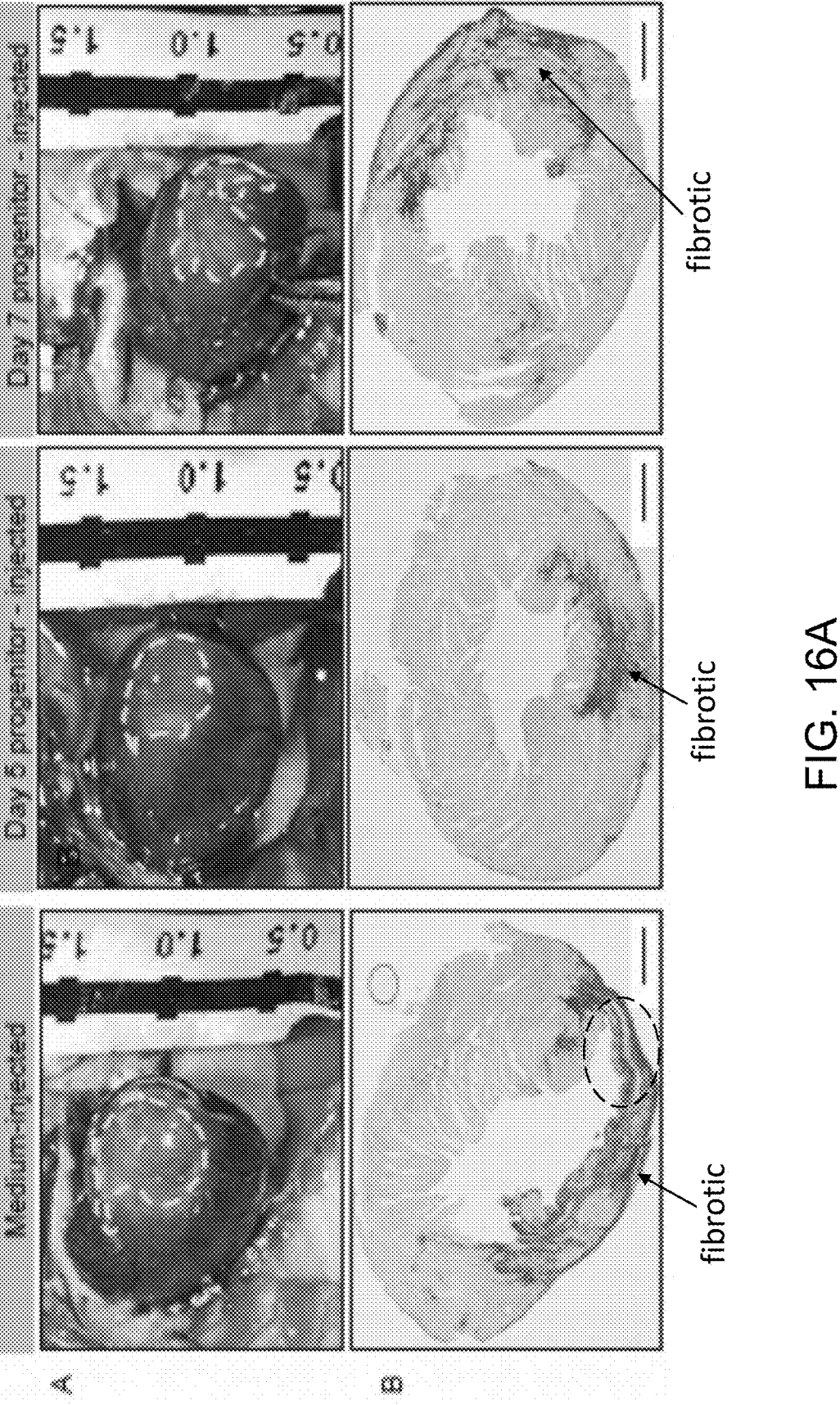
Figure 16B:
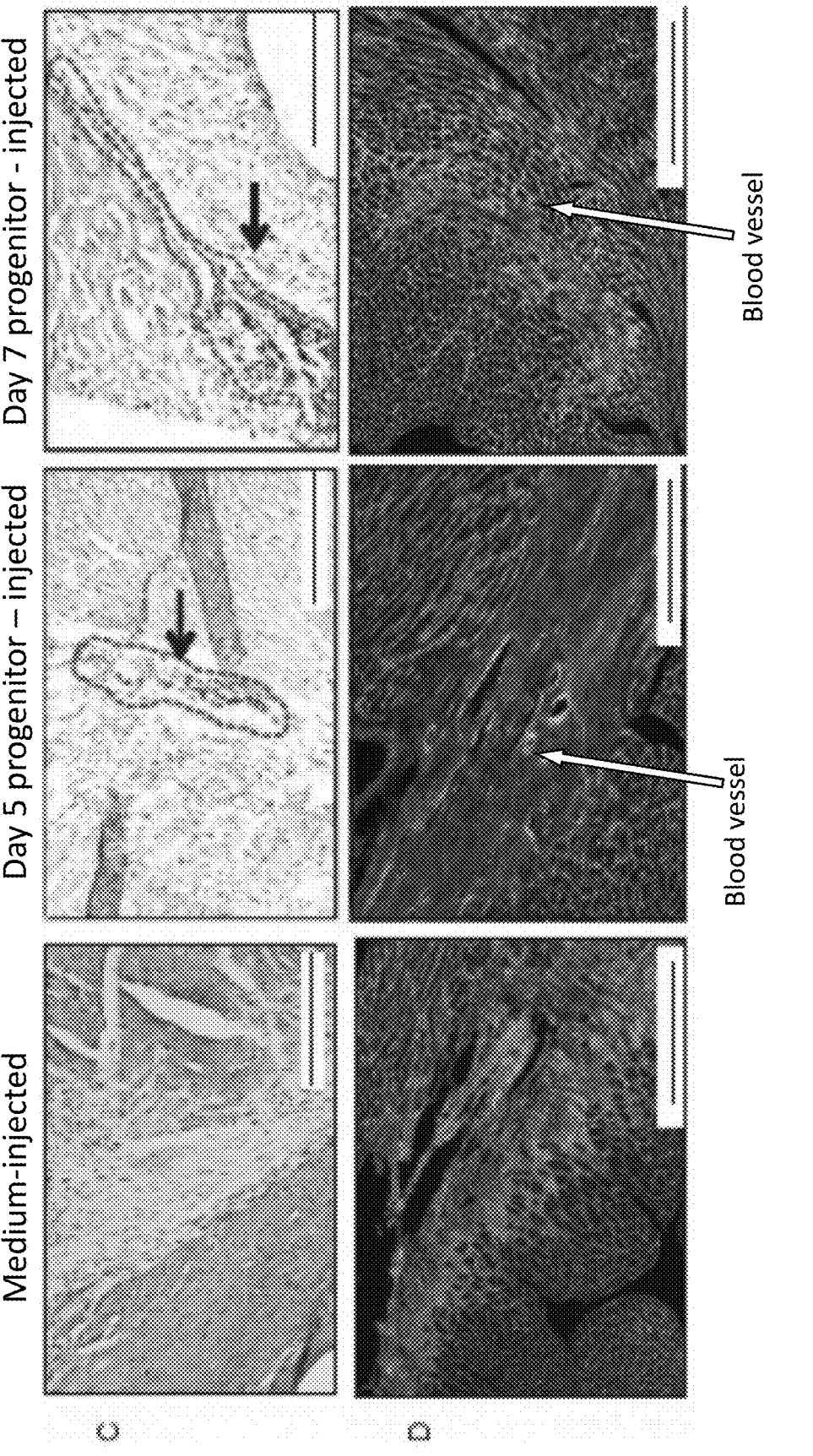

FIG. 16A and FIG. 16B is a set of 12 representative images, each figure being arranged in two rows and three columns, showing human muscle fiber observed in the infarcted area 12 weeks after treatment. The left column is from the Medium control, the center column is from the treatment with Day 5 CM progenitors, and the right column is from the treatment with Day 7 CM progenitors. Row A shows photomicrographs of the infarcted heart at the time of sacrifice. Row B shows Picrosirius Red staining. The scale bar is 1 millimeter (mm). Row C shows DAB staining. The scale bar is 200 micrometer (μm). Row D shows angiogenesis using isolectin 4 (red) and Wheat Germ Agglutination (WGA) antibody (red). The scale bar is 200 μm.

Figure 17:
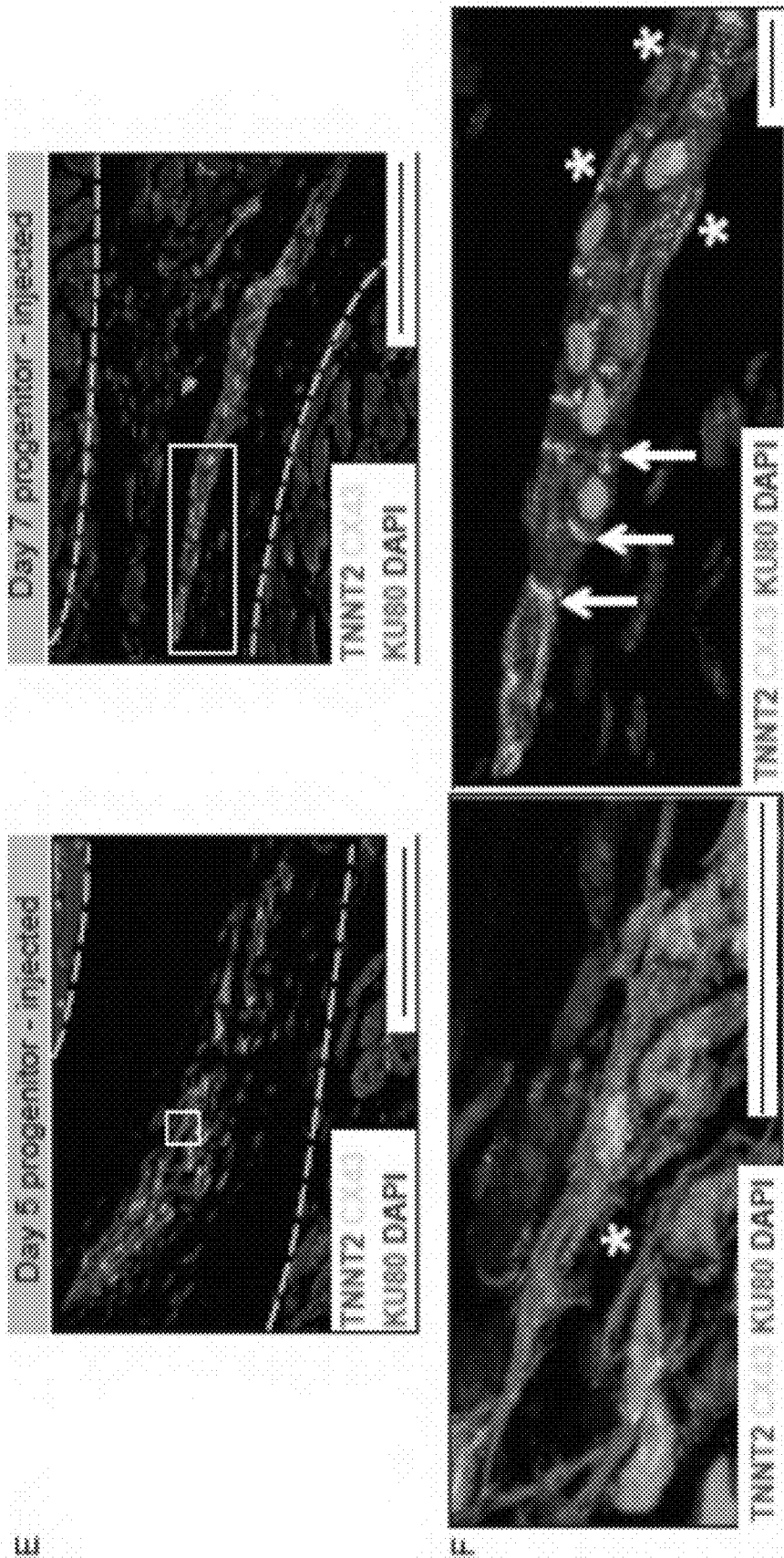

FIG. 17 is a set of four representative images, arranged in two rows and two columns, showing human muscle fiber observed in the infarcted area 12 weeks after treatment. The left column is from the Day 5 progenitors treatment, and the right column is from the Day 7 progenitors treatment. The yellow dotted lines demarcated the region of infarction. Row E shows confocal images of human muscle fiber stained with TNNT2 (red), KU80 (green), DAPI (blue), and connexin 43 (CX43, yellow) at 40× magnification. The scale bar is 25 μm. Row F shows the area inside the boxes in Row E, at 100× magnification. White arrows indicate aligned connexin 43. White asterisks indicate unaligned connexin 43.

Figure 18:
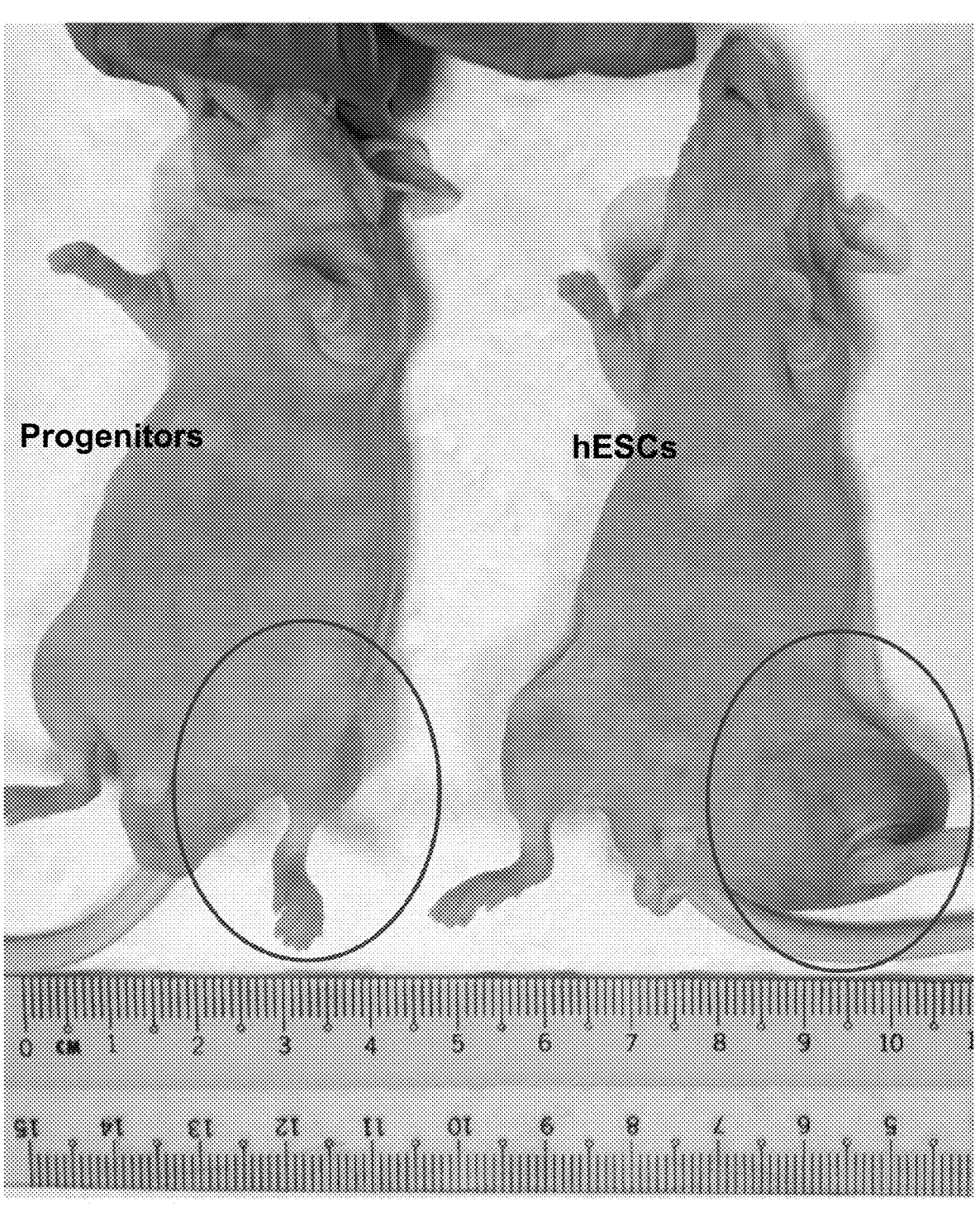

FIG. 18 is a picture of mice 8 weeks after injection of cardiomyocyte progenitors (left) or H1 pluripotent stem cells (right) into the hindlimb muscle.

Figure 19:
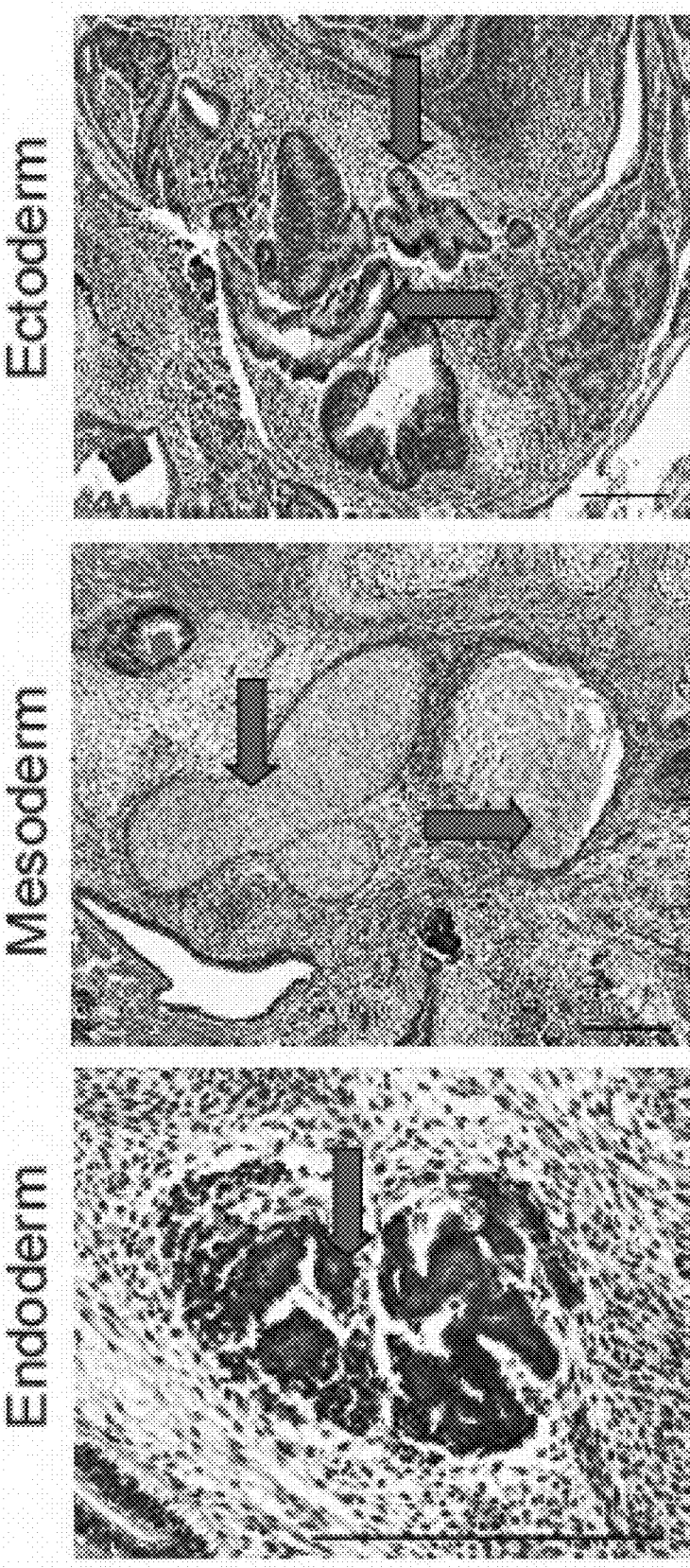

FIG. 19 is a set of three micrographs showing hematoxylin and eosin staining of a teratoma isolated from the mouse that was administered H1 pluripotent stem cells. The three micrographs show the ectoderm (neural rosette), mesoderm (bone and cartilage), and endoderm (pancreas) germ layers. The scale bar is 200 mm.

Figure 20:
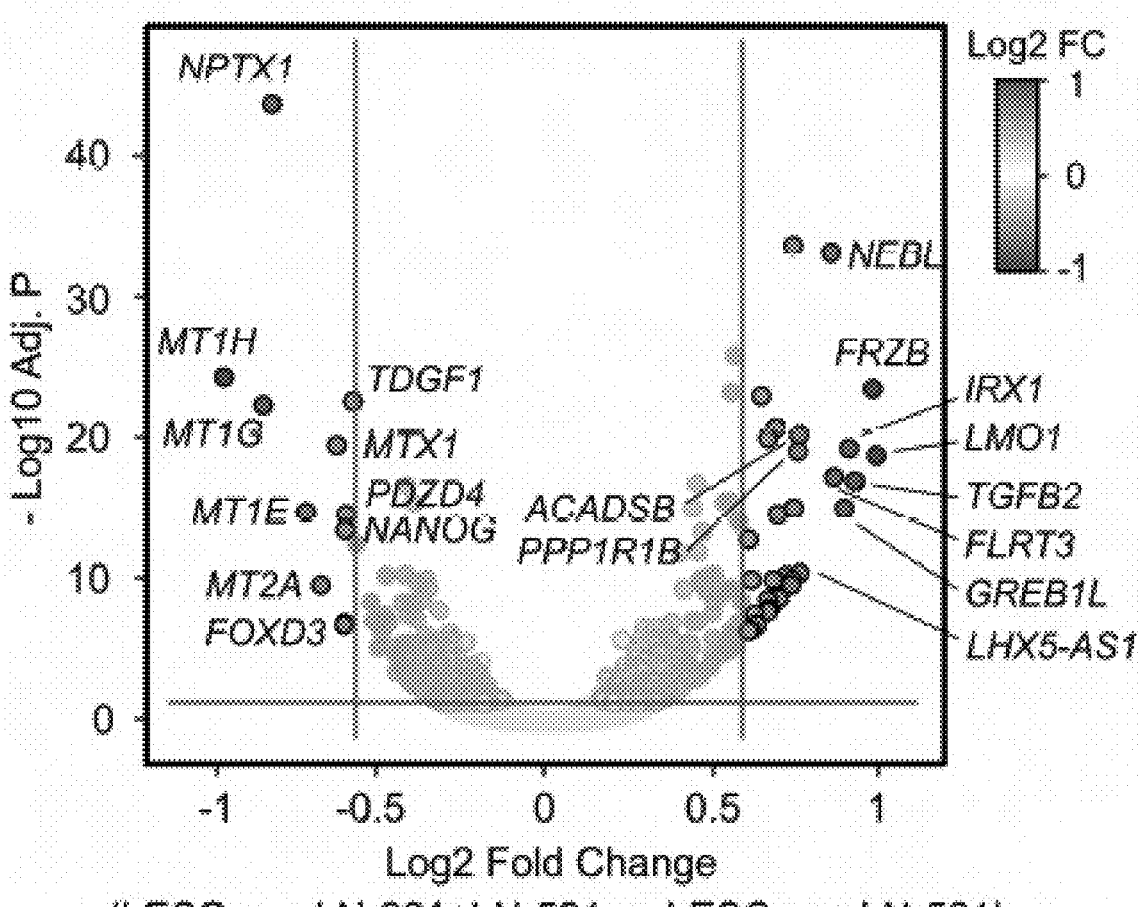

FIG. 20 is a volcano plot showing differential analysis of genes expressed by cells grown with or without LN-221 exposure. The y-axis is the Benjamini-Hochberg adjusted p-value ($-$Log10 Adj. P), and runs from 0 to 40 in increments of 10. The x-axis is the Log2 fold change of the gene, and runs from $-1$ to 1 in increments of 0.5.

Figure 21:
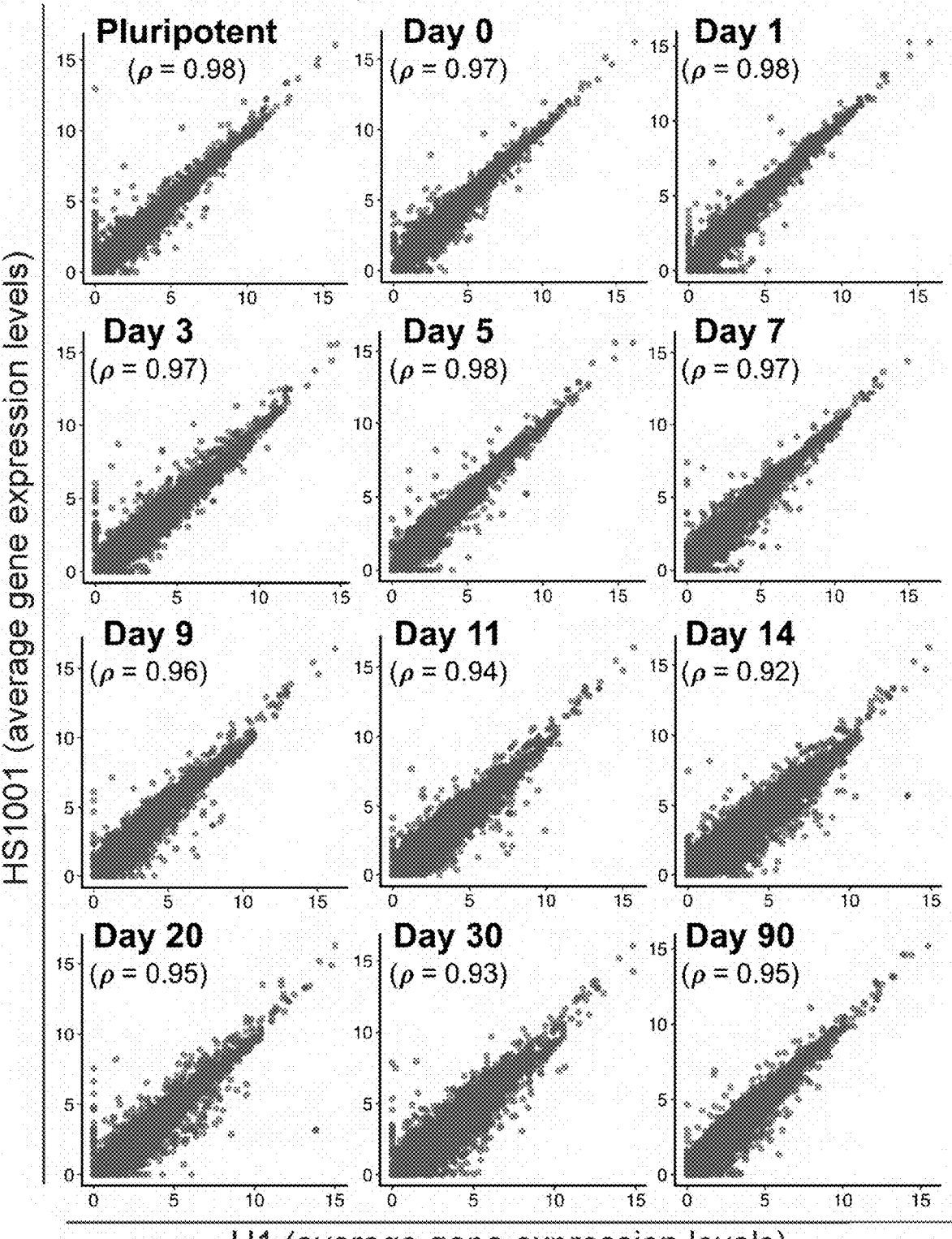

FIG. 21 is a set of 12 graphs showing transcriptome comparison between H1 and HS1001 cell lines on 12 different days over a 90-day differentiation period (Pluripotent stage, days 0, 1, 3, 5, 7, 9, 11, 14, 20, 30, and 90). For all graphs, the y-axis is the average gene expression level in HS1001 cells and runs from 0 to 15 in increments of 5; and the x-axis is the average gene expression level in HS1001 cells and runs from 0 to 15 in increments of 5. $\rho$ is Spearman's rank correlation coefficient (rho). $\rho$ ranges from 0.92 to 0.98 over the 12 graphs.

DETAILED DESCRIPTION

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

The methods of the present disclosure are related to maintaining the phenotype of differentiated cells. The term "phenotype" here refers to the cell's observable characteristics and properties. These include such things as the cell's morphology, biochemical or physiological properties, etc. It is desirable to maintain the cell's phenotype, particularly when the cells are going to be used for cell therapy or pharmacological or toxicology testing.

Due to their unique properties to renew indefinitely and their capacity to form all somatic derivatives of the human body, human pluripotent stem cells (hPSC) have a huge potential to be used in regenerative medicine. HiPS cells may also find applications in cell therapy, but also as model systems for studying aspects of human genetic diseases if the iPS cells are generated from individuals with a genetic disease. Another interesting perspective of hPSCs is their use in drug discovery in vitro where they generate wide interest for pharmaceutical research, spanning from early target studies to drug metabolism and pharmacokinetics studies or safety assessment. Cell-based in vitro assays with high human relevance are urgently needed for pre-clinical activities.

Currently used human cell systems are hampered by the fact that primary cells or available cell lines either rapidly lose specific functions, or they already lack these properties. Furthermore, many human primary cell types, like cardiomyocytes, are practically inaccessible for cell therapy of tissue damage like cardiac infarction, type I diabetes and Parkinson's disease, or drug and toxicity testing. hPSCs differentiated into functional progenitor of fully differentiated cells can provide a virtually unlimited supply of homogeneous human cell material needed in pharmaceutical research and development, which greatly facilitates broader screening activities like comparative studies or high-throughput compound testing. Moreover, genetic diversity and human variability can be easily addressed since specialized cells can be derived from multiple hESC-lines.

Full exploitation of the potential of hPSCs in these areas has long been limited by several major technical hurdles: (1) Culturing of hPSC without loss of pluripotency has been problematic; (2) Culturing of hPSCs was until recently impossible without the support of feeder cells or various animal supplements; (3) Genetic stability without the introduction of chromosomal changes has so far required "manual passaging" of hPSC colonies, severely limiting the scalability of culture; (4) Derivation of specific differentiated cell lineages relevant for therapeutic treatments, disease modeling or pharmaceutical research has been extremely inefficient, and; (5) cells differentiated from hPSC-derivatives are most often immature and do not adequately correspond to the differentiated cells in the recipient tissue or organ after transplantation. These technical hurdles may be addressed by using particular biologically relevant laminin substrates and/or other taking other steps during the generation of differentiated cells.

Differentiated cells require two things to survive and reproduce: (1) a substrate or coating that provides a structural support and correct outside-in signals to the cell; and (2) a cell culture medium to provide nutrition, growth factors and hormones to the cell. The substrate or coating (1) is generally placed on, for example, the surface of a petri dish, microtiter plate or some other container. It is particularly contemplated that the cell culture substrate on which the differentiated cell is plated comprises a laminin.

Laminins are a large family of heterotrimeric glycoproteins that reside primarily in the basal lamina immediately adjacent to the cell membrane. They function via binding interactions with neighboring cell receptors at one end of the laminin molecule, and by binding to other laminin molecules or other matrix proteins such as other laminins, collagens, nidogens or proteoglycans at the other end of the laminin molecule. The laminin molecules have several subdomains in different regions of the molecule which bind cell receptors and other molecules in the extracellular matrix. The laminin molecules are important signaling molecules that can strongly influence cellular behavior and function via binding to signaling receptors. Laminins are important in both maintaining cell/tissue phenotype, as well as in promoting cell growth, differentiation, adhesion and migration in tissue repair and development.

Laminins are large, multi-domain proteins, with a common structural organization. The laminin molecule integrates various matrix and cell interactive functions into one molecule.

Figure 1:
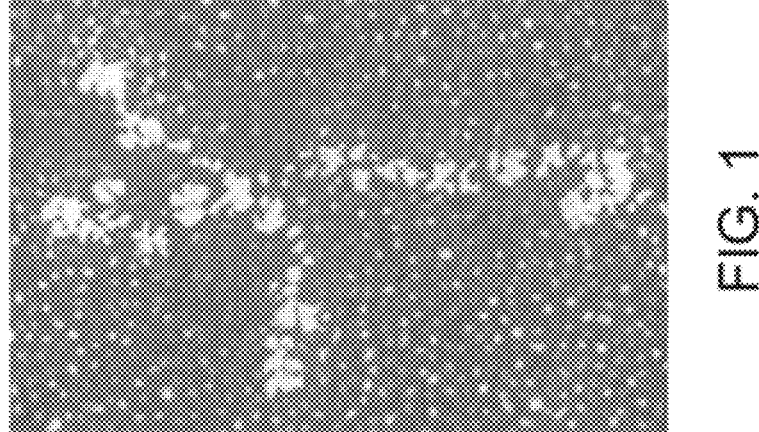
FIG. 1 is a rotary shadowing electron microscopy picture of a single recombinant laminin molecule containing α, β and γ chains. It reveals three short arms with small globular domains and one long arm with a large globular domain at the terminal end.

A laminin protein molecule comprises one α-chain subunit, one β-chain subunit, and one γ-chain subunit, all joined together in a trimer through a coiled-coil domain(1). FIG. 1 depicts the resulting structure of the laminin molecule. The twelve known laminin subunit chains can form at least 16 trimeric laminin isotypes in native tissues. Within the trimeric laminin structures are identifiable domains that possess binding activity towards other laminin and basal lamina molecules, as well as membrane-bound receptors.

Figure 2A:
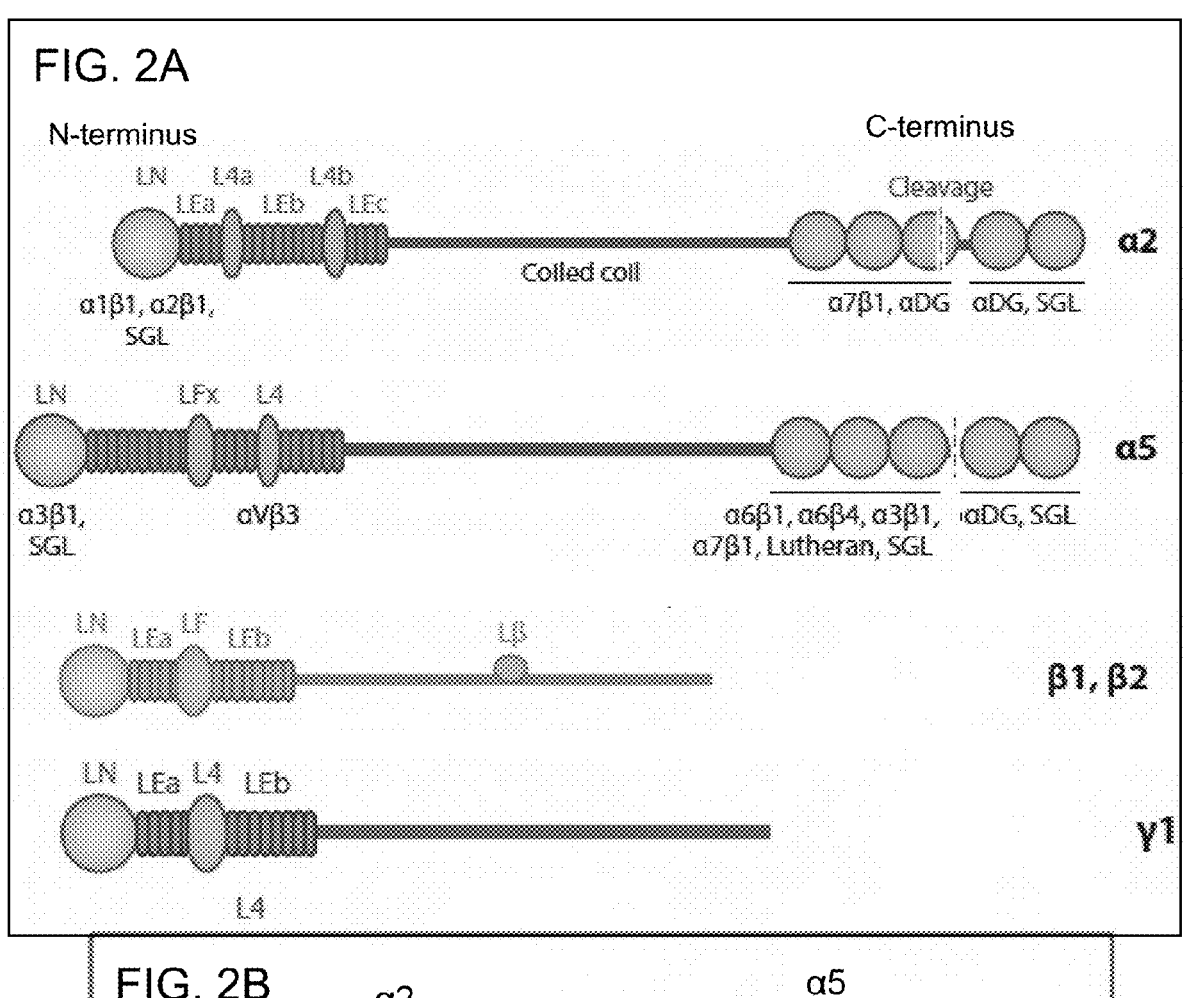
FIG. 2A is a drawing of the structural motifs of laminin α2, α5, β1, β2 and γ1 chains. Each laminin chain contains tandem arrays of globular and rod-like domains.

FIG. 2A shows the three laminin chain subunits (alpha-5 chain, alpha-2 chain, beta-1 chain, beta-2 chain and gamma-1) separately. Each laminin chain contains tandem arrays of globular and rod-like domains. The α chains have five large globular subdomains or motifs (LG 1-5) at the C-terminus. In α2 and α5, LG 4-5 are believed to be normally cleaved off extracellularly, while all LG motifs are probably intact in functional α1 and α2 chains. The LG domain is the main cell receptor binding region, but other domains may also interact with cellular receptors. The LG 1-3 domains bind to integrins, while LG 4 and LG 5 contain binding sites for dystroglycan (DG) and sulfated glycolipids (SGL). A small globular motif (Lβ) in the coiled-coil domain of the β chains binds to agrin. The N-terminal end of all the chains contains variable amount of EGF-like repeats in short rod-like domains (LEa-c), as well as 1-3 globular domains (L-N, L4, L4a, L4b, LFx).

There exist five different alpha chains, four beta chains and three gamma chains that in human tissues have been found in at least fifteen different combinations (1). These molecules (isoforms) were previously named as laminin-1, laminin-2, etc. according to their order of discovery, but currently they are named according to their chain composition, e.g. laminin-111 (laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including laminin-521, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

Generally, the cell culture substrate may contain any effective laminin, wherein the effectiveness is determined by whether differentiated cells can survive upon the substrate. It is specifically contemplated that the substrate contains either one or more particular laminins, though other ingredients may also be present in the substrate. In one embodiment, the laminin is laminin-521 (LN-521) or laminin-511 (LN-511). In other specific embodiments, the laminin is (i) LN-521 or LN-511 in combination with (ii) LN-221 or LN-211.

The term "laminin-521" refers to the protein formed by joining α5, β2 and γ1 chains together. The term "laminin-511" refers to the protein formed by joining α5, β1 and γ1 chains together. The term "laminin-221" refers to the protein formed by joining α2, β2 and γ1 chains together. The term "laminin-211" refers to the protein formed by joining α2, β1 and γ1 chains together. These terms should be construed as encompassing both the recombinant laminin and heterotrimeric laminin from naturally occurring sources. The term "recombinant" indicates that the protein is artificially produced using expression plasmids in cells that do not normally express such proteins.

The laminin can be an intact protein or a protein fragment. The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possess binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain. Further information of these domains is found in Domogatskaya, A., Rodin, S., and Tryggvason, K. 2012. Functional diversity of laminins. Annu Rev Cell Dev Biol 28:523-553, which is incorporated by reference.

The laminins can theoretically form over 50 different combinations, but at least 16 have been identified in mammals. The laminins are important for cell differentiation in the embryo; are major cell attachment molecules and are important for cell migration. They are herein used to generate a defined and xeno-free cell culture system that has been shown to provide a biologically relevant in vitro environment.

Figure 2B:
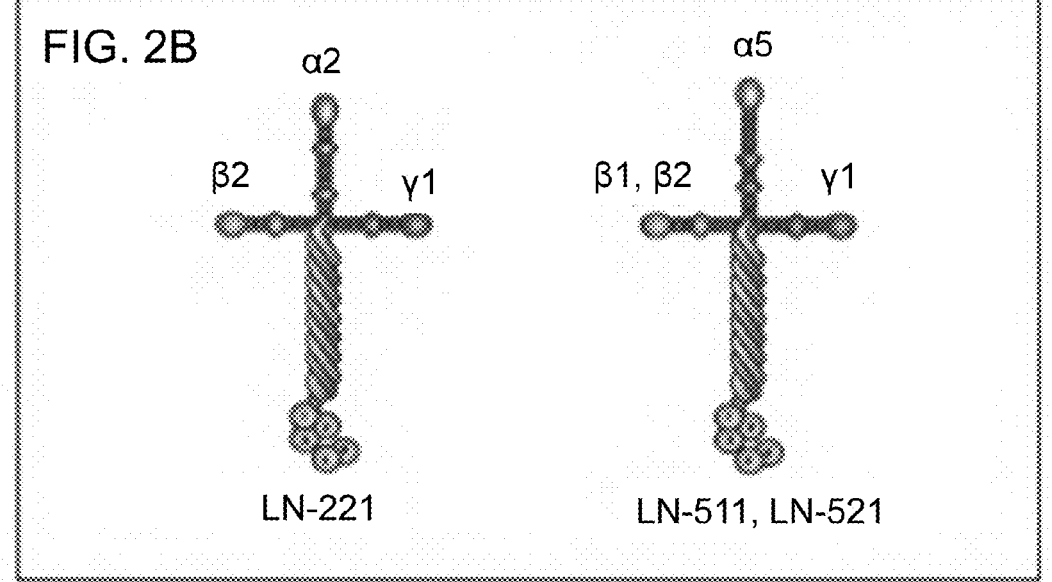
FIG. 2B is a drawing of laminin α, β and γ chains assembling to form a coiled-coil in at least 16 combinations. Here, the trimeric laminins LN-221 and LN-511 and LN-521 are illustrated.

With reference to FIG. 2B, the laminin α, β and γ chains assemble to form a coiled-coil in at least 16 combinations. Here, the trimeric laminins LN-221 and LN-511 and LN-521 are illustrated. Further information on LN-211, LN-511, and LN-521 is found in Aumailley, M., Bruckner-Tuderman, L., Carter, W. G., Deutzmann, R., Edgar, D., Ekblom, P., Engel, J., Engvall, E., Hohenester, E., Jones, J. C., et al. 2005. A simplified laminin nomenclature. Matrix Biol 24:326-332, which is incorporated by reference.

Different laminins are important for different cell types, both for their formation and phenotype maintenance. For example, LN-521 and LN-511 support efficient, long-term maintenance and propagation of hPSCs and hiPSCs without a risk of spontaneous differentiation or genetic changes. Further information on LN-521 and LN-511 is found in Rodin, S., Domogatskaya, A., Strom, S., Hansson, E. M., Chien, K. R., lnzunza, J., Hovatta, O., and Tryggvason, K. 2010. Long-term self-renewal of human pluripotent stem cells on human recombinant laminin-511. Nat Biotechnol 28:611-615, and Rodin, S. et al in Nat Commun, Jan. 27, 2014, which are incorporated herein by reference. LN-521 together with E-cadherin as a matrix facilitate clonal derivation of hES cells from an in vitro fertilized embryo without a need to destroy the embryo. See Rodin, S. et al. Nat Commun, Jan. 27, 2014.

LN-211 and LN-221 are highly specific for cardiac and skeletal muscle fibers (cells), and they also have important roles in the nervous system. However, LN-221 is the most abundant laminin isoform in human cardiac muscle, being about 3 times more abundant than LN-211 based on global transcriptome analysis from the heart ventricle. The other most common laminins present in heart muscle are LN-511 and LN-521.

Heart muscle cell (cardiomyocyte) progenitors and mature cardiomyocytes, are of critical importance for the development of cell therapy of heart muscle injury. Although pluripotent stem cells can be differentiated towards cardiomyocytes by culturing them on extracellular matrix substrata such as murine Matrigel™, or on feeder cells such as human or mouse fibroblasts, or by 3-dimensional embryoid body (EB) differentiation, or by inductive co-culture with END2 cells in the presence of differentiation conditions, these methods are not chemically defined and their results vary from one experiment to another (i.e. there is a lack of reproducibility). These methods either require the inclusion of serum; have heterogeneous EB sizes; and/or utilize a complex matrix (Matrigel™) that is a murine tumor extract containing several basement membrane proteins (e.g. type IV collagen, perlecan, laminin) as well as growth factors and intracellular proteins. Additionally, the laminin present in Matrigel™ is LN-111, which hardly exists in normal heart muscle. Matrigel™ is the most used cell culture coating for the maintenance of pluripotent stem cells and also a frequently used substrate for cell differentiation, where it is used for the re-plating of EB and monolayer differentiation. Unfortunately, however, Matrigel™ is isolated from a basement membrane-like matrix produced by whole mouse tumor (EHS sarcoma) tissue and, thus, is xenogenic, affected by lot-to-lot variations and contains an extensive amount of undefined components. Moreover, cells cultured on Matrigel™ also have the possibility to acquire non-human N-glycolylneuraminic acid (Neu5Gc) immunogen, which renders them unsuitable for clinical applications.

A study by Lian et al. demonstrated that pluripotent stem cells are able to differentiate using small molecules that modulate Wnt signaling pathway in a monolayer using Matrigel™ and a commercial plate called Synthemax using mTeSR1 media with rho-kinase (ROCK) inhibitor. The exact component of Synthemax is proprietary to Corning®. However, it is based on a study by Melkoumian et al. Further information on the Melkoumian study is found in Melkoumian, Z., Weber, J. L., Weber, D. M., Fadeev, A. G., Zhou, Y., Dolley-Sonneville, P., Yang, J., Qiu, L., Priest, C. A., Shogbon, C., et al. 2010. Synthetic peptide-acrylate surfaces for long-term self-renewal and cardiomyocyte differentiation of human embryonic stem cells. Nat Biotechnol 28:606-610, which is incorporated by reference. The authors reported that the synthetic RGD peptide sequence of vitronectin protein is sufficient to maintain pluripotent stem cells. However, this surface is not a biologically relevant substrate for any cells in the body. Moreover, the medium used (mTeSR1) contains bovine serum albumin (BSA) and high concentration of basic FGF growth factor (100 ng/ml). In addition, the authors seeded single cells that require additional ROCK inhibitor to diminish dissociated-induced apoptosis. The actual mechanism by which this inhibitor functions to promote single cell survival is still unknown. Therefore, the existence of differentiation protocols providing a completely chemically defined, controllable and xeno-free environment is desired.

The neonatal mammalian heart is capable of significant regeneration of the injured heart muscle for only about a week after birth. After that, cell cycle arrest occurs by unknown mechanisms and that hinders proliferation of cardiac cells and subsequent tissue repair. Recent progress in stem cell research and design of novel differentiation protocols has opened up possibilities for new cell therapy approaches to treatment of cardiac muscle injury. Several types of cells have been explored for cell therapy purposes, but currently the most attractive sources include (i) cardiomyocyte progenitors or cardiomyocyte-like cells derived from either hESCs or induced (reprogrammed) pluripotent stem cells (iPSC), (ii) cardiomyocytes reprogrammed directly from fibroblasts, or (iii) cardiomyocyte progenitors isolated and expanded from embryonic or adult heart muscle tissue. The reprogrammed cell lines derived from human fibroblasts have been generated by administration of vectors containing cDNAs for various transcription factors, which can pose a problem as they involve changes in the genome. One concern is that such cells can become tumorigenic and therefore they may not be suitable for cell therapy of human disease. Therefore, it would be desirable to be able to derive cardiac progenitors or mature cardiomyocytes from pluripotent embryonic or mesenchymal stem cells, or also from progenitor cells derived from adult cardiac muscle tissue.

In one embodiment, a method for differentiating a human cardiac progenitor cell or mature human cardiomocyte cell from pluripotent stem cells includes maintaining hESCs on embryonic laminins LN-521 or LN-511 in the presence of laminins present in the basement membrane surrounding the muscle fiber cells, LN-211 and LN-221. Suitable laminins include specific laminin isoforms, e.g. LN-511, LN-521, LN-211 and LN-221, provided by BioLamina, AB, in Sweden.

Figure 3A:
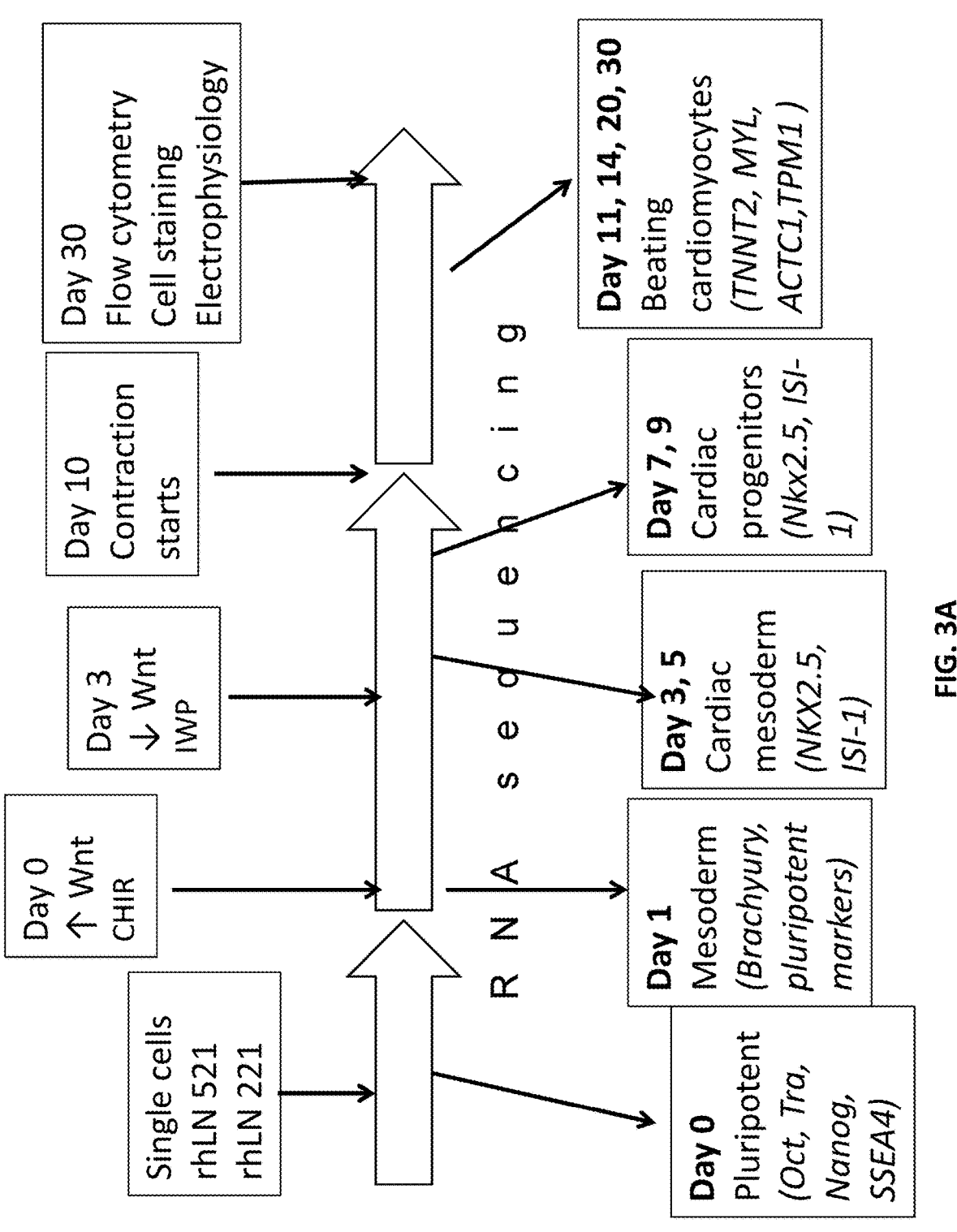

With reference to FIG. 3A, a high level summary of method steps according to one embodiment of differentiating hES cells to beating cardiomyocytes is described. The term "CHIR" refers to a glycogen synthase kinase 3 (GSK3) inhibitor which mimics Wnt signaling. The term "IWP" refers to a Wnt Inhibitor which serves as an antagonist of the Wnt/β-catenin pathway. The term "Wnt" represents Wnt proteins, which are highly conserved secreting molecules that regulate cell-to-cell interactions during embryogenesis. The acronym "rhLN" stands for recombinant human laminin.

With reference to FIG. 3B, a day-by-day illustration of steps corresponding to a method of differentiating pluripotent stem cells to beating cardiomyocytes is described.

Figure 3C:
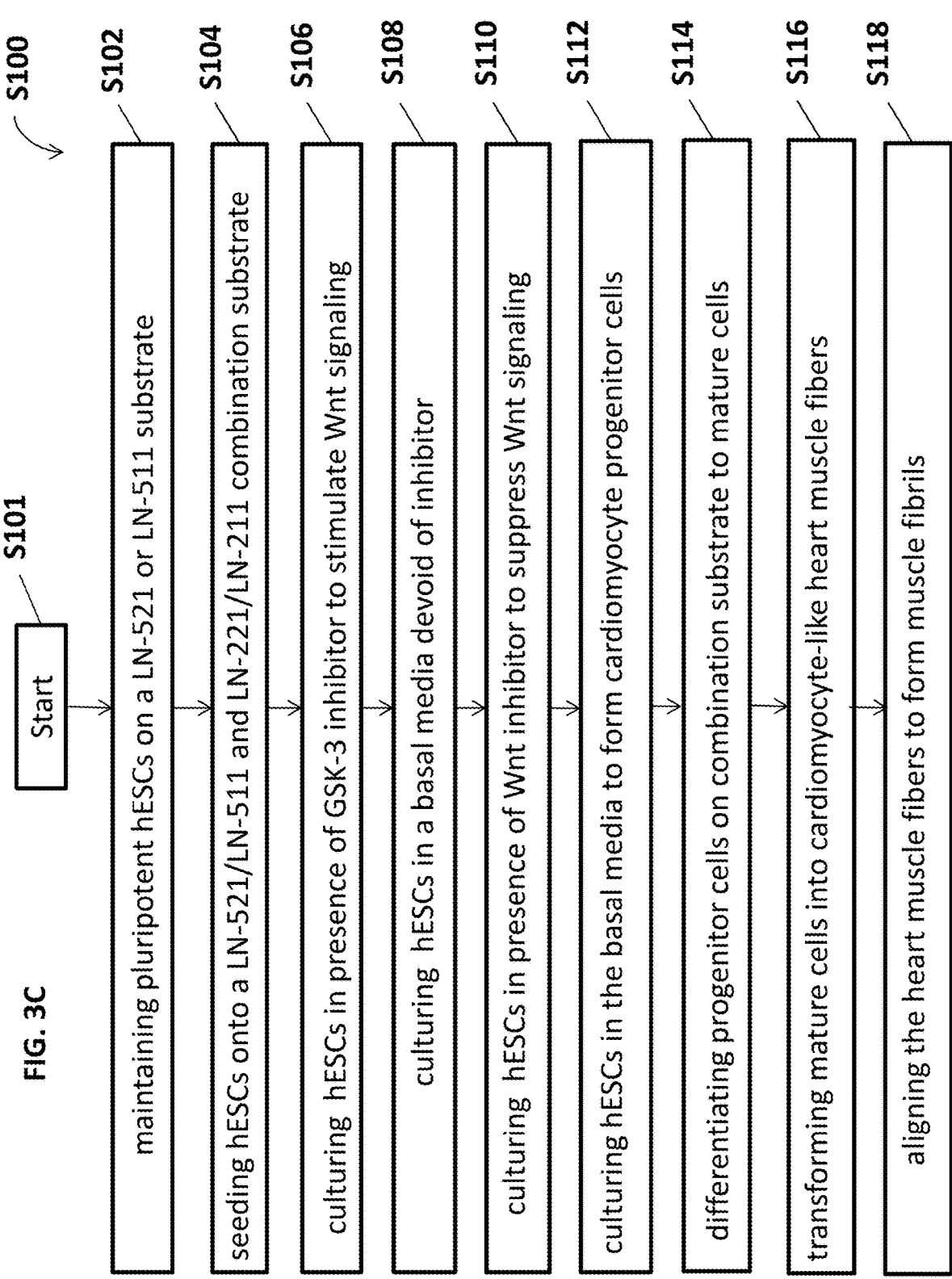

With reference to FIG. 3C, a method S100 for differentiating cardiomyocytes from pluripotent stem cells using laminin substrates according to another embodiment starts at S101.

At S102, pluripotent cells are maintained on a substrate made of (i) laminin-521 (LN-521) or laminin-511 (LN-511) combined with (ii) LN-221 or LN-211. In particular embodiments, it is contemplated that the weight ratio of the laminin-521/511 to the laminin-221/211 in the substrate is from about 1:6 to about 6:1, including from about 1:4 to about 4:1, including from about 1:2 to about 2:1. In some particular embodiments, the weight ratio of the laminin-521/511 to the laminin-221/211 in the substrate is from about 1:1 to about 1:4 (i.e. contains more laminin-221/211 than laminin-521/511), including about 1:3. The substrate has only two laminins, selected in the combinations described herein, although other ingredients can be present in the substrate as well. In particular, the substrate does not contain LN-111.

At S104, the pluripotent cells are seeded onto a combination substrate including (i) LN-521 or LN-511 and (ii) LN-221 or LN-211 and maintained for five days.

At S106, the pluripotent cells are cultured for one day in the presence of a GSK-3 inhibitor to inhibit β-catenin phosphorylation, which in turn stimulates canonical Wnt signaling. Suitable GSK-3 inhibitors include CHIR 99021 from Stemgent of Cambridge, Mass., and other similar inhibitors as known by one having ordinary skill in the art.

At S108, the pluripotent cells are cultured in a basal medium devoid of inhibitor for two days.

At S110, pluripotent cells are cultured for two days with a Wnt inhibitor to suppress Wnt signaling.

At S112, the cells are cultured for 2 days in the basal medium where they form cardiomyocyte progenitor cells. These hESCs may express Islet-1 and NXK2.5 transcription factors, which are biomarkers for cardiomyocyte progenitor cells. Expression of the Islet-1 transcription factor is illustrated in the photomicrograph of FIGS. 4A-4C. With reference to FIG. 4A, a photomicrograph of Islet-1 transcription factor expression shows cardiomyocyte progenitors derived from hESCs. Cells were immunostained in FIG. 4A with DAPI for nuclei, FIG. 4B and FIG. 4E for Islet-1, NKX2-5 and FIG. 4C, FIG. 4F showing the merged results. Results show that Islet-1 and NKX2-5 are located in the nucleus of the cells, which strongly demonstrates the presence of cardiac progenitor cells.

Figure 5A:
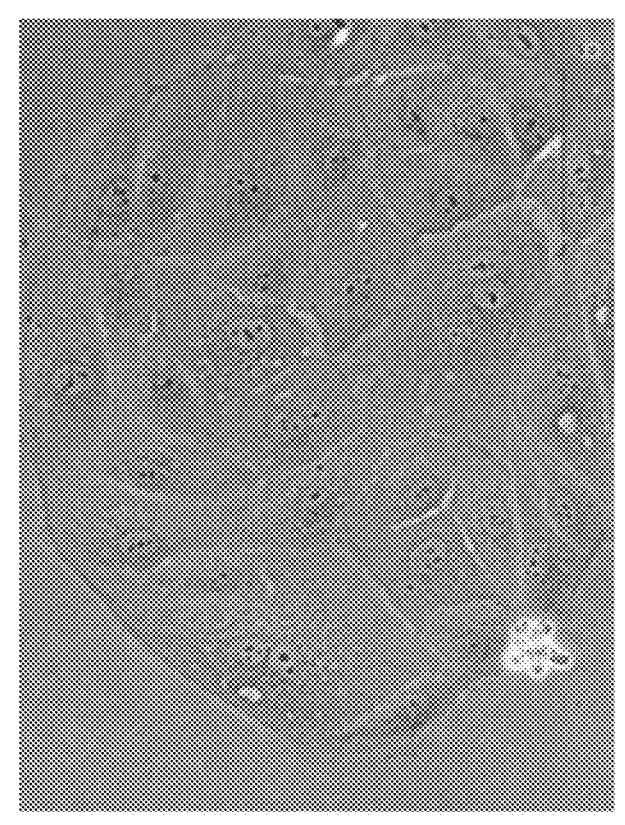
FIGS. 5A-5C include an analysis of cardiac progenitors. The cells were analyzed with Islet-1 and NKX2.5 antibodies.
Figures 5B, 5C:
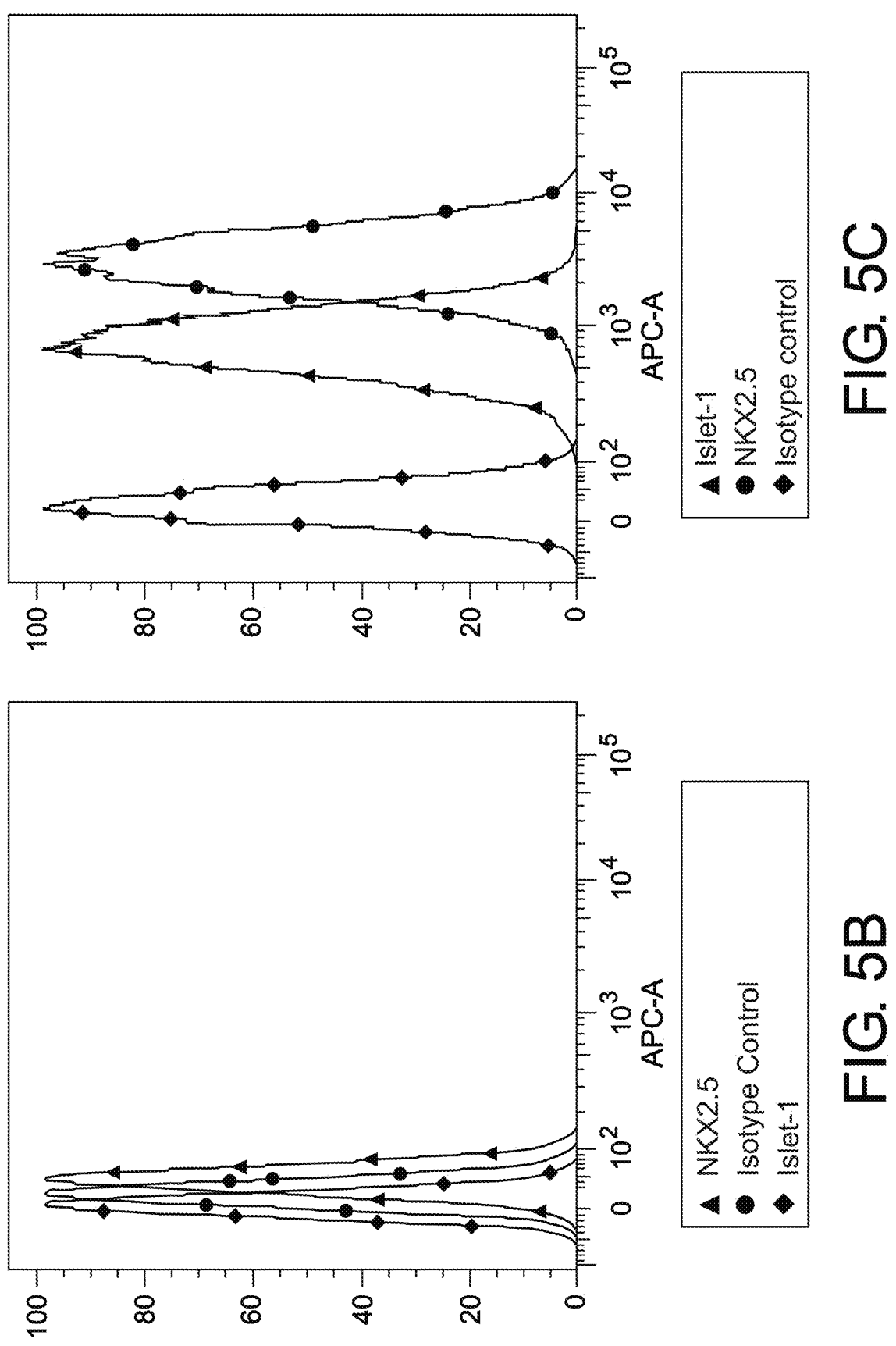

With reference to FIG. 5C, flow cytometry analysis show 99% cells are expressing Islet-1 and NKX2-5 cardiomyocytes biomarkers.

Referring back to FIG. 3C, at S114, the progenitor cells are further differentiated on the combination substrate to generate mature cardiomyocyte cells.

At S116, mature cardiomyocyte cells are transformed into cardiomyocyte like human heart muscle fibers which may be aligned pairwise into muscle fibrils, maintaining the beating, striated phenotype. The muscle fibrils are illustrated in FIG. 6A. With reference to FIG. 6C, single cardiomyocytes have a rectangular phenotype, which are the typical morphology for cardiomyocytes in the body.

With reference to FIG. 7, a photomicrograph shows the expression of FIG. 7A cardiac troponin T (cTNT), FIG. 7B cardiac troponin I (cTNI), FIG. 7C myosin light chain for ventricular cells (MLC2v) and FIG. 7D α-actinin biomarkers in the cardiomyocytes from the human heart muscle fibers of FIG. 5. Aligned Sarcomere organization was observed from the staining. Nuclei were stained with DAPI.

Figures 8A, 8B:
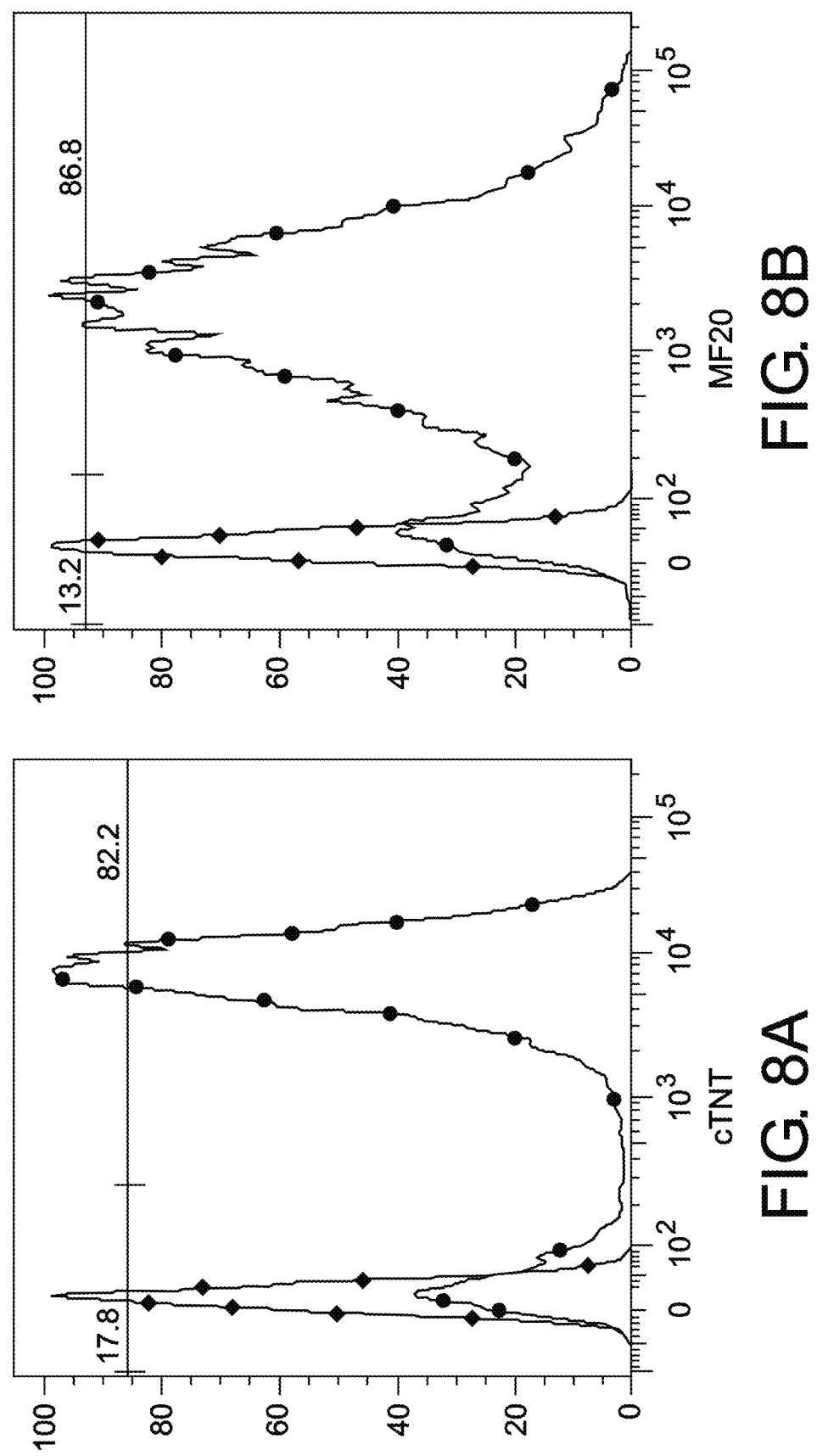
FIGS. 8A-8C show flow cytometry analysis of Day 30 cardiomyocytes.
Figure 8C:
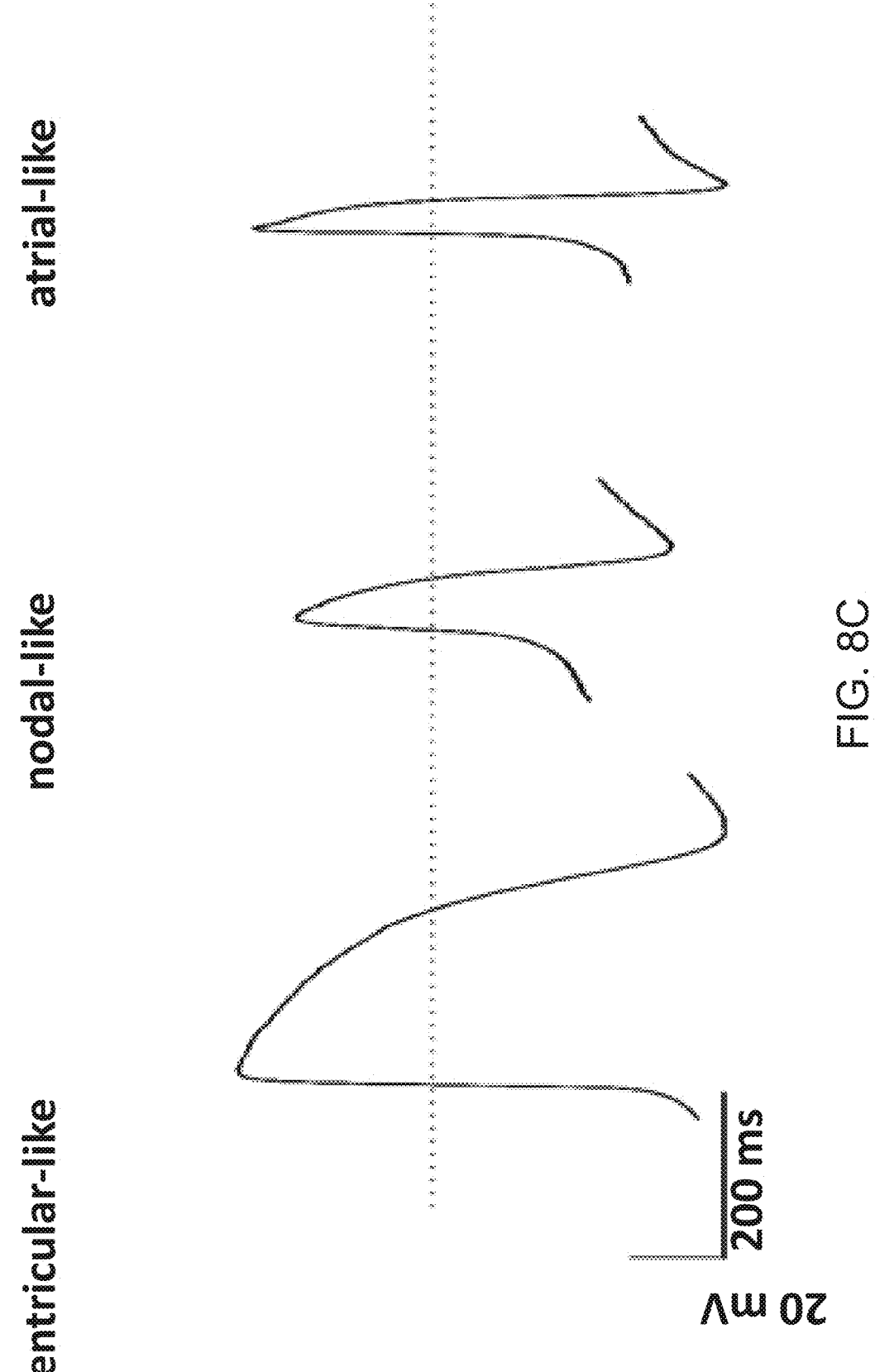

At S118, heart muscle fibers to form muscle fibrils are aligned with each other length-wise into muscle fibrils. The muscle fibrils and aligned muscle fibers are illustrated in the photomicrograph of FIG. 6. At day 20, the beating cardiomyocytes contain cells that mimic heart ventricle, atrium and nodal subtypes as determined by patch clamp analyses (FIG. 8C).

The methods set forth in FIG. 3C may be used to generate cardiomyocytes from hESCs during a period of 14 days under chemically defined, xeno-free conditions and without genetic manipulation. Method S100, particularly at S116, may also be used to develop human heart muscle cells for future regenerative cardiology. In one embodiment, the pluripotent stem cells in Method S100 are hESCs.

Figure 9A:
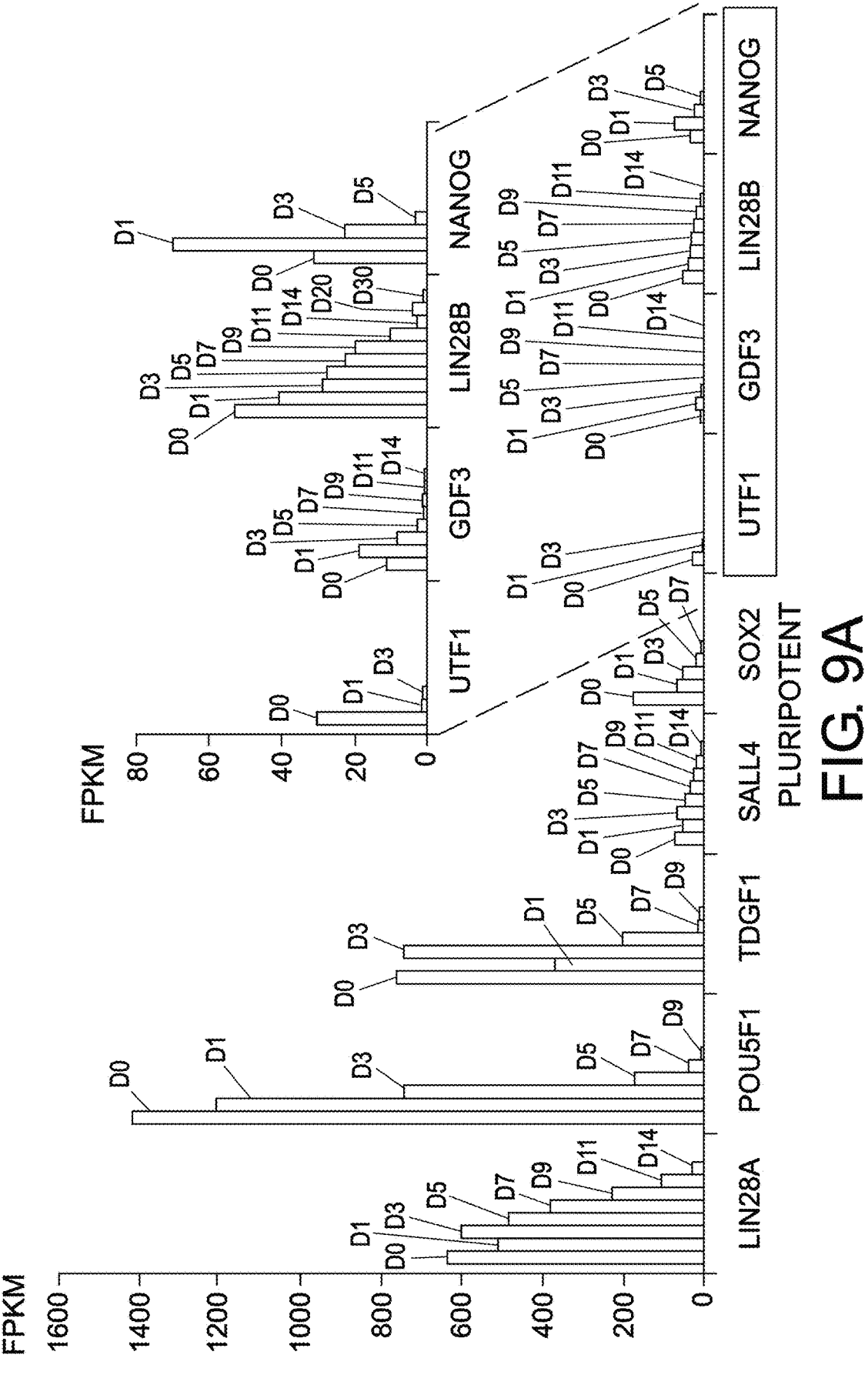
FIGS. 9A-9C include a detailed transcriptome analysis of differentiation days 0, 1, 3, 5, 7, 9, 11, 14, 20 and 30.
Figure 9B:
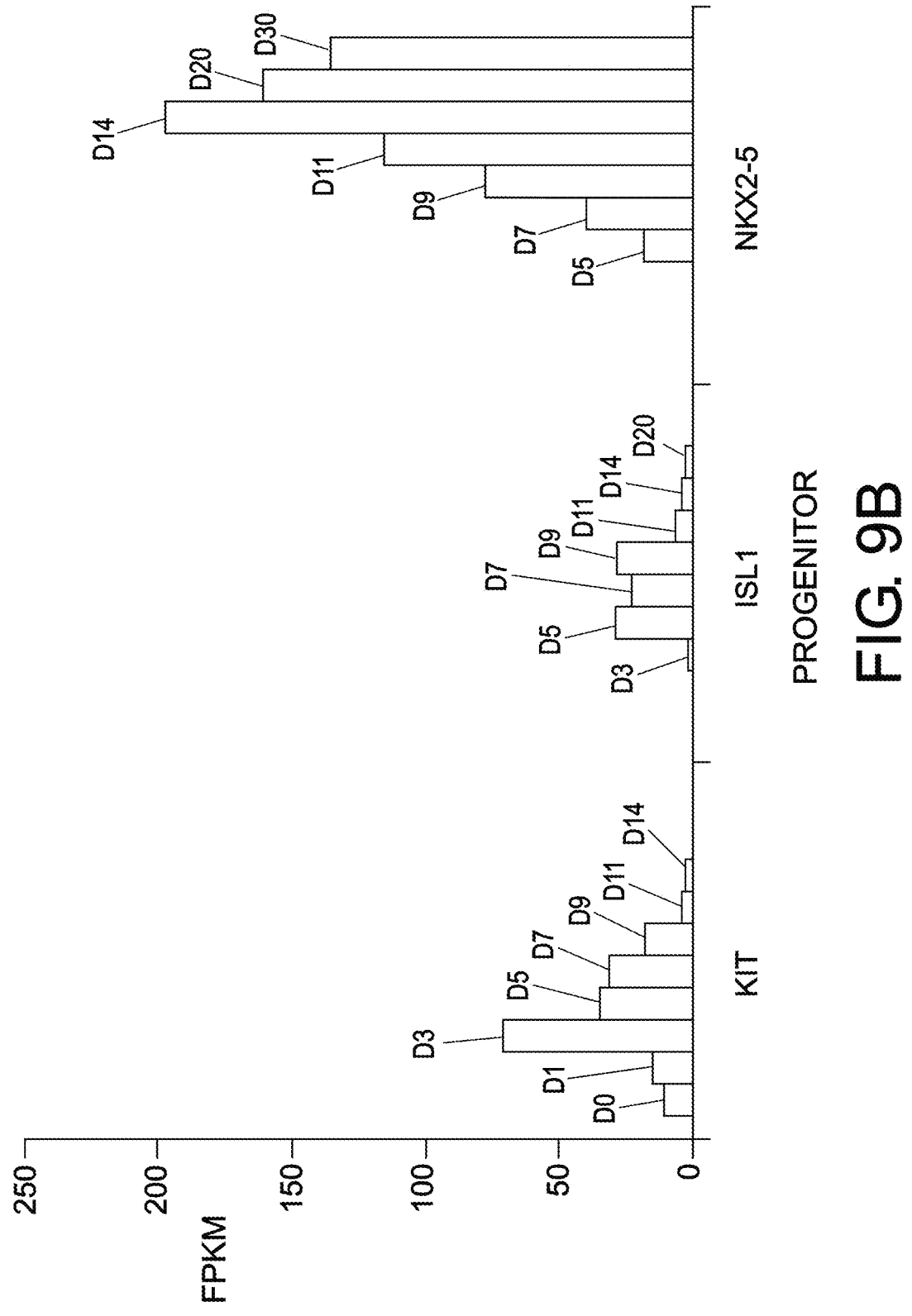
Figure 9C:
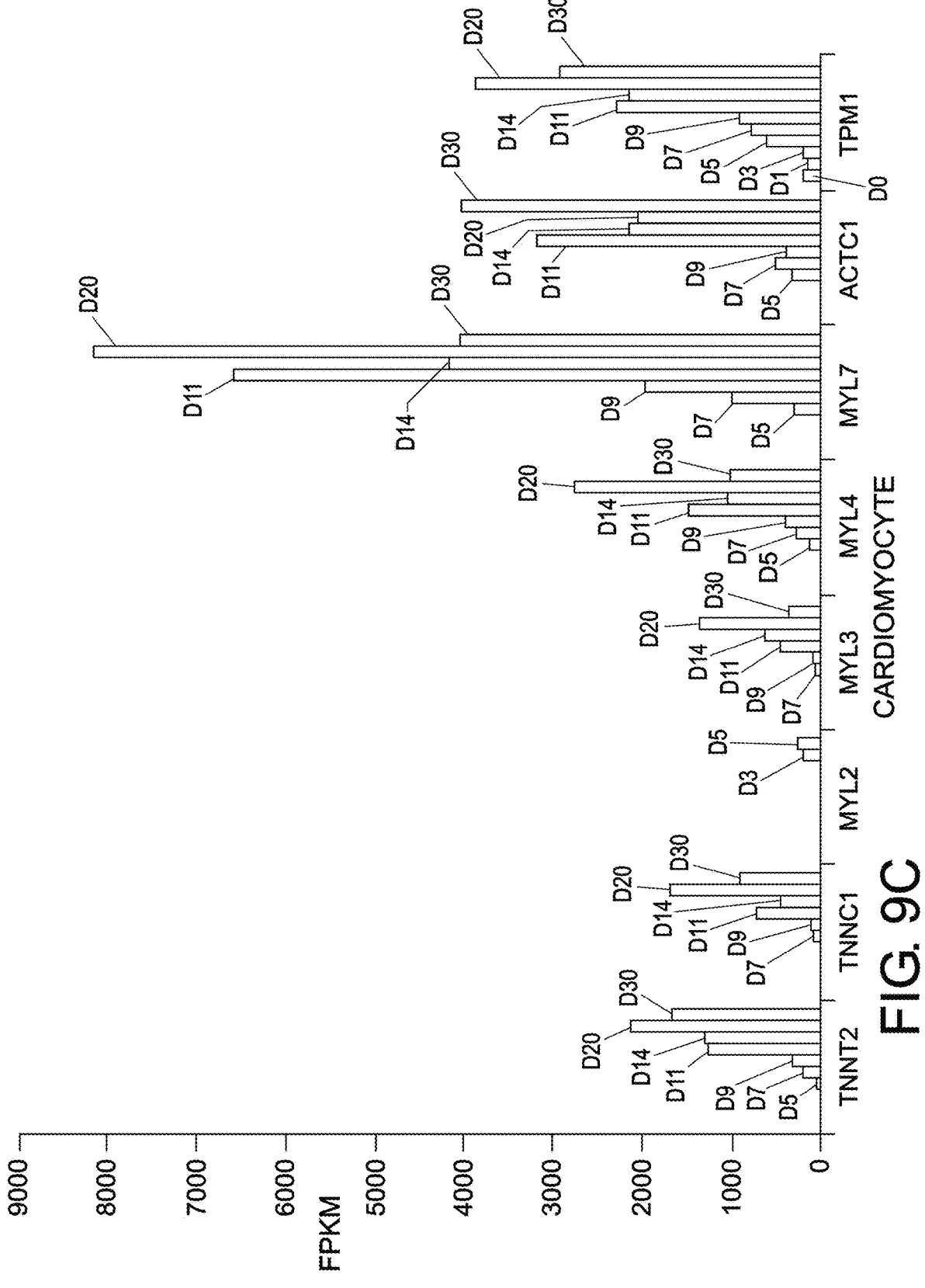

FIG. 9A through FIG. 9C show the levels of various genes during differentiation from days 0 through 30. It is noted that differentiation of cardiomyocytes takes only 14 days, and after that the cells start to mature. These biomarkers can be used to determine how far along in differentiation the stem cells are. FPKM refers to "Fragments Per Kilobase of transcript per Million mapped reads", and is calculated using Cufflinks software. These are relative amounts, which can be used for comparison. As seen in these figures, the amount of LIN28A decreases during differentiation in a relatively linear fashion, as do POU5F1, TDGF1, SALL4, SOX2, UTF1, and LIN28B. The amount of NKX2-5, TNNT2, and MYL3 increase during differentiation. The amounts of NANOG, KIT, ISL1, TNNC1, MYL4, MYL7, ACTC1, and TPM1 increase and peak, then decrease during the 14-day period for differentiation. In FIG. 9C, the amounts of TNNC1, MYL4, MYL7, ACTC1, and TPM1 peak on day 11 of the 14-day differentiation period.

More specifically, the amount of POU5F1 is much greater than LIN28A between days D0 and D3, but then the amount of LIN28A is greater than POU5F1 from days D5 to D14. Similarly, the amount of KIT is greater than ISL1 for days D0 through D7, but the amount of ISL1 is greater than KIT for days D9 through D14. The amount of NKX2-5 is less than ISL1 or KIT up through day D5, but is then greater than both for days D7 through D14. By Day D9, the level of MYL7 is more than twice the level of the proteins MYL3 and MYL4.

The cell culture substrate is used in combination with a cell culture medium. The cell culture medium of the present disclosure is particularly suitable for being used with a substrate that contains (i) laminin-521 or laminin-511 and (ii) laminin-221 or laminin-211. Laminins LN-511 and LN-521 activate α6β1 integrins, which in turn leads to activation of the PI3K/Akt pathway. This supports the pluripotency, self-renewal, and/or proliferation of the differentiated cells. It is contemplated that the substrate may consist of laminin-521 or laminin-511, either intact, as separate chains, or as fragments thereof. Recombinant laminin-521 and recombinant laminin-511 are commercially available. Many different molecules can activate the PI3K/Akt pathway, though with different efficiencies. For example, TGF beta 1 and bFGF activate this pathway. The use of laminin-521 and/or laminin-511 allows the quantity of such molecules to be reduced in the cell culture medium. Laminin-521 conveys the highest dose of signal via α6β1 integrin, activating the PI3K/Akt pathway. The use of laminin-521 allows for single-cell suspension passaging without the addition of cell-detrimental ROCK inhibitor to increase cell survival after single-cell enzymatic dissociation. Addition of the most abundant cardiomyocyte laminin, LN-221, provides signals that direct the pluripotent hESCs towards the cardiomyocyte lineage, but the mechanism is still unknown.

Typically, cell culture media include a large number and a large amount of various growth factors and cytokines to inhibit differentiation and improve proliferation. One advantage of the cell culture medium of the present disclosure is that it does not contain as many growth factors or cytokines, or such high amounts.

Very generally, the cell culture medium of the present disclosure requires lower amounts of basic fibroblast growth factor (bFGF) than typically used. It is possible that growth promoting domains of the laminin molecules are responsible for this effect. It is contemplated that the cell culture medium may comprise from greater than zero to 3.9 nanograms per milliliter (ng/mL) of bFGF. The bFGF is human bFGF so that the cell culture medium is totally human and defined. In some more specific embodiments, the cell culture medium may comprise 3.5 or lower ng/mL of bFGF. In other embodiments, the cell culture medium may comprise from 0.5 to 3.5 ng/mL of bFGF. In some embodiments, the cell culture medium may have zero bFGF, i.e. no bFGF is present.

Generally, the cell culture medium includes a liquid phase in which at least one inorganic salt, at least one trace mineral, at least one energy substrate, at least one lipid, at least one amino acid, at least one vitamin, and at least one growth factor (besides bFGF) are dissolved. Table 1 below includes a list of various such ingredients which may be present in the cell culture medium of the present disclosure, and the minimum and maximum concentrations if the ingredient is present. The values are presented in scientific notation. For example, "4.1E-01" should be interpreted as $4.1 \times 10^{-01}$.

TABLE 1

| Ingredient | molar mass (g/mol) | Min. Conc. (mM) | Max. Conc. (mM) | Min. Conc. (ng/mL) | Max. Conc. (ng/mL) |
|---|---|---|---|---|---|
| INORGANIC SALTS | | | | | |
| Calcium chloride (Anhydrous) | 110.98 | 4.1E-01 | 1.6E+00 | 4.6E+04 | 1.8E+05 |
| HEPES | 238.3 | 5.9E+00 | 1.8E+01 | 1.4E+06 | 4.2E+06 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| Lithium Chloride (LiCl) | 42.39 | 4.9E−01 | 1.5E+00 | 2.1E+04 | 6.2E+04 |
| Magnesium chloride (Anhydrous) | 95.21 | 1.2E−01 | 3.6E−01 | 1.1E+04 | 3.4E+04 |
| Magnesium Sulfate (MgSO$_4$) | 120.37 | 1.6E−01 | 4.8E−01 | 1.9E+04 | 5.8E+04 |
| Potassium chloride (KCl) | 74.55 | 1.6E+00 | 4.9E+00 | 1.2E+05 | 3.6E+05 |
| Sodium bicarbonate (NaHCO$_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E−01 | 5.9E−01 | 2.8E+04 | 8.3E+04 |
| Sodium phosphate, monobasic monohydrate (NaH$_2$PO$_4$—H$_2$O) | 137.99 | 1.8E−01 | 5.3E−01 | 2.4E+04 | 7.3E+04 |
| TRACE MINERALS | | | | | |
| Ferric Nitrate (Fe(NO$_3$)$_3$—9H$_2$O) | 404 | 4.9E−05 | 1.9E−04 | 2.0E+01 | 7.5E+01 |
| Ferrous sulfate heptahydrate (FeSO$_4$—7H$_2$O) | 278.01 | 5.9E−04 | 1.8E−03 | 1.6E+02 | 4.9E+02 |
| Copper(II) sulfate pentahydrate (CuSO$_4$—5H$_2$O) | 249.69 | 2.0E−06 | 8.0E−06 | 5.1E−01 | 2.0E+00 |
| Zinc sulfate heptahydrate (ZnSO$_4$—7H$_2$O) | 287.56 | 5.9E−04 | 1.8E−03 | 1.7E+02 | 5.1E+02 |
| Ammonium Metavanadate NH$_4$VO$_3$ | 116.98 | 5.5E−06 | 1.6E−05 | 6.4E−01 | 1.9E+00 |
| Manganese Sulfate monohydrate (MnSO$_4$—H$_2$O) | 169.02 | 9.9E−07 | 3.0E−06 | 1.7E−01 | 5.0E−01 |
| NiSO$_4$—6H$_2$O | 262.85 | 4.9E−07 | 1.5E−06 | 1.3E−01 | 3.8E−01 |
| Selenium | 78.96 | 8.9E−05 | 2.7E−04 | 7.0E+00 | 2.1E+01 |
| Sodium Meta Silicate Na$_2$SiO$_3$—9H$_2$O | 284.2 | 4.8E−04 | 1.4E−03 | 1.4E+02 | 4.1E+02 |
| SnCl$_2$ | 189.62 | 6.2E−07 | 1.9E−06 | 1.2E−01 | 3.5E−01 |
| Molybdic Acid, Ammonium salt | 1235.86 | 9.9E−07 | 3.0E−06 | 1.2E+00 | 3.7E+00 |
| CdCl$_2$ | 183.32 | 6.1E−06 | 1.8E−05 | 1.1E+00 | 3.4E+00 |
| CrCl$_3$ | 158.36 | 9.9E−07 | 3.0E−06 | 1.6E−01 | 4.7E−01 |
| AgNO$_3$ | 169.87 | 4.9E−07 | 1.5E−06 | 8.3E−02 | 2.5E−01 |
| AlCl$_3$—6H$_2$O | 241.43 | 2.4E−06 | 7.3E−06 | 5.9E−01 | 1.8E+00 |
| Barium Acetate (Ba(C$_2$H$_3$O$_2$)$_2$) | 255.42 | 4.9E−06 | 1.5E−05 | 1.3E+00 | 3.8E+00 |
| CoCl$_2$—6H$_2$O | 237.93 | 4.9E−06 | 1.5E−05 | 1.2E+00 | 3.5E+00 |
| GeO$_2$ | 104.64 | 2.5E−06 | 7.5E−06 | 2.6E−01 | 7.8E−01 |
| KBr | 119 | 4.9E−07 | 1.5E−06 | 5.9E−02 | 1.8E−01 |
| KI | 166 | 5.0E−07 | 1.5E−06 | 8.3E−02 | 2.5E−01 |
| NaF | 41.99 | 4.9E−05 | 1.5E−04 | 2.1E+00 | 6.2E+00 |
| RbCl | 120.92 | 4.9E−06 | 1.5E−05 | 5.9E−01 | 1.8E+00 |
| ZrOCl$_2$—8H$_2$O | 178.13 | 4.9E−06 | 1.5E−05 | 8.7E−01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E−01 | 5.9E−01 | 2.2E+04 | 6.5E+04 |
| LIPIDS | | | | | |
| Linoleic Acid | 280.45 | 9.4E−05 | 2.8E−04 | 2.6E+01 | 7.9E+01 |
| Lipoic Acid | 206.33 | 2.0E−04 | 7.8E−04 | 4.1E+01 | 1.6E+02 |
| Arachidonic Acid | 304.47 | 6.5E−06 | 1.9E−05 | 2.0E+00 | 5.9E+00 |
| Cholesterol | 386.65 | 5.6E−04 | 1.7E−03 | 2.2E+02 | 6.5E+02 |
| DL-alpha tocopherol-acetate | 472.74 | 1.5E−04 | 4.4E−04 | 6.9E+01 | 2.1E+02 |
| Linolenic Acid | 278.43 | 3.5E−05 | 1.0E−04 | 9.7E+00 | 2.9E+01 |
| Myristic Acid | 228.37 | 4.3E−05 | 1.3E−04 | 9.8E+00 | 2.9E+01 |
| Oleic Acid | 282.46 | 3.5E−05 | 1.0E−04 | 9.8E+00 | 2.9E+01 |
| Palmitic Acid | 256.42 | 3.8E−05 | 1.1E−04 | 9.8E+00 | 2.9E+01 |
| Palmitoleic acid | 254.408 | 3.9E−05 | 1.2E−04 | 9.8E+00 | 2.9E+01 |
| Stearic Acid | 284.48 | 3.4E−05 | 1.0E−04 | 9.8E+00 | 2.9E+01 |
| AMINO ACIDS | | | | | |
| L-Alanine | 89.09 | 2.5E−02 | 2.1E−01 | 2.2E+03 | 1.8E+04 |
| L-Arginine hydrochloride | 147.2 | 2.7E−01 | 1.5E+00 | 4.0E+04 | 2.2E+05 |
| L-Asparagine-H$_2$O | 150.13 | 5.0E−02 | 2.1E−01 | 7.5E+03 | 3.1E+04 |
| L-Aspartic acid | 133.1 | 2.5E−02 | 2.1E−01 | 3.3E+03 | 2.7E+04 |
| L-Cysteine-HCl—H$_2$O | 175.63 | 3.9E−02 | 1.2E−01 | 6.9E+03 | 2.1E+04 |
| L-Cystine dihydrochloride | 313.22 | 3.9E−02 | 1.2E−01 | 1.2E+04 | 3.7E+04 |
| L-Glutamic acid | 147.13 | 2.5E−02 | 2.1E−01 | 3.7E+03 | 3.0E+04 |
| L-Glutamine | 146.15 | 1.5E+00 | 4.4E+00 | 2.1E+05 | 6.4E+05 |
| Glycine | 75.07 | 1.5E−01 | 4.4E−01 | 1.1E+04 | 3.3E+04 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| L-Histidine monohydrochloride monohydrate | 209.63 | 5.9E−02 | 1.8E−01 | 1.2E+04 | 3.7E+04 |
| L-Isoleucine | 131.17 | 1.6E−01 | 4.9E−01 | 2.1E+04 | 6.4E+04 |
| L-Leucine | 131.17 | 1.8E−01 | 5.3E−01 | 2.3E+04 | 7.0E+04 |
| L-Lysine hydrochloride | 182.65 | 2.0E−01 | 5.9E−01 | 3.6E+04 | 1.1E+05 |
| L-Methionine | 149.21 | 4.5E−02 | 1.4E−01 | 6.8E+03 | 2.0E+04 |
| L-Phenylalanine | 165.19 | 8.5E−02 | 2.5E−01 | 1.4E+04 | 4.2E+04 |
| L-Proline | 115.13 | 1.1E−01 | 3.2E−01 | 1.2E+04 | 3.7E+04 |
| L-Serine | 105.09 | 1.5E−01 | 4.4E−01 | 1.5E+04 | 4.6E+04 |
| L-Threonine | 119.12 | 1.8E−01 | 5.3E−01 | 2.1E+04 | 6.3E+04 |
| L-Tryptophan | 204.23 | 1.7E−02 | 5.2E−02 | 3.5E+03 | 1.1E+04 |
| L-Tyrosine disodium salt hydrate | 225.15 | 8.4E−02 | 3.7E−01 | 1.9E+04 | 8.4E+04 |
| L-Valine | 117.15 | 1.8E−01 | 5.3E−01 | 2.1E+04 | 6.2E+04 |
| VITAMINS | | | | | |
| Ascorbic acid | 176.12 | 1.3E−01 | 3.8E−01 | 2.2E+04 | 6.7E+04 |
| Biotin | 244.31 | 5.6E−06 | 1.7E−05 | 1.4E+00 | 4.1E+00 |
| B$_{12}$ | 1355.37 | 2.0E−04 | 5.9E−04 | 2.7E+02 | 8.0E+02 |
| Choline chloride | 139.62 | 2.5E−02 | 7.5E−02 | 3.5E+03 | 1.1E+04 |
| D-Calcium pantothenate | 238.27 | 1.8E−03 | 1.4E−02 | 4.4E+02 | 3.4E+03 |
| Folic acid | 441.4 | 2.4E−03 | 7.1E−03 | 1.0E+03 | 3.1E+03 |
| i-Inositol | 180.16 | 2.7E−02 | 1.1E−01 | 4.9E+03 | 1.9E+04 |
| Niacinamide | 122.12 | 6.5E−03 | 2.0E−02 | 7.9E+02 | 2.4E+03 |
| Pyridoxine hydrochloride | 205.64 | 3.8E−03 | 1.1E−02 | 7.8E+02 | 2.4E+03 |
| Riboflavin | 376.36 | 2.3E−04 | 6.8E−04 | 8.6E+01 | 2.6E+02 |
| Thiamine hydrochloride | 337.27 | 3.3E−03 | 3.6E−02 | 1.1E+03 | 1.2E+04 |
| GROWTH FACTORS/PROTEINS | | | | | |
| GABA | 103.12 | 0 | 1.5E+00 | 0 | 1.5E+05 |
| Pipecolic Acid | 129 | 0 | 1.5E−03 | 0 | 1.9E+02 |
| bFGF | 18000 | 0 | 2.17E−07 | 0 | 3.9E+00 |
| TGF beta 1 | 25000 | 0 | 3.5E−08 | 0 | 8.8E−01 |
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferrin or a transferrin substitute. However, in more specific embodiments, it is contemplated that the cell culture medium may not contain (1) insulin or insulin substitute, or (2) transferrin or transferrin substitute, or any combination of these two components. Alternatively, in other embodiments, it is contemplated that the cell culture medium may contain (1) insulin or insulin substitute, or (2) transferrin or transferrin substitute, or any combination of these two components.

It should be noted that other cell culture media may contain growth factors such as interleukin-1 beta (IL-1β or catabolin), interleukin-6 (IL6), or pigment epithelium derived factor (PEDF). Such growth factors are not present in the cell culture medium of the present disclosure.

One specific formula for a cell culture medium is provided in Table 2:

TABLE 2

| Ingredient | Amount | Unit |
|---|---|---|
| bFGF | 0.39 | microgram (µg) |
| Albumin | 1.34 | milligram (mg) |
| Insulin | 2 | mg |
| Lithium Chloride | 4.23 | mg |
| GABA | 0.01 | mg |
| TGF beta 1 | 0.06 | µg |
| Pipecolic acid | 0.013 | mg |
| L-glutamine | 2.92 | grams |
| MEM non-essential amino acid solution | 1 | mL |
| DMEM/F12 | 100 | mL |

In this regard, MEM non-essential amino acid solution is typically provided in a 100× concentrate. The MEM of Table 2 is used after dilution back to 1×, and contains the following amino acids in the following concentration listed in Table 3:

TABLE 3

| MEM Amino Acids | Concentration (ng/mL) |
|---|---|
| Glycine | 7.50E+03 |
| L-Alanine | 8.90E+03 |
| L-Asparagine | 1.32E+04 |
| L-Aspartic acid | 1.33E+04 |
| L-Proline | 1.15E+04 |
| L-Serine | 1.05E+04 |

DMEM/F12 contains the following ingredients listed in Table 4:

TABLE 4

| DMEM/F12 Ingredients | Concentration (ng/mL) |
|---|---|
| Glycine | 187.5 |
| L-Alanine | 44.5 |
| L-Arginine hydrochloride | 1475 |
| L-Asparagine-$H_2O$ | 75 |
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |

TABLE 4-continued

| DMEM/F12 Ingredients | Concentration (ng/mL) |
|---|---|
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$—$5H_2O$) | 0.013 |
| Ferric Nitrate ($Fe(NO_3)_3$—$9H_2O$) | 0.5 |
| Ferric sulfate ($FeSO_4$—$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$—$H_2O$) | 625 |
| Zinc sulfate ($ZnSO_4$—$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |
| Putrescine 2HCl | 0.81 |
| Sodium Pyruvate | 550 |
| Thymidine | 3.65 |

In particular, the cell culture medium may have an albumin concentration of at least 0.3 millimolar (mM). Table 5 below provides a formulation for a cell culture medium containing additional albumin.

In particular embodiments, the amount of human serum albumin (HSA) can be varied from a concentration of 0.195 mM to 1 mM, including from 0.3 mM to 1 mM or from 0.3 mM to about 0.4 mM. The amount of bFGF can also be varied from 0 to about 105 ng/mL, or from 0 to 3.9 ng/mL, or from 0.5 ng/mL to 3.5 ng/mL. These two variations in the amount of HSA and bFGF may occur independently or together.

TABLE 5 mTeSR1 formulation.

| mTeSR1 Ingredient | molar mass (g/mol) | Concentration (ng/mL) | Concentration (mM) |
|---|---|---|---|
| INORGANIC SALTS | | | |
| Calcium chloride (Anhydrous) | 110.98 | 9.14E+04 | 8.24E−01 |
| HEPES | 238.3 | 2.81E+06 | 1.18E+01 |
| Lithium Chloride (LiCl) | 42.39 | 4.15E+04 | 9.80E−01 |
| Magnesium chloride (Anhydrous) | 95.21 | 2.26E+04 | 2.37E−01 |
| Magnesium Sulfate ($MgSO_4$) | 120.37 | 3.84E+04 | 3.19E−01 |
| Potassium chloride (KCl) | 74.55 | 2.43E+05 | 3.26E+00 |
| Sodium bicarbonate ($NaHCO_3$) | 84.01 | 1.51E+06 | 1.80E+01 |
| Sodium chloride (NaCl) | 58.44 | 5.53E+06 | 9.46E+01 |
| Sodium phosphate, dibasic (Anhydrous) | 141.96 | 5.56E+04 | 3.92E−01 |
| Sodium phosphate, monobasic monohydrate ($NaH_2PO_4$—$H_2O$) | 137.99 | 4.90E+04 | 3.55E−01 |
| TRACE MINERALS | | | |
| Ferric Nitrate ($Fe(NO_3)_3$—$9H_2O$) | 404 | 3.92E+01 | 9.71E−05 |
| Ferrous sulfate heptahydrate ($FeSO_4$—$7H_2O$) | 278.01 | 3.28E+02 | 1.18E−03 |
| Copper(II) sulfate pentahydrate ($CuSO_4$—$5H_2O$) | 249.69 | 1.02E+00 | 4.08E−06 |
| Zinc sulfate heptahydrate ($ZnSO_4$—$7H_2O$) | 287.56 | 3.39E+02 | 1.18E−03 |
| Ammonium Metavanadate $NH_4VO_3$ | 116.98 | 1.28E+00 | 1.09E−05 |

TABLE 5-continued mTeSR1 formulation.

| mTeSR1 Ingredient | molar mass (g/mol) | Concentration (ng/mL) | Concentration (mM) |
|---|---|---|---|
| Manganese Sulfate monohydrate (MnSO$_4$—H$_2$O) | 169.02 | 3.33E−01 | 1.97E−06 |
| NiSO$_4$—6H$_2$O | 262.85 | 2.55E−01 | 9.70E−07 |
| Selenium | 78.96 | 1.40E+01 | 1.77E−04 |
| Sodium Meta Silicate Na$_2$SiO$_3$ 9H$_2$O | 284.2 | 2.75E+02 | 9.66E−04 |
| SnCl$_2$ | 189.62 | 2.35E−01 | 1.24E−06 |
| Molybdic Acid, Ammonium salt | 1235.86 | 2.43E+00 | 1.97E−06 |
| CdCl$_2$ | 183.32 | 2.24E+00 | 1.22E−05 |
| CrCl$_3$ | 158.36 | 3.14E−01 | 1.98E−06 |
| AgNO$_3$ | 169.87 | 1.67E−01 | 9.81E−07 |
| AlCl$_3$ 6H$_2$O | 241.43 | 1.18E+00 | 4.87E−06 |
| Barium Acetate (Ba(C$_2$H$_3$O$_2$)$_2$) | 255.42 | 2.50E+00 | 9.79E−06 |
| CoCl$_2$ 6H$_2$O | 237.93 | 2.33E+00 | 9.81E−06 |
| GeO$_2$ | 104.64 | 5.20E−01 | 4.97E−06 |
| KBr | 119 | 1.18E−01 | 9.89E−07 |
| KI | 166 | 1.66E−01 | 1.00E−06 |
| NaF | 41.99 | 4.13E+00 | 9.83E−05 |
| RbCl | 120.92 | 1.19E+00 | 9.81E−06 |
| ZrOCl$_2$ 8H$_2$O | 178.13 | 1.75E+00 | 9.80E−06 |
| ENERGY SUBSTRATES | | | |
| D-Glucose | 180.16 | 2.47E+06 | 1.37E+01 |
| Sodium Pyruvate | 110.04 | 4.31E+04 | 3.92E−01 |
| LIPIDS | | | |
| Linoleic Acid | 280.45 | 5.27E+01 | 1.88E−04 |
| Lipoic Acid | 206.33 | 8.25E+01 | 4.00E−04 |
| Arachidonic Acid | 304.47 | 3.93E+00 | 1.29E−05 |
| Cholesterol | 386.65 | 4.33E+02 | 1.12E−03 |
| DL-alpha tocopherol-acetate | 472.74 | 1.37E+02 | 2.90E−04 |
| Linolenic Acid | 278.43 | 1.95E+01 | 6.99E−05 |
| Myristic Acid | 228.37 | 1.96E+01 | 8.59E−05 |
| Oleic Acid | 282.46 | 1.96E+01 | 6.94E−05 |
| Palmitic Acid | 256.42 | 1.96E+01 | 7.65E−05 |
| Palmitoleic acid | 254.408 | 1.96E+01 | 7.71E−05 |
| Stearic Acid | 284.48 | 1.96E+01 | 6.89E−05 |
| AMINO ACIDS | | | |
| L-Alanine | 89.09 | 1.22E+04 | 1.37E−01 |
| L-Arginine hydrochloride | 147.2 | 8.07E+04 | 5.48E−01 |
| L-Asparagine-H$_2$O | 150.13 | 2.06E+04 | 1.37E−01 |
| L-Aspartic acid | 133.1 | 1.82E+04 | 1.37E−01 |
| L-Cysteine-HCl—H$_2$O | 175.63 | 1.38E+04 | 7.83E−02 |
| L-Cystine dihydrochloride | 313.22 | 2.45E+04 | 7.83E−02 |
| L-Glutamic acid | 147.13 | 2.02E+04 | 1.37E−01 |
| L-Glutamine | 146.15 | 4.30E+05 | 2.94E+00 |
| Glycine | 75.07 | 2.21E+04 | 2.94E−01 |
| L-Histidine monohydrochloride monohydrate | 209.63 | 2.47E+04 | 1.18E−01 |
| L-Isoleucine | 131.17 | 4.28E+04 | 3.26E−01 |
| L-Leucine | 131.17 | 4.64E+04 | 3.54E−01 |
| L-Lysine hydrochloride | 182.65 | 7.14E+04 | 3.91E−01 |
| L-Methionine | 149.21 | 1.35E+04 | 9.06E−02 |
| L-Phenylalanine | 165.19 | 2.79E+04 | 1.69E−01 |
| L-Proline | 115.13 | 2.49E+04 | 2.16E−01 |
| L-Serine | 105.09 | 3.09E+04 | 2.94E−01 |
| L-Threonine | 119.12 | 4.19E+04 | 3.52E−01 |
| L-Tryptophan | 204.23 | 7.07E+03 | 3.46E−02 |
| L-Tyrosine disodium salt hydrate | 225.15 | 3.78E+04 | 1.68E−01 |
| L-Valine | 117.15 | 4.16E+04 | 3.55E−01 |
| VITAMINS | | | |
| Ascorbic acid | 176.12 | 4.46E+04 | 2.53E−01 |
| Biotin | 244.31 | 2.74E+00 | 1.12E−05 |
| B12 | 1355.37 | 5.34E+02 | 3.94E−04 |
| Choline chloride | 139.62 | 7.02E+03 | 5.03E−02 |
| D-Calcium pantothenate | 238.27 | 8.79E+02 | 3.69E−03 |
| Folic acid | 441.4 | 2.08E+03 | 4.71E−03 |
| i-Inositol | 180.16 | 9.89E+03 | 5.49E−02 |
| Niacinamide | 122.12 | 1.59E+03 | 1.30E−02 |

TABLE 5-continued mTeSR1 formulation.

| mTeSR1 Ingredient | molar mass (g/mol) | Concentration (ng/mL) | Concentration (mM) |
|---|---|---|---|
| Pyridoxine hydrochloride | 205.64 | 1.57E+03 | 7.62E−03 |
| Riboflavin | 376.36 | 1.72E+02 | 4.56E−04 |
| Thiamine hydrochloride | 337.27 | 8.16E+03 | 2.42E−02 |
| GROWTH FACTORS/PROTEINS | | | |
| GABA | 103.12 | 1.01E+05 | 9.79E−01 |
| Pipecolic Acid | 129 | 1.27E+02 | 9.84E−04 |
| bFGF | 18000 | 1.04E+02 | 5.77E−06 |
| TGF beta 1 | 25000 | 5.88E−01 | 2.35E−08 |
| Human Insulin | 5808 | 2.28E+04 | 3.92E−03 |
| Human Holo-Transferrin | 78500 | 1.08E+04 | 1.37E−04 |
| Human Serum Albumin | 67000 | 1.31E+07 | 1.95E−01 |
| Glutathione (reduced) | 307.32 | 1.96E+03 | 6.38E−03 |
| OTHER COMPONENTS | | | |
| Hypoxanthine Na | 136.11 | 1.61E+03 | 1.18E−02 |
| Phenol red | 354.38 | 5.99E+03 | 1.69E−02 |
| Putrescine-2HCl | 161.07 | 6.36E+01 | 3.95E−04 |
| Thymidine | 242.229 | 2.86E+02 | 1.18E−03 |
| 2-mercaptoethanol | 78.13 | 7.66E+03 | 9.80E−02 |
| Pluronic F-68 | 8400 | 1.96E+05 | 2.33E−02 |
| Tween 80 | 1310 | 4.31E+02 | 3.29E−04 |

The combination of the laminin substrate with the cell culture medium of the present disclosure results in a cell culture system that can be cheaper yet provides higher efficiency in maintaining differentiated cells. In essence, all that is required is specific laminins and a minimal amount of nutrition. It is particularly contemplated that the laminin used in combination with this cell culture medium is either LN-511 or LN-521 in combination with LN-221 or LN-211.

The cell culture system in some embodiments includes a combination cell culture substrate with (i) one of laminin-221 or LN-211, and (ii) one of laminin-511 or laminin-521, and maintains differentiated human cardiomyocytes longer than shown by conventional fibronectin substrates.

The methods of differentiating cardiomyocytes from pluripotent stem cells as described herein represent the first time that a differentiation protocol for hES cells, which generates in a controllable fashion Islet-1 positive progenitors and then, subsequently, TnT cardiomyocytes that express regular beatings in vitro, has been described. The laminins 521, 511, 221, and 211 used in the method can be produced under GMP conditions such that they form appropriate human substrata for derivation, expansion and differentiation of cells for regenerative medicine. The method can be carried out without the presence of any animal-derived molecules, which is important from the point of view of developing cardiac progenitors and differentiated cardiomyocytes for human cell therapy purposes or for testing the effects of drugs on human cardiomyocytes.

Translation of the method for differentiating cardiomyoctes to industrial applications may include industrial production of GMP quality LN-221. Using the method, it will be possible to produce large quantities of hES cell derived cardiac progenitors and cardiomyocytes required for cell therapy of heart muscle injury. This production of the cells may require culturing on (i) human LN-521 or LN-511 and (ii) LN-221 or LN-211. The method provides significant advances for production of human cardiac progenitor cells and cardiomyocytes for cardiotoxicity and drug testing. The pharmaceutical industry is currently struggling with a low rate of new drug candidates, long discovery processes, increasing developmental costs and high attrition rates during later stages of drug development.

Current cell systems used in research and development are hampered by the fact that primary cells or cell lines either rapidly lose important functional systems, or already lack these properties. This may limit their use for validation of pharmacokinetic properties or predicting unexpected toxicity. Moreover, many human primary cell types, such as cardiomyocytes and neuronal cells, are almost inaccessible for these applications. The animal-based in vivo and in vitro systems used within drug discovery are neither cost effective nor clinically relevant or predictive, due to the low concordance between animal data and man. There is a strong need for new, innovative cell assays with high human relevance where new candidate drugs can be validated. Human pluripotent stem cells which have been effectively differentiated into the functional cells in a reproducible manner possess a virtually unlimited supply of cells with a broad variety of applications, spanning from pharmaceutical development to direct use in human cell therapies.

The following examples are for purposes of further illustrating the present disclosure. The examples are merely illustrative and are not intended to limit devices made in accordance with the disclosure to the materials, conditions, or process parameters set forth therein.

EXAMPLES

Example 1

Identification of LN-521 or LN-511 and LN-221 for Combination Substrate Used in Differentiating Cardiomyocyte Cells The described method for differentiating cardiomyocytes from human pluripotent stem cells includes two specific human laminin isoforms (i) LN-521 or LN-511 and (ii) LN-221 that, based on expression analysis of human heart muscle, could be considered important as cell culture substrata. Based on mRNA analysis, laminin chains, alpha-2, beta-2 and gamma-1 are the most highly expressed alpha, beta and gamma laminin chains in the mature cardiac muscle. The alpha-5 and beta-1 chains are less abundant, and alpha-1, alpha-3, beta-3, beta-4, gamma-2 and gamma-3 exhibit low or no detectable expression. It is therefore hypothesized, without being held to any particular theory that LN-221, which has the highest expression, is of major importance for the development and maintenance of cardiomyocyte phenotype and function.

To test this hypothesis, full-length cDNAs for the human laminin chains, alpha-2, beta-2 and gamma-1, were inserted into human expression vectors after which HEK293 (human embryonic kidney) cells were sequentially transfected, clone-selected and expanded as previously described for LN-511. Further information on the process previously described for LN-511 is found in Doi, M., Thyboll, J., Kortesmaa, J., Jansson, K., Iivanainen, A., Parvardeh, M., Timpl, R., Hedin, U., Swedenborg, J., and Tryggvason, K. 2002. *"Recombinant human laminin-10 (LN-511). Production, purification, and migration-promoting activity on vascular endothelial cells."* J Biol Chem 277:12741-12748, which is incorporated by reference. A cell line expressing high amounts of trimeric LN-221 produced as recombinant was selected for production of LN-221. Recombinant LN-221 was used together with the highly embryonic stem cell-associated LN-521 or LN-511 to explore if LN-221 does support the differentiation of embryonic stem cells into cardiomyocytes. The results demonstrate that by using the specific LN-521 or LN-511 in combination with the highly heart muscle specific LN-221 as cell culture coatings, hES cells could be differentiated first to Islet-1 positive cardiomyocyte progenitor cells and then, after further culturing, to beating cardiomyocytes expressing, e.g., specific biomarkers like TnT. Methods of differentiating cardiac progenitor and mature cardiomyocyte cells from pluripotent stem cells are therefore controllable.

Example 2

Generation of Striated Muscle-like Muscle Fiber

Pluripotent hESCs on LN-521 were maintained using a chemically defined maintenance medium, Nutristem (Stemgent), without the need of ROCK inhibitor. Nutristem contains a low amount of bFGF (4 ng/ml) as compared to mTesR1, which contains an unnecessarily high amount (100 ng/ml) and bovine serum albumin (BSA). Prior to differentiation, $2 \times 10^5$ cells/cm$^2$ were seeded into wells coated overnight with a 50% mixture of (i) LN-521 or LN-511 and (ii) LN-221 (provided by BioLamina).

Without being bound to any particular theory, the rationale is that LN-221 is the most abundant laminin expressed in the ultrathin basement membrane surrounding human heart muscle fibers. The underlying LN-521 or LN-511 may promote cell attachment and proliferation, while LN-221 provides a natural niche for cardiomyocyte formation.

Cells were maintained for 4 days to achieve sub-confluence and at day 0 of differentiation, 12 μM of CHIR 99021 (Tocris) (a GSK-3 inhibitor) was added to differentiation media (RPMI/B27-insulin) for 24 hours to inhibit β-catenin phosphorylation which stimulates canonical Wnt signaling activities. The next day (day 1), media was changed to differentiation media and Brachyury positive cells were allowed to proliferate. On day 3, Wnt activities were inhibited by the application of 5 μM of IWP 2 inhibitor (Tocris) onto the cells; this will promote cardiac mesodermal specification. On day 5, the medium was changed to basal medium (RPMI/B27) after which all subsequent medium changes were every 3 days. Striated muscle-like muscle fiber with regular beating were formed by day 14. These cardiomyocytes are then stained with cardiac specific markers (Troponin T, Troponin I, MF-20) for fluorescence microscopy and flow cytometry. On top of full differentiation, specification of pluripotent cells to Islet-1 positive cardiac progenitors should be complete at day 5, when these cells can be identified and maintained on LN-521.

Example 3

Stabilization and Expansion of Cardiomyocyte Progenitors as Exemplified by Islet-1 and NKX2.5 Positive Cells on LN-511 or LN-521

Maturation of cardiomyocyte progenitors can be stopped and maintained at their differentiation stage (e.g. islet-1 positivity) by placing them on either LN-511 or LN-521 matrix. At day 5 of the differentiation protocol, cells were dissociated with TrypLE buffer and re-plated into new LN-511/LN-521 coated wells with media containing GSK inhibitor which will enhance Wnt signaling, BMP inhibitor and Activin/Nodal inhibitor. Continual passaging of cells at sub-confluence ensures the stabilization and expansion of the highly homogenous progenitor cells.

Immunostaining of the progenitors showed that they are 99% positive for both islet-1 and NKX2.5 transcription factors. These cells can then be passaged at least 6 times such that the cells maintain 99% positivity for those two cardiomyocyte progenitor markers. These progenitors can also be long-term cryopreserved in mFreSR cryopreservation medium in liquid nitrogen. When required, cells can be thawed and they will readily proliferate or differentiate on laminins. These results are important as such progenitors probably render themselves best for cell transplantation in repair of damaged heart muscle.

Example 4

Study Characterizing Cardiomyocyte Progenitor Cells

Cardiac progenitor cells were characterized during differentiation using RNA sequencing, immunocytochemistry, flow cytometry, electrophysiology and cytotoxicity. Cardiac progenitors were detected at days 5 and 7 (after the beginning of differentiation) as confirmed by expression of C-KIT, ISL1, NKX2-5 and other distinctive markers. These progenitors continued to differentiate into spontaneously beating cardiomyocytes, expressing >80% TNNT2, and were considered to be cardiomyocytes after Day 9.

The multipotent cardiomyocyte progenitor cells were then injected into SCID mice. It was hypothesized that the use of multipotent progenitor cells would have higher efficacy than injecting beating fully-differentiated cardiomyocytes for myocardial repair, and would also reduce the risk of arrhythmias.

Reperfusion injuries to the ventricles were created and different fluorescently labeled cardiomyocyte progenitors were injected directly into the damaged myocardium. Survival, proliferation and tracking of the injected cells was monitored by bioluminescence using an IVIS Spectrum imaging system. The bioluminescence signal continued to be detected at 12 weeks, implying long-term survival of these cells. Heart function was assessed by echocardiography at 8 weeks and showed a significant improvement of ejection fraction in treated mice as compared to control mice. Hematoxylin and Eosin staining showed a huge infarct, and immunofluorescence staining showed the presence of human cardiomyocytes in the infarct region as well as integrated into the mouse muscle fibers. This showed the functional regeneration of damaged heart muscles with well-characterized fully defined, xeno-free human cardiomyocyte progenitor cells.

Figure 10A:
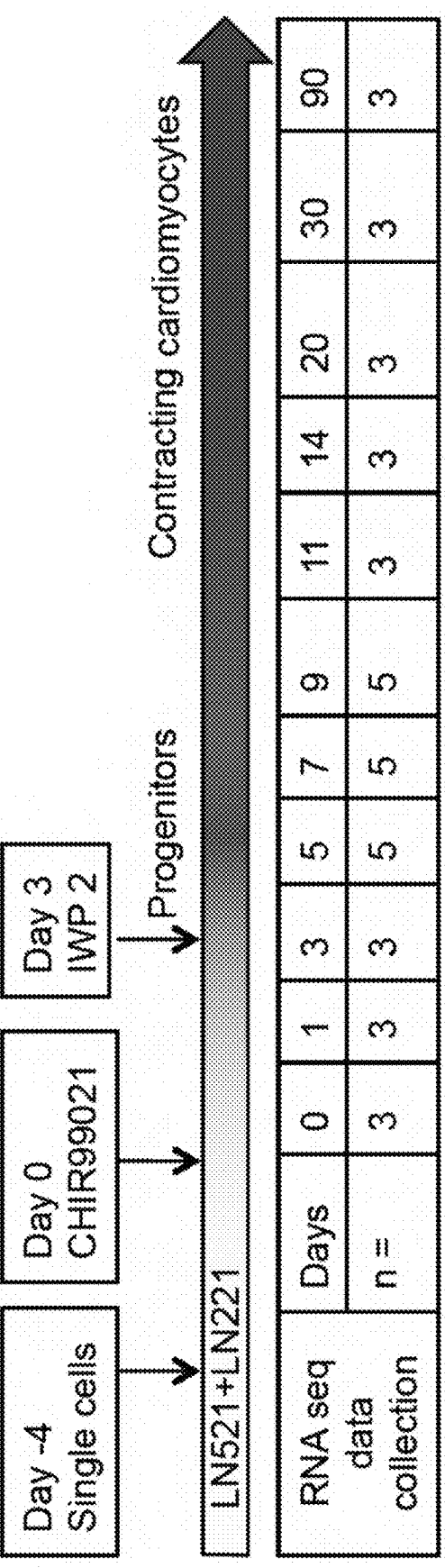
FIG. 10A is a timeline showing a differentiation protocol on a substrate of LN-521 and LN-221.

Cardiomyocyte progenitor cells and cardiomyocytes were cultured using the method illustrated in FIG. 10A. This figure is a timeline showing the differentiation of pluripotent stem cells into cardiomyocyte progenitor cells and cardiomyocytes. The arrow is marked with "LN521+LN221", indicating that the cells are cultured on a substrate containing both LN-521 and LN-221. This timeline is very similar to that illustrated in FIG. 3A. First, pluripotent stem cells from two separate hESC lines (H1 and HS1001) were seeded on a substrate on day –4 and maintained. On Day 0, the pluripotent cells were cultured for one day in the presence of a GSK-3 inhibitor such as CHIR 99021 to further induce Wnt signaling specifying the cells into mesodermal lineage, as confirmed by Brachyury expression. Day 0 also indicates the start of the differentiation process. Then, from Days 1-3, the pluripotent cells were cultured in a basal medium devoid of inhibitor (such as the GSK-3 inhibitor) for two days. On Day 3, the pluripotent cells were cultured for one day with a Wnt inhibitor such as IWP 2 to downregulate the Wnt signaling. Then, on Day 4 and afterwards, the pluripotent cells were cultured in a basal medium devoid of inhibitor (such as the Wnt inhibitor). The cardiomyocyte progenitor cells can be harvested and used for cardiac therapy as soon as Day 5. By Day 10, fully differentiated cardiomyocytes can be obtained. For comparison purposes, this protocol was also performed using a substrate of only LN-521.

Figures 10B, 10C:
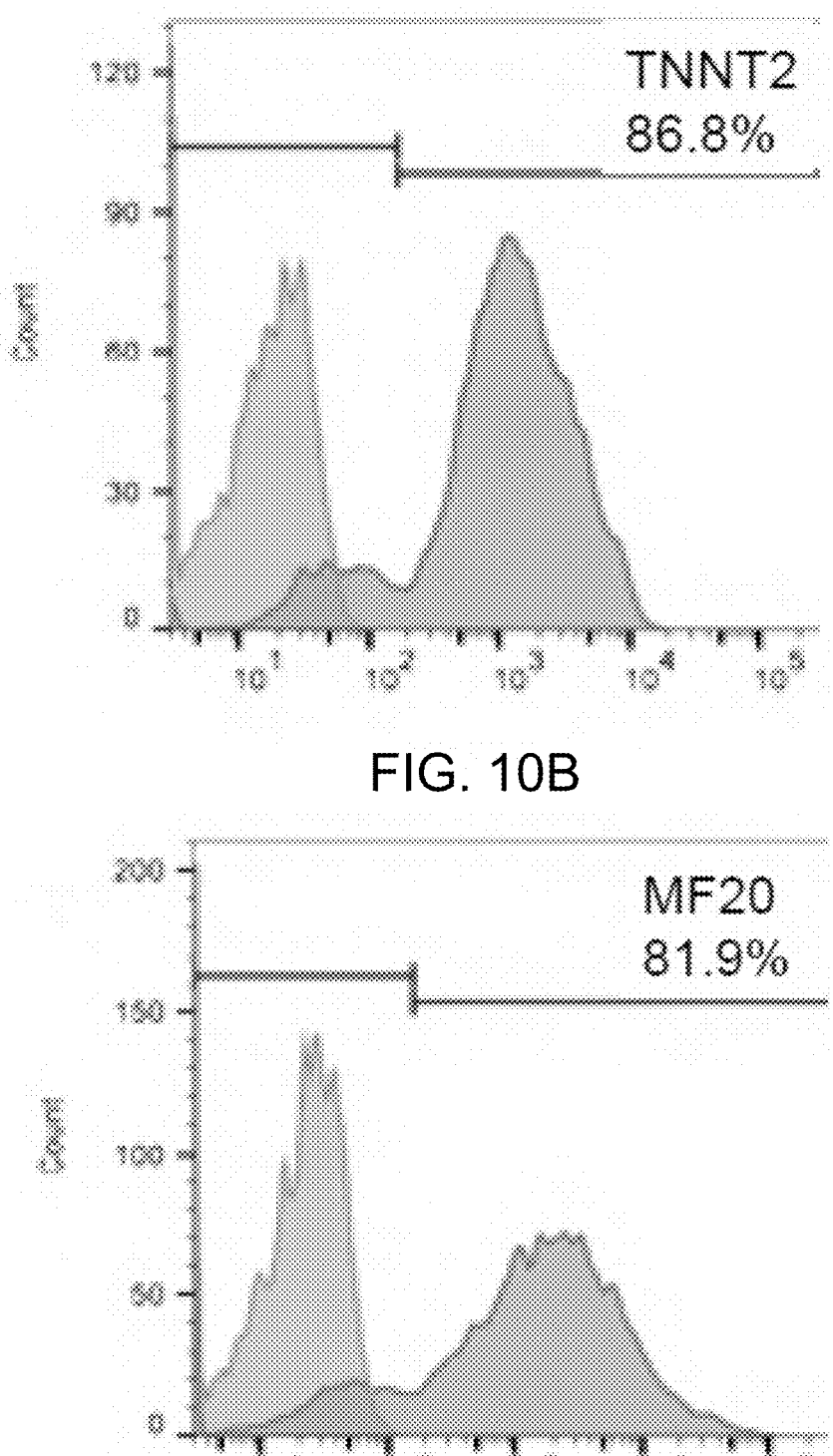
FIG. 10B is a trace of troponin T (TNNT2) flow cytometry for Day 30 cardiomyocytes derived from H1 cell line. The y-axis (count) runs from 0 to 120 in increments of 30. The x-axis is logarithmic, and runs from $10^1$ to $10^5$.
FIG. 10C is a trace of myosin heavy chain (MF20) flow cytometry for Day 30 cardiomyocytes derived from H1 cell line. The y-axis (count) runs from 0 to 200 in increments of 50. The x-axis is logarithmic, and runs from $10^1$ to $10^5$.

FIG. 10B and FIG. 10C are representative traces of TNNT2 and MF20 flow cytometry for day 30 cardiomyocytes derived from the H1 cell line. They revealed an 86.8% and 81.9% population of cardiomyocytes, respectively.

Figure 10D:
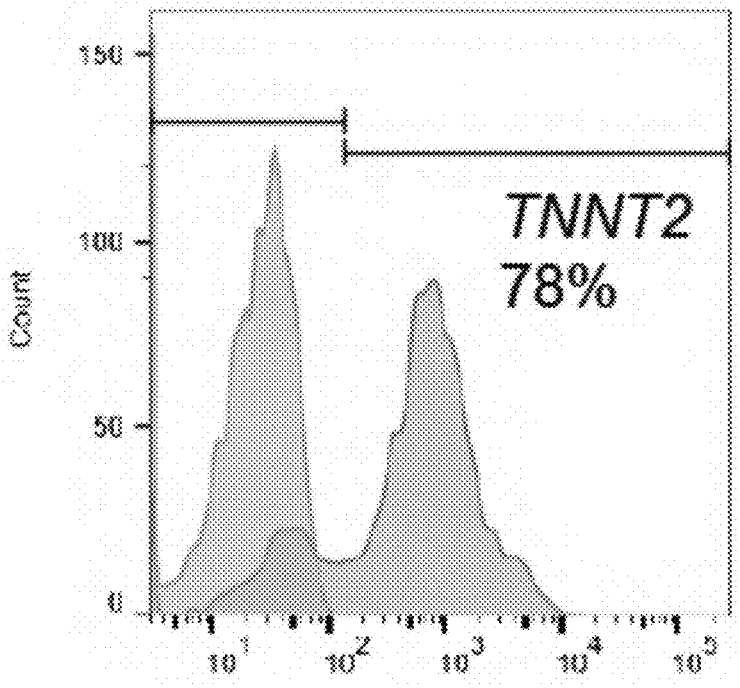
FIG. 10D is a trace of troponin T (TNNT2) flow cytometry for Day 30 cardiomyocytes derived from HS1001 cell line. The y-axis (count) runs from 0 to 150 in increments of 50. The x-axis is logarithmic, and runs from $10^1$ to $10^5$.
Figure 10E:
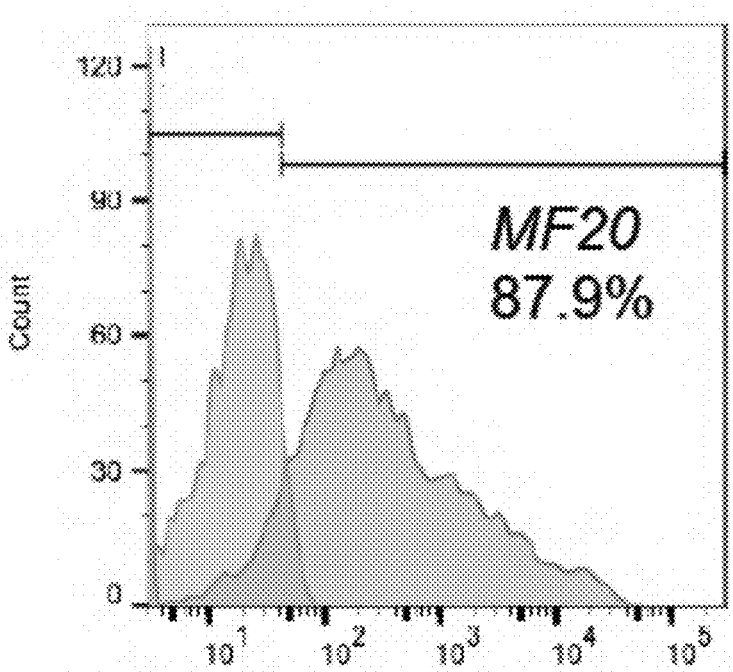
FIG. 10E is a trace of myosin heavy chain (MF20) flow cytometry for Day 30 cardiomyocytes derived from HS1001 cell line. The y-axis (count) runs from 0 to 120 in increments of 30. The x-axis is logarithmic, and runs from $10^1$ to $10^5$.

FIG. 10D and FIG. 10E are representative traces of TNNT2 and MF20 flow cytometry for day 30 cardiomyocytes derived from the HS1001 cell line. They revealed a 78% and 87.9% population of cardiomyocytes, respectively.

Figure 10F:
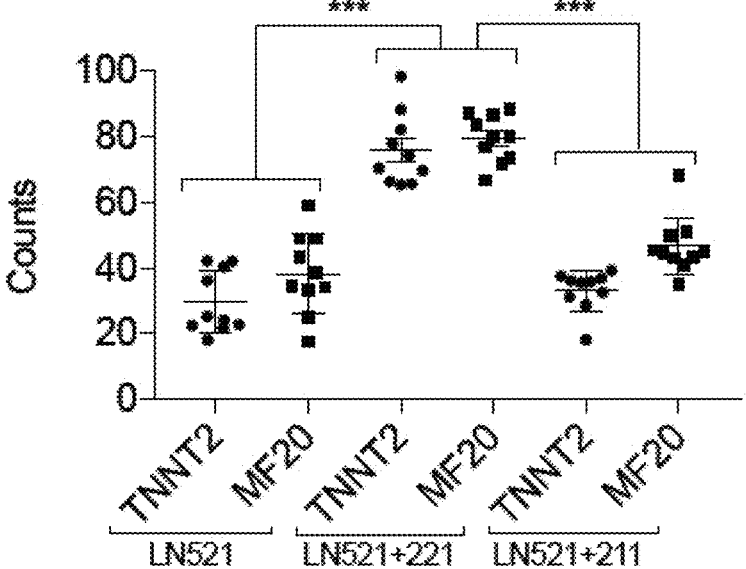
FIG. 10F is a graph showing cardiomyocyte cell count versus three different substrates: LN521 only, LN521+ LN221, and LN521+LN211. The y-axis runs from 0 to 100 in increments of 20.

FIG. 10F is a graph showing the combined flow cytometry measurements of TNNT2 and MF20 in H1 and HS1001 cell lines on three different substrates: only LN-521, LN-521+LN-221 (1:1 weight ratio), and LN-521+LN-211 (1:1 weight ratio). Using the combination of LN-521+LN-221 significantly improved cardiomyocyte production compared to LN-521 alone or LN-521+LN-211.

Figure 10G:
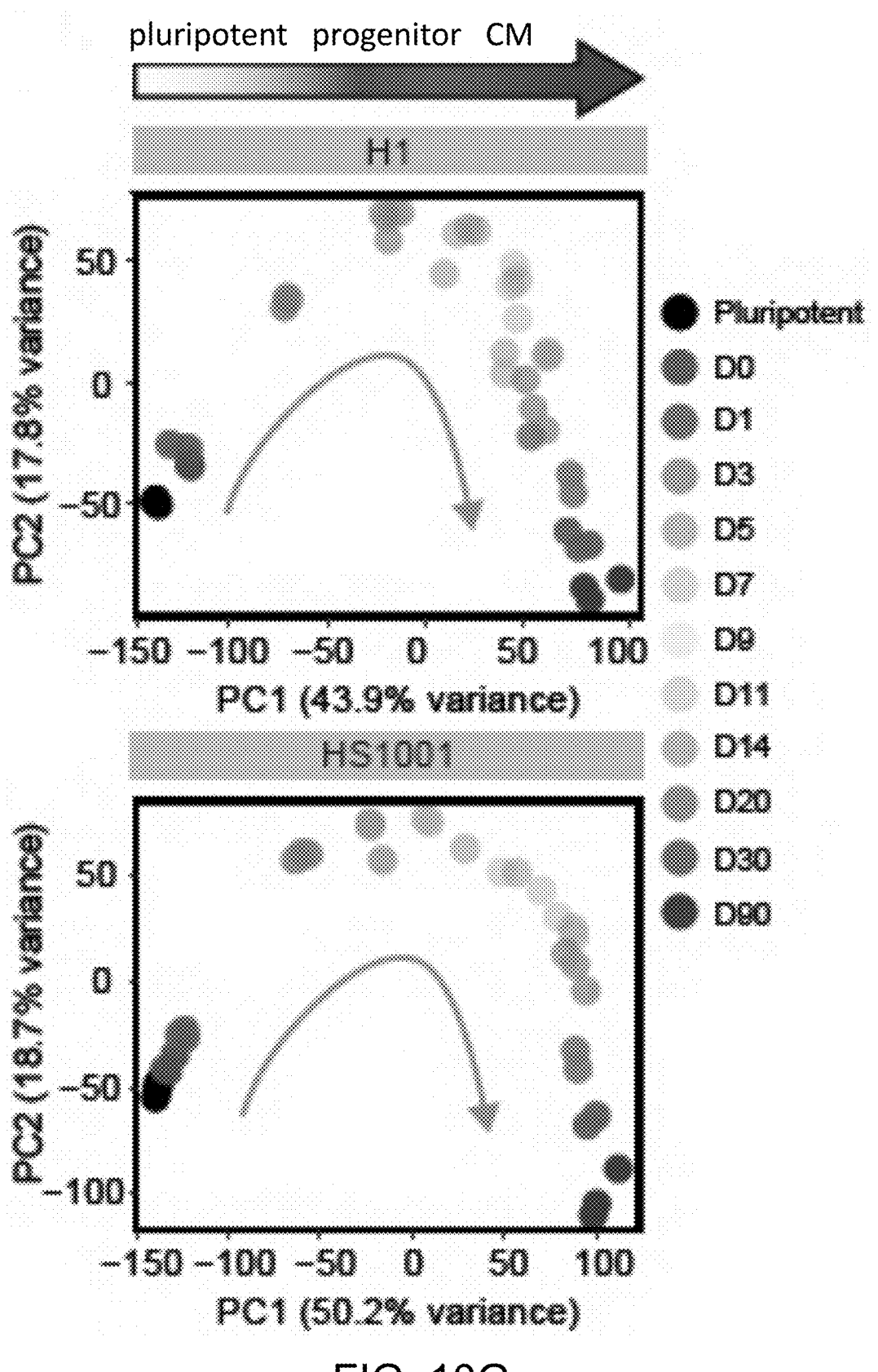
FIG. 10G is a set of two graphs showing the total expression variabilities of the first principal component and the second principal component. The top graph is for the H1 cell line, and the bottom graph is for the HS1001 cell line. For both graphs, the y-axis runs in increments of 50. The top graph runs from −50 to +50, and the bottom graph runs from −100 to +50. For both graphs, the x-axis runs from −150 to +100 in increments of 50. In both graphs, the pluripotent starts at the left, and the D90 ends at the right.

To assess the reproducibility, robustness and characterize global transcriptomic changes occurring during the differentiation protocol, RNA was isolated and RNA-sequencing was performed on the cells throughout the differentiation protocol up to day 90. FIG. 10G shows a principal component analysis (PCA) of this data independently carried out on each cell line. PC1 (x-axis) separates the data by time, and PC2 (y-axis) captures the formation of cardiomyocyte progenitors. This revealed a clear time and cardiac progenitor formation trajectory (captured by PC1 and PC2 respectively) that was followed by both cell lines.

Expression levels for various genes were measured at days 0, 1, 3, 5, 7, 9, 11, 14, 20, 30, 60 and 120 were measured. These are shown in FIG. 11A and FIG. 11B. Progenitor-specific genes were up-regulated, then down-regulated over time. Cardiomyocyte-specific genes were up-regulated over time. In FIG. 11B, cell cycle proteins reduced in expression over the days, suggesting a reduction in proliferation rate and indicating a more mature cardiomyocyte. FIG. 11C is a more detailed analysis of cardiomyocyte marker genes and channel genes, broken down by cell line. The time expression profile of these marker genes suggested cardiomyocyte formation around Day 9 to Day 11, which was also confirmed by the observed phenotypes of cell analyzed by microscopy and immunohistologic methods.

Unidirectional alignment of contracting cells mimicking muscle fibers and/or whole sheet of beating cardiomyocytes (muscle fibrils) were observed in culture plates by Day 20. FIG. 12A is a picture showing sheets of aligned beating cardiomyocytes at day 30. The cell sheets were dissociated and replated onto LN-521+221 coated plates. Single cells in suspension attached and spread on the surface, forming a rectangular, cubodial shaped morphology resembling native cardiomyocytes, as seen in FIG. 12B.

Immunofluorescent staining of the Day 30 cardiomyocytes was performed with Troponin I (TNNI3), TNNT2, α-actinin, and NKX2-5 antibodies, and with DAPI. FIG. 12C was stained with α-actinin (green) and TNNI3 (red) antibodies. FIG. 12D was stained with NKX2-5 (green) and TNNI3 (red) antibodies, and with DAPI (purple). FIG. 12E was stained with TNNT2 antibodies (green) and with DAPI (purple). FIG. 12F was stained with α-actinin antibodies and with DAPI. These clearly showed sarcomeric striations. FIG. 12D also showed the presence of binuclei with NKX2-5 staining, which suggested a mature phenotype.

To further characterize the functionality of the cardiomyocytes, single cell patch clamp and multi-electrode assay (MEA) were utilized to measure their action potential. 13.60% mimicked the nodal subtype, 22.20% mimicked the atrial subtype, and 64.20% mimicked the heart ventricle subtype (see FIG. 8(C)).

Functionality and relevant responses to pharmacological compounds were demonstrated with cell viability assays. As seen in FIG. 12G and FIG. 12H, treatment with valinomycin or emetine dihydrochloride showed that the drugs significantly reduced cell viability with various potencies. The $EC_{50}$ values calculated were 13.1 micromolar ($\mu M$) for valinomycin and 6.079 $\mu M$ for emetine dihydrochloride. This demonstrated the sensitivity of the cells to cytotoxic compounds. Cellular responses to adrenergic stimulation were also tested with MEA. Upon exposure to isoproterenol (a β-adrenoreceptor agonist) and Sotalol (a β-adrenoreceptor blocker), the cardiomyocytes increased heart rate and shortened corrected field potential duration (cFPD) respectively, as expected. In conclusion, the differentiation protocol yielded cardiomyocytes with properties highly similar to those isolated from intact mouse heart muscle.

Next, cardiac progenitor cells on LN-521+LN-221 substrate were harvested at Day 5 and Day 7 of the differentiation protocol, and used for treatment of mice with an ischemic reperfusion injury. About 1 (one) million progenitor cells (either Day 5 or Day 7) were injected in two injection sites per mouse. These progenitor cells had not yet developed into TNNT2 positive beating cardiomyocytes, but did efficiently proliferate in vitro. FIGS. 13A-13F show some of the results of tests using Day 5 cardiomyocyte (CM) progenitors in mice.

Luciferase-labeled Day 5 CM progenitors were injected into the ischemic perfused injured hearts (30 mins ligation of LAD) of the mice. Control mice were injected only with medium. Luciferase signals were detected with the IVIS imaging machine at weeks 4, 8 and 12 suggesting the continual survival of the cells in vivo. No teratoma formation was observed, suggesting that the cardiac progenitor cells were not tumorigenic and were suitable for cell therapy.

At week 12, mice were sacrificed. FIG. 13A shows two pictures, one of a progenitor-injected heart (labeled D5 progenitors) and one of the control mouse injected only with medium (labeled Medium). These pictures show a reduced infarct area in the cardiomyocyte progenitor-treated mice compared to the Medium control.

FIG. 13B is a graph comparing the ejection fraction of the CM progenitor-treated mice (Cells) to the control (Medium) at week 4. FIG. 13C is a graph comparing them at week 8. FIG. 13D is a graph comparing them at week 12. They showed a significant improvement of heart function in the Cells-treated animals at week 4 and week 8. However, at week 12, the differences diminished, suggesting the self-recovery of the hearts over the longer term. Day 5 progenitors were able to improve the ejection fraction for up to 8 weeks, and remained viable and differentiated into cardiomyocytes in the infarcted region.

FIG. 13E is an H&E section on the infarcted heart of a Cells-treated animal at week 12, which showed a significant infarction with the presence of human nuclei (dark spots, see arrows).

FIG. 13F is a set of four immunofluroscence stains of the heart sections with DAPI (blue), KU80 (green, specific for human nuclei), cardiac troponin T (red, for human and mouse troponin T) and a merge image showing the presence of human cardiomyocytes in the infarcted region (see arrows).

To examine whether transplantation of cardiomyocyte progenitors improved contractile activity in the injured region, echocardiograms were taken at weeks 0, 4, 8, and 12. FIG. 14 is a set of eight images, arranged in two rows and four columns. The leftmost column is baseline, the center left column is the Medium control (n=12), the center right column is Day 5 treatment (n=13), and the rightmost column is Day 7 treatment (n=8). Row A is a 2D echocardiogram (ECG) showing representative M-mode tracing at 8 weeks. Row B is a 3D regional wall velocity diagram of left ventricle endomyocardial strain over three consecutive cardiac cycles.

Looking at Row A, the top of the ECG is wavy in the Baseline image. However, in the Medium image, the top of the ECG is flat. In the Day 5 and Day 7 images, the top of the ECG is wavy again, indicating that the heart function has recovered.

In Row B, the positive values are contraction, and the negative values are relaxation. The Baseline image has three peaks (labelled I, II, and III). In the Medium image, peak II is absent. In the Day 5 and Day 7 images, peak II has returned, indicating that the heart function has recovered.

FIG. 15 is a set of three graphs comparing Medium treatment to Day 5 treatment and Day 7 treatment. FIG. 15A measures the End-Systolic Volume (ESV) in microliters (μL). FIG. 15B measures the left ventricle mass (LV) in milligrams (mg). In both cases, there is less increase over time for the Day 5 and Day 7 treatments compared to the Medium (i.e. control) treatment, indicating less cardiac hypertrophy. FIG. 15C measures the left ventricle ejection fraction (LVEF) in %. A higher LVEF is more desirable. The decline in ejection fraction was significantly less for the Day 5 and Day 7 treatments.

Live video loops generated from echocardiograms were analyzed for each animal at all time points. At baseline, the heart showed synchronous contractions and relaxations throughout the cardiac cycle. Twelve weeks after myocardial injury, the medium-injected mice showed overt chamber dilation and hypokinesis of the anterior wall. In contrast, the contractile activity of the anterior wall in day 5 progenitor injected mice was significantly improved. Improvement in contractile activity of anterior wall in day 7 progenitor injected mice was also observed. Global strains and strain rates were also calculated to assess the deformation of the left ventricle. Compared to the medium-injected animals, transplantation of cardiomyocyte progenitor cells attenuated left ventricle deformation.

At 12 weeks post-transplantation, mice were euthanized and the hearts harvested for histological analysis. FIG. 16A and FIG. 16B are a set of 12 representative images, arranged in two rows and three columns each, showing the results. The left column is from the Medium control, the center column is from the Day 5 treatment, and the right column is from the Day 7 treatment.

In FIG. 16A, Row A shows photomicrographs of the infarcted heart at the time of sacrifice. The Medium-treated hearts had a bigger infarction region (inside the dotted line) compared to the progenitor-treated hearts.

Row B shows Picrosirius Red staining of heart sections. The fibrotic area is bigger in the Medium only injected hearts than in progenitor-treated hearts. The dark areas represent fibrotic tissue. It should also be noted that the cell wall in the bottom right side of the Medium image is very thin (dotted circle), whereas the cell walls are thicker in the Day 5 and Day 7 images.

In FIG. 16B, Row C shows DAB staining, which showed areas of the infarcted region containing human cells in Day 5 and Day 7 progenitor-treated hearts (visible inside the dotted line). None were present in the Medium heart, as expected.

Finally, Row D shows angiogenesis using isolectin 4 (red) and Wheat Germ Agglutination (WGA) antibody (red). As seen in the Medium image, a large fibrotic region is visible. In the Day 5 image, blood vessels are visible in this area, and even more blood vessels are present in the Day 7 image. This indicated a significant increase in blood vessel formation.

FIG. 17 is a set of four representative images, arranged in two rows and two columns, showing human muscle fiber observed in the infarcted area 12 weeks after treatment. The left column is from the Day 5 progenitors treatment, and the right column is from the Day 7 progenitors treatment.

Row E shows confocal images of human muscle fiber stained with TNNT2 (red), KU80 (green), DAPI (blue), and connexin 43 (CX43, yellow) at 40× magnification. The yellow dotted lines demarcated the region of infarction. Row F shows the areas inside the boxes of Row E, at 100× magnification. Well-organized and parallel cytoplasmic striations were observed in both Day 5 and Day 7 progenitor-treated hearts. White asterisks indicate dispersed CX43 protein that has not yet matured and aligned into straight lines. Intercalated discs are microscopic identifying features of cardiac muscle. Cardiac muscle consists of individual heart muscle cells (cardiomyocytes) connected by intercalated discs to work as a single functional organ or syncytium. The dispersed CX43 protein shows that the intercalated discs are not yet mature. White arrows are pointing to aligned CX43 protein between two ends of adjacent cardiomyocyte cells (fibers). These indicate well organized gap junctions (intercalated discs) connecting the ends of adjacent muscle fibers. More organized CX43 staining was observed in Day 7 treated hearts, indicating a more mature muscle fiber than Day 5 treated hearts. The presence of CX43 clearly identified the end-to-end connections between cardiomyocytes. The gap junctions were well-organized at one end of the fiber, but were more dispersed at the other end, suggesting that the muscle fiber is still maturing. These images are very similar to FIG. 13F.

As a result of these experiments, gene markers were identified whose differential expression indicated that the cardiomyocyte progenitor cells were functional, i.e. the gene markers that transcriptionally defined the cardiomyocyte progenitor cells. These gene markers were identified using H1 and HS1001 human embryonic stem cells, and it is believed that they apply to cardiomyocyte progenitor cells produced from any human embryonic stem cells.

The transcriptome of the cells was profiled by RNA-sequencing separately on H1 and HS1001 human embryonic stem cells at differentiation Days 3, 5 and 7 (profiled at least three times each time point in both cell lines). These are referred to herein as "Day X" transcriptomes. Next, differential expression analysis was performed with DESeq2 R package between the Day 5 and Day 3 transcriptomes, with the Day 3 transcriptome being used as the baseline. A log2 fold change was determined for each gene, and this table of log2 fold change values is referred to herein as a "Day 5 differential transcriptome". With the same methodology, a "Day 7 differential transcriptome" was obtained by performing differential expression analysis between the Day 7 and Day 5 transcriptomes, with the Day 5 transcriptome being used as the baseline. The differential transcriptomes thus contain information on which genes are up-regulated and down-regulated. Mean transcript per million (TPM) values were computed at Day 5 and Day 7 by using the TPM values computed with RSEM software. For purposes of the present disclosure, TPM values should be considered as also being representative of Fragments per kilobase of exon model per million reads (FPKM) values, even though they can differ.

The differential expression analysis in the Day 5 differential transcriptome identified the following genes, which are listed below using their Ensembl Gene ID, external gene name, the log2 fold change for both the H1 and HS1001 cells, and the average TPM values for both the H1 and HS1001 cells at Day 5. Positive values for the Log2FC indicate up-regulation, or more expression on Day 5 compared to Day 3. Negative values for the Log2FC indicate down-regulation, or less expression on Day 5 compared to Day 3.

| Day 5 Differential Transcriptome | | | | |
|---|---|---|---|---|
| Ensembl Gene ID | Gene Name | H1-Log2FC | HS1001-Log2FC | H1-TPM | HS1001-TPM |
| ENSG00000118271 | TTR | 6.57 | 5.59 | 97.67 | 23.56 |
| ENSG00000104368 | PLAT | 6.08 | 6.02 | 29.10 | 10.61 |
| ENSG00000089225 | TBX5 | 5.20 | 5.91 | 9.74 | 11.75 |
| ENSG00000158874 | APOA2 | 4.76 | 4.51 | 88.11 | 10.97 |
| ENSG00000118137 | APOA1 | 4.41 | 4.98 | 158.43 | 12.85 |
| ENSG00000240801 | AC132217.4 | 4.27 | 2.97 | 170.02 | 66.16 |
| ENSG00000183072 | NKX2-5 | 3.69 | 4.22 | 3.53 | 3.94 |
| ENSG00000106631 | MYL7 | 3.44 | 3.05 | 262.64 | 252.99 |
| ENSG00000266010 | GATA6-AS1 | 2.64 | 1.67 | 76.45 | 66.96 |
| ENSG00000130303 | BST2 | 2.44 | 1.19 | 52.52 | 36.38 |
| ENSG00000125848 | FLRT3 | 2.13 | 2.38 | 41.48 | 27.20 |
| ENSG00000198336 | MYL4 | 2.05 | 1.63 | 101.82 | 76.40 |
| ENSG00000108515 | ENO3 | 1.84 | 1.58 | 36.63 | 52.69 |
| ENSG00000133083 | DCLK1 | −4.31 | −2.39 | 0.51 | 0.84 |
| ENSG00000236673 | RP11-69I8.2 | −5.05 | −4.48 | 0.13 | 0.09 |
| ENSG00000156925 | ZIC3 | −5.39 | −4.89 | 1.11 | 3.06 |
| ENSG00000164458 | T | −5.54 | −4.93 | 0.06 | 0.08 |
| ENSG00000143171 | RXRG | −6.03 | −3.88 | 0.10 | 0.43 |
| ENSG00000260266 | CTD-2311M21.2 | −6.25 | −5.79 | 0.06 | 0.20 |

The differential expression analysis in the Day 7 differential transcriptome identified the following genes, which are listed below using their Ensembl Gene ID, external gene name, the log2 fold change for both the H1 and HS1001 cells, and the average TPM values for both the H1 and HS1001 cells at Day 7.

| Day 7 Differential Transcriptome | | | | |
|---|---|---|---|---|
| Ensembl Gene ID | Gene Name | H1-Log2FC | HS1001-Log2FC | H1-TPM | HS1001-TPM |
| ENSG00000197616 | MYH6 | 5.07 | 5.12 | 470.98 | 567.38 |
| ENSG00000145708 | CRHBP | 4.49 | 4.12 | 61.33 | 18.94 |
| ENSG00000077522 | ACTN2 | 3.81 | 3.70 | 28.90 | 33.07 |
| ENSG00000183023 | SLC8A1 | 3.42 | 3.42 | 40.76 | 48.23 |
| ENSG00000118194 | TNNT2 | 3.05 | 2.86 | 388.87 | 356.54 |
| ENSG00000159251 | ACTC1 | 2.97 | 2.30 | 550.74 | 418.55 |
| ENSG00000159173 | TNNI1 | 2.78 | 2.61 | 210.24 | 203.17 |
| ENSG00000148677 | ANKRD1 | 2.45 | 1.50 | 159.42 | 149.01 |
| ENSG00000106631 | MYL7 | 2.43 | 2.24 | 1230.72 | 1255.37 |
| ENSG00000185559 | DLK1 | 2.14 | 2.26 | 62.27 | 133.32 |
| ENSG00000198336 | MYL4 | 2.09 | 2.36 | 365.20 | 363.77 |

-continued

| Day 7 Differential Transcriptome | | | | | |
| --- | --- | --- | --- | --- | --- |
| Ensembl Gene ID | Gene Name | H1-Log2FC | HS1001-Log2FC | H1-TPM | HS1001-TPM |
| ENSG00000138685 | FGF2 | −0.60 | −0.55 | 1.16 | 1.77 |
| ENSG00000043355 | ZIC2 | −1.25 | −1.24 | 0.28 | 1.33 |
| ENSG00000260834 | RP11-256I9.2 | −2.57 | −2.99 | 0.03 | 0.90 |
| ENSG00000139292 | LGR5 | −2.58 | −3.08 | 0.72 | 0.41 |
| ENSG00000123560 | PLP1 | −3.03 | −1.49 | 1.35 | 3.44 |
| ENSG00000234787 | LINC00458 | −3.41 | −2.34 | 0.16 | 0.31 |

The genes identified through bulk RNA sequencing in these two tables were validated using real-time quantitative PCR (qPCR). Primers were designed using NCBI Primer-BLAST tool. Total RNA from Day 5 or Day 7 cardiovascular progenitor cells were purified using a single-cell RNA purification kit (Norgen Biotek Corporation) according to manufacturer's guidelines. The yield was determined by a NanoDrop ND-2000 spectrophotometer (NanoDrop Technologies). The cDNA was synthesized from the total RNA using a TaqMan Reverse Transcription Reagents Kit (Applied BioSystems) according to the manufacturer's instructions. Real-time qRT-PCR was performed with synthesized cDNA in assay mix containing iQ SYBR Green Super mix (Bio-Rad) and primers for genes of interest. Relative gene expression was normalized to Ataxin 2 (ATXN2) or Mitochondrial trans-2-Enoyl-CoA Reductase (MECR), which served as normalizing controls.

The results demonstrated that genes having a TPM value of 10 or greater have a relative expression higher than ATXN2 or MECR (i.e. the relative expression is greater than 1). The genes having a TPM value of less than 5 have a relative expression lower than ATXN2 or MECR (i.e. the relative expression is less than 1). Other methods of assessing relative gene expression can also be used.

Protein levels of Day 5 and Day 7 progenitors could also be examined using Western blot and probing with specific antibodies against the proteins expressed by the genes in the two tables above in order to determine their relative expression levels. Other methods to study protein expression could also be used.

It is thus generally contemplated that a cardiomyocyte progenitor cell or cell population can be identified as functional and suitable for transplantation into a mammal if it (A) expresses one or more of these gene markers; and (B) the gene marker(s) is highly differentially expressed. A suitable log2 fold change (Log2FC) value or TPM value indicates the gene marker is highly differentially expressed.

In embodiments, the Log2FC value for up-regulated genes may be at least 1, at least 2, at least 3, at least 4, at least 5, at least 6, or at least 7. While there is no theoretical maximum Log2FC value, generally speaking the Log2FC value for an up-regulated gene will not exceed 10.

In embodiments, the Log2FC value for down-regulated genes may be at least −0.2, at least −0.5, at least −1, at least −2, at least −3, at least −4, at least −5, or at least −6. It is noted that for these negative values, the phrase "at least" includes the given value and numbers less than the given value. For example, "at least −2" includes the value −3, but does not include the value −1. While there is no theoretical minimum Log2FC value, generally speaking the Log2FC value for a down-regulated gene will not exceed −10.

In embodiments, a TPM or FPKM value of at least 10 indicates the gene is robustly expressed. Although the theoretical maximum for TPM is one million and there is no theoretical maximum for FPKM value, generally speaking the TPM or FPKM value will not exceed two thousand (2000). A TPM or FPKM value of less than 5 indicates the gene is minimally expressed. The theoretical minimum TPM or FPKM value is zero (0).

Various combinations of genes are contemplated as indicating that a cardiomyocyte progenitor cell or cell population can be identified as functional and suitable for transplantation.

In some embodiments, a cardiomyocyte progenitor cell or cell population is functional if its Day 5 differential transcriptome shows that at least one of genes TTR, PLAT, TBX5, APOA2, APOA1, AC132217.4, NKX2-5, MYL7, GATA6-AS1, BST2, FLRT3, MYL4, and ENO3 are up-regulated by a Log2FC value of at least 1, or at least 2, or at least 3, or at least 4, or at least 5. Combinations of any 2, 3, 4, 5, 6, 7, 8, 9, 10, 11, 12, or 13 of these genes are specifically contemplated. In some embodiments, the combination of up-regulated genes includes at least one of TTR, PLAT, and TBX5, or at least two, or all three, of these three genes.

In some embodiments, a cardiomyocyte progenitor cell or cell population is functional if its Day 5 differential transcriptome shows that at least one of genes TBX5, NKX2-5, TTR, APOA1, and MYL7 are up-regulated by a Log2FC value of at least 2, or at least 3, or at least 4, or at least 5. This includes at least two of the five genes, or at least three of the five genes, or at least four of the five genes, or all of the five genes having or exceeding a given Log2FC value. In particular embodiments, the two genes are TTR and APOA1. In other embodiments, the two genes are TTR and TBX5. In particular embodiments, the three genes are TTR, TBX5, and APOA1.

In some embodiments, a cardiomyocyte progenitor cell or cell population is functional if its Day 5 differential transcriptome shows that at least one of genes DCLK1, RP11-6918.2, ZIC3, T, RXRG, and CTD-2311M21.2 are down-regulated by a Log2FC value of at least −0.5, at least −2, or at least −4, or at least −5, or at least −6. Combinations of any 2, 3, 4, 5, or 6 of these genes are specifically contemplated. In some embodiments, the combination of down-regulated genes includes at least one of T, RXRG, and CTD-2311M21.2, or at least two, or all three, of these three genes.

In some embodiments, a cardiomyocyte progenitor cell or cell population is functional if its Day 5 differential transcriptome shows that at least one of genes RXRG and T are down-regulated by a Log2FC value of at least −2, or at least −4, or at least −5. In particular embodiments, both RXRG and T are so down-regulated.

Combinations of up-regulated and down-regulated genes are also contemplated. For example, a cardiomyocyte progenitor cell or cell population is functional if its Day 5 differential transcriptome shows that (A) at least one of genes TTR, PLAT, TBX5, APOA2, APOA1, AC132217.4, NKX2-5, MYL7, GATA6-AS1, BST2, FLRT3, MYL4, and ENO3 are up-regulated by a Log2FC value of at least 1, and (B) at least one of genes DCLK1, RP11-69I8.2, ZIC3, T, RXRG, and CTD-2311M21.2 are down-regulated by a Log2FC value of at least −0.5. Again, combinations of at least two of these genes are contemplated.

In additional embodiments, a cardiomyocyte progenitor cell or cell population is functional if its Day 5 differential transcriptome shows that (A) at least one of genes TBX5, NKX2-5, TTR, APOA1, and MYL7 are up-regulated by a Log2FC value of at least 2, and (B) at least one of genes RXRG and T are down-regulated by a Log2FC value of at least −2. Any combination of genes is contemplated, including: (1) at least two of the five up-regulated genes with at least one of the two down-regulated genes; (2) at least three of the five up-regulated genes with at least one of the two down-regulated genes; (3) at least four of the five up-regulated genes with at least one of the two down-regulated genes; (4) all five of the five up-regulated genes with at least one of the two down-regulated genes; (5) at least two of the five up-regulated genes with both of the down-regulated genes; (6) at least three of the five up-regulated genes with both of the down-regulated genes; (7) at least four of the five up-regulated genes with both of the down-regulated genes; and (8) all five of the five up-regulated genes with both of the down-regulated genes. In addition, any combination of Log2FC values is contemplated, including: (1) the up-regulated genes having a Log2FC value of at least 3, at least 4, at least 5, or at least 6; and (2) the down-regulated genes having a Log2FC value of at least −2, at least −3, at least −4, at least −5, or at least −6.

In some specific embodiments, a cardiomyocyte progenitor cell or cell population is functional if its Day 5 differential transcriptome shows that (A) at least one of genes TTR, PLAT, APOA2, APOA1, AC132217.4, GATA6-AS1, BST2, FLRT3, MYL4, and ENO3 are up-regulated by a Log2FC value of at least 1, and (B) at least one of genes DCLK1, RP11-69I8.2, ZIC3, RXRG, and CTD-2311M21.2 are down-regulated by a Log2FC value of at least −0.5. Again, combinations of at least two of these genes are contemplated.

In one particular set of embodiments, a cardiomyocyte progenitor cell or cell population is functional if its Day 5 differential transcriptome shows that (A) at least one of genes TTR and APOA1 are up-regulated by a Log2FC value of at least 2, and (B) the gene RXRG is down-regulated by a Log2FC value of at least −2.

In some embodiments, a cardiomyocyte progenitor cell or cell population is functional if its Day 7 differential transcriptome shows that at least one of genes MYH6, CRHBP, ACTN2, SLC8A1, TNNT2, ACTC1, TNNI1, ANKRD1, MYL7, DLK1, and MYL4 are up-regulated by a Log2FC value of at least 1, or at least 2, or at least 3, or at least 4. Combinations of any 2, 3, 4, 5, 6, 7, 8, 9, 10, or 11 of these genes are specifically contemplated. In some embodiments, the combination of up-regulated genes includes at least one of MYH6, CRHBP, ACTN2, SLC8A1, and TNNT2, or at least two, or at least three, or at least four, or all five, of these five genes.

In some embodiments, a cardiomyocyte progenitor cell or cell population is functional if its Day 7 differential transcriptome shows that at least one of genes MYH6, ANKRD1, TNNT2, ACTC1, and CRHBP are up-regulated by a Log2FC value of at least 2, or at least 4, or at least 5. This includes at least two of the five genes, or at least three of the five genes, or at least four of the five genes, or all of the five genes having or exceeding a given Log2FC value. In particular embodiments, the two genes are ANKRD1 and CRHBP. In other embodiments, the two genes are MYH6 and CRHBP.

In some embodiments, a cardiomyocyte progenitor cell or cell population is functional if its Day 7 differential transcriptome shows that at least one of genes FGF2, ZIC2, RP11-256I9.2, LGR5, PLP1, and LINC00458 are down-regulated by a Log2FC value of at least −0.2, at least −0.5, or at least −1, or at least −2, or at least −3. Combinations of any 2, 3, 4, 5, or 6 of these genes are specifically contemplated.

In some embodiments, a cardiomyocyte progenitor cell or cell population is functional if its Day 7 differential transcriptome shows that at least one of genes LGR5 and PLP1 are down-regulated by a Log2FC value of at least −2. In particular embodiments, both LGR5 and PLP1 are so down-regulated.

Combinations of up-regulated and down-regulated genes are also contemplated for the Day 7 differential transcriptome. For example, a cardiomyocyte progenitor cell or cell population is functional if its Day 7 differential transcriptome shows that (A) at least one of genes MYH6, CRHBP, ACTN2, SLC8A1, TNNT2, ACTC1, TNNI1, ANKRD1, MYL7, DLK1, and MYL4 are up-regulated by a Log2FC value of at least 1, and (B) at least one of genes FGF2, ZIC2, RP11-256I9.2, LGR5, PLP1, and LINC00458 are down-regulated by a Log2FC value of at least −0.2. Again, combinations of at least two of these genes are contemplated.

In additional embodiments, a cardiomyocyte progenitor cell or cell population is functional if its Day 7 differential transcriptome shows that (A) at least one of genes MYH6, ANKRD1, TNNT2, ACTC1, and CRHBP are up-regulated by a Log2FC value of at least 2, and (B) at least one of genes LGR5 and PLP1 are down-regulated by a Log2FC value of at least −2. Any combination of genes is contemplated, including: (1) at least two of the five up-regulated genes with at least one of the two down-regulated genes; (2) at least three of the five up-regulated genes with at least one of the two down-regulated genes; (3) at least four of the five up-regulated genes with at least one of the two down-regulated genes; (4) all five of the five up-regulated genes with at least one of the two down-regulated genes; (5) at least two of the five up-regulated genes with both of the down-regulated genes; (6) at least three of the five up-regulated genes with both of the down-regulated genes; (7) at least four of the five up-regulated genes with both of the down-regulated genes; and (8) all five of the five up-regulated genes with both of the down-regulated genes. In addition, any combination of Log2FC values is contemplated, specifically: (1) the up-regulated genes having a Log2FC value of at least 3, or at least 4; and (2) the down-regulated genes having a Log2FC value of at least −2.

In other embodiments, a cardiomyocyte progenitor cell or cell population is functional if its Day 7 differential transcriptome shows that (A) at least one of genes CRHBP, ACTN2, SLC8A1, TNNI1, ANKRD1, MYL7, DLK1, and MYL4 are up-regulated by a Log2FC value of at least 1, and (B) at least one of genes FGF2, ZIC2, RP11-256I9.2, LGR5, PLP1, and LINC00458 are down-regulated by a Log2FC value of at least −0.2.

In still more specific embodiments, a cardiomyocyte progenitor cell or cell population is functional if its Day 7 differential transcriptome shows that (A) at least one of genes ANKRD1 and CRHBP are up-regulated by a Log2FC value of at least 1, and (B) at least one of genes LGR5 and PLP1 are down-regulated by a Log2FC value of at least −0.2.

In some embodiments, a cardiomyocyte progenitor cell or cell population is functional if its Day 5 differential transcriptome shows that at least one of genes TTR, PLAT, TBX5, APOA2, APOA1, AC132217.4, MYL7, GATA6-AS1, BST2, FLRT3, MYL4, and ENO3 has a TPM or FPKM value of at least 10. Combinations of any 2, 3, 4, 5, 6, 7, 8, 9, 10, 11, or 12 of these genes having a TPM or FPKM value of at least 10 are specifically contemplated. In some embodiments, the combination of genes includes at least one of APOA1, AC132217.4, MYL7, or MYL4, or at least two, or three, or all four of these four genes.

In other embodiments, a cardiomyocyte progenitor cell or cell population is functional if its Day 5 differential transcriptome shows that at least one of genes DCLK1, RP11-69I8.2, ZIC3, T, RXRG, and CTD-2311M21.2 has a TPM or FPKM value of less than 5. Combinations of any 2, 3, 4, 5, or 6 of these genes having a TPM or FPKM value of less than 5 are specifically contemplated.

In additional embodiments, a cardiomyocyte progenitor cell or cell population is functional if its Day 7 differential transcriptome shows that at least one of genes MYH6, CRHBP, ACTN2, SLC8A1, TNNT2, ACTC1, TNNI1, ANKRD1, MYL7, DLK1 and MYL4 has a TPM or FPKM value of at least 10. Combinations of any 2, 3, 4, 5, 6, 7, 8, 9, 10, or 11 of these genes having a TPM or FPKM value of at least 10 are specifically contemplated.

In still other embodiments, a cardiomyocyte progenitor cell or cell population is functional if its Day 7 differential transcriptome shows that at least one of genes FGF2, ZIC2, RP11-256I9.2, LGR5, PLP1, and LINC00458 has a TPM or FPKM value of less than 5. Combinations of any 2, 3, 4, 5, or 6 of these genes having a TPM or FPKM value of less than 5 are specifically contemplated.

Combinations of up-regulated and down-regulated genes are also contemplated for the Day 5 and Day 7 differential transcriptomes based on their TPM value. For example, a cardiomyocyte progenitor cell or cell population is functional if its Day 5 differential transcriptome shows that (A) at least one of genes TTR, PLAT, TBX5, APOA2, APOA1, AC132217.4, MYL7, GATA6-AS1, BST2, FLRT3, MYL4, and ENO3 has a TPM or FPKM value of at least 10, and (B) at least one of genes DCLK1, RP11-69I8.2, ZIC3, T, RXRG, and CTD-2311M21.2 has a TPM or FPKM value of less than 5. As another example, a cardiomyocyte progenitor cell or cell population is functional if its Day 7 differential transcriptome shows that (A) at least one of genes MYH6, CRHBP, ACTN2, SLC8A1, TNNT2, ACTC1, TNNI1, ANKRD1, MYL7, DLK1 and MYL4 has a TPM or FPKM value of at least 10, and (B) at least one of genes FGF2, ZIC2, RP11-256I9.2, LGR5, PLP1, and LINC00458 has a TPM or FPKM value of less than 5. Again, combinations of at least two of these genes are contemplated for each condition.

After being identified, the functional cardiomyocyte progenitor cell or cell population can be separated from non-functional cells. They can then be used for implantation and treatment purposes. They can be mixed with appropriate ingredients as needed to make up compositions for implantation and treatment.

Continuing, in vivo characterization and safety of the cardiomyocyte progenitors was also performed. First, karyotyping was done for cardiomyocytes, and the cells retained normal 46 XY karyotype. This showed the differentiation protocol did not alter the chromosomal numbers and stability of the cells.

Next, to assess the in vivo safety of the progenitors, a teratoma formation assay was performed in nude mice (8-10 weeks old, 20-25 grams). H1 pluripotent stem cells or progenitors (5 million cells) were resuspended in 100 μL of Matrigel™ (Corning) and injected once intramuscularly into the hind limb muscle, and the mice were kept for 8 weeks. FIG. 18 is a photograph of a mouse injected with the progenitors (left) and a mouse injected with H1 stem cells (right), taken after the 8-week period. As can be seen, the progenitors did not result in teratoma.

Next, samples of injected tissue were excised, fixed in formalin and routinely processed through paraffin and staining with Hematoxylin and Eosin. Images were examined under light microscopy (Olympus) by an ACVP board-certified veterinary pathologist. FIG. 19 shows the hematoxylin and eosin staining of a teratoma isolated from the mouse to which pluripotent H1 stem cells were administered. This figure shows ectoderm (neural rosette), mesoderm (bone and cartilage) and endoderm (pancreas) germ layers.

Example 5

Study of LN-221 for Cell Differentiation and Safety

Transcriptomic experiments were performed to determine the cell differentiation potential of LN-221 in pluripotent cells. H1 stem cells were cultured for four days on a substrate containing only LN-521. They were cultured on a substrate of either (i) only LN-521 or (ii) a 1:3 combination of LN-521 and LN-221 for another four days. A differential gene analysis was then performed between the two substrates. The top 10 up-regulated and down-regulated genes (by fold change) were identified; all passed the 0.05 Benjamini-Hochberg adjust p-value significance threshold. FIG. 20 also illustrates the analysis.

The top 10 up-regulated genes all had a Log2FC of at least 0.5. In no particular order, they were NEBL, FRZB, IRX1, LMO1, TGFB2, FLRT3, GREB1L, LHX5-AS1. ACADSB, and PPP1R1B. These genes related to cardiac myofibril assembly, Wnt signaling, blood lineage, and heart development, which are desirably up-regulated in cardiomyocytes.

The top 10 down-regulated genes all had a Log2FC of at least −0.5. In no particular order, they were NPTX1, MT1H, MT1G, MT1E, MT2A, FOXD3, TDGF1, MTX1, PDZD4, and NANOG. These genes related to teratocarcinoma derived growth factor, human tumors, and pluripotency, which are desirably down-regulated in cardiomyocytes.

The results were reproducible over time. FIG. 21 is a set of graphs showing transcriptome comparison between H1 and HS1001 cell lines on 12 different days over a 94-day differentiation period. At all time-points, H1 and HS1001 transcriptomes were correlated with each other.

The present disclosure has been described with reference to exemplary embodiments. Obviously, modifications and alterations will occur to others upon reading and understanding the preceding detailed description. It is intended that the present disclosure be construed as including all such modifications and alterations insofar that they come within the scope of the appended claims or the equivalents thereof.

The invention claimed is:

1. A method for treating injured human cardiac muscle, comprising:

(a) culturing human pluripotent stem cells on a culture plate coated with a substrate in a medium containing basic fibroblast growth factor (bFGF), wherein the substrate comprises a mixture of two laminins consisting of (i) recombinant LN-521 or recombinant LN-511 and (ii) recombinant LN-221;

(b) culturing the pluripotent stem cells on the substrate in the presence of a differentiation medium containing an effective amount of a GSK-3 inhibitor to stimulate Wnt signaling and obtain brachyury positive cells;

(c) culturing the brachyury positive cells from step (b) on the substrate in a differentiation medium containing an effective amount of a Wnt inhibitor to promote cardiac mesodermal specification;

(d) removing the differentiation medium containing the Wnt inhibitor from step (c) and replacing with a basal medium to culture the cells on the substrate to produce human cardiomyocyte progenitor cells that express Islet-1 and NKX2.5 transcription factor; and (e) transplanting the human cardiomyocyte progenitor cells into the injured human cardiac muscle.

2. The method of claim 1, wherein:

the pluripotent stem cells are cultured in the presence of the differentiation medium containing an effective amount of a GSK-3 inhibitor for a first time period of about 12 hours to about 48 hours;

the brachyury positive cells are cultured in a cell culture medium devoid of inhibitors for a second time period of about 12 hours to about 48 hours before being cultured in the differentiation medium containing an effective amount of a Wnt inhibitor; and the brachyury positive cells are cultured in the differentiation medium containing an effective amount of a Wnt inhibitor for a third time period of about 12 hours to about 48 hours.

3. The method of claim 2, wherein the cardiomyocyte progenitor cells are obtained by the fifth day after the beginning of differentiation.

4. The method of claim 2, wherein the cells in step (d) are cultured for up to 2 days in the basal medium.

5. The method of claim 1, wherein the step (a) has a duration of about 4 days.

6. The method of claim 1, wherein the differentiation media and the basal medium are chemically defined and xeno-free.

* * * * *